(12) United States Patent
Demarais et al.

(10) Patent No.: US 8,845,629 B2
(45) Date of Patent: Sep. 30, 2014

(54) ULTRASOUND APPARATUSES FOR THERMALLY-INDUCED RENAL NEUROMODULATION

(75) Inventors: Denise Demarais, Saratoga, CA (US); Nicolas Zadno, Fremont, CA (US); Benjamin J. Clark, Redwood City, CA (US); Erik Thai, San Jose, CA (US); Howard R. Levin, Teaneck, NJ (US); Mark Gelfand, New York, NY (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 1026 days.

(21) Appl. No.: 12/754,337

(22) Filed: Apr. 5, 2010

(65) Prior Publication Data
US 2010/0191112 A1 Jul. 29, 2010

Related U.S. Application Data

(63) Continuation of application No. 11/840,142, filed on Aug. 16, 2007, now Pat. No. 7,717,948, which is a continuation of application No. 11/504,117, filed on Aug. 14, 2006, now Pat. No. 7,617,005, and a continuation-in-part of application No. 10/408,665, filed on Apr. 8, 2003, now Pat. No. 7,162,303, said application No. 11/504,117 is a continuation-in-part of application No. 11/189,563, filed on Jul. 25, 2005, now Pat. No. 8,145,316, which is a continuation-in-part of application No. 11/129,765, filed on May 13, 2005, now Pat. No. 7,653,438.

(60) Provisional application No. 60/816,999, filed on Jun. 28, 2006, provisional application No. 60/370,190, filed on Apr. 8, 2002, provisional application No. 60/415,575, filed on Oct. 3, 2002, provisional application No. 60/442,970, filed on Jan. 29, 2003, provisional application No. 60/616,254, filed on Oct. 5, 2004, provisional application No. 60/624,793, filed on Nov. 2, 2004.

(51) Int. Cl.
| | |
|---|---|
| *A61N 7/02* | (2006.01) |
| *A61B 18/12* | (2006.01) |
| *A61N 1/28* | (2006.01) |
| *A61N 1/40* | (2006.01) |
| *A61F 7/00* | (2006.01) |
| *A61N 5/04* | (2006.01) |
| *A61B 18/04* | (2006.01) |
| *A61B 18/02* | (2006.01) |
| *A61F 7/12* | (2006.01) |
| *A61N 7/00* | (2006.01) |
| *A61N 1/36* | (2006.01) |

(52) U.S. Cl.
CPC . *A61B 18/12* (2013.01); *A61N 7/02* (2013.01); *A61N 7/12* (2013.01); *A61F 2007/126* (2013.01); *A61N 2007/003* (2013.01); *A61N 1/28* (2013.01); *A61N 1/403* (2013.01); *A61F 7/123* (2013.01); *A61F 7/007* (2013.01); *A61N 5/045* (2013.01); *A61N 1/36007* (2013.01); *A61B 18/04* (2013.01); *A61B 18/02* (2013.01); *A61N 7/00* (2013.01)
USPC ............ 606/27; 606/28; 601/1; 601/15

(58) Field of Classification Search
CPC ..... A61F 7/12; A61F 7/123; A61F 2007/126; A61N 7/02; A61N 7/022; A61N 2007/0065; A61N 2007/025; A61N 2007/0021; A61N 2007/003; A61N 2007/0056
USPC .................... 606/27–31; 601/1, 15
See application file for complete search history.

(56) References Cited

U.S. PATENT DOCUMENTS

| | | |
|---|---|---|
| 2,130,758 A | 9/1938 | Rose |
| 2,276,995 A | 3/1942 | Milinowski |

(Continued)

FOREIGN PATENT DOCUMENTS

| | | |
|---|---|---|
| CN | 102551878 | 7/2012 |
| DE | 3151180 | 8/1982 |

(Continued)

OTHER PUBLICATIONS

U.S. Appl. No. 12/940,922, filed Nov. 5, 2010, Gelfand et al.

(Continued)

*Primary Examiner* — Linda Dvorak
*Assistant Examiner* — Kaitlyn Smith

(57) ABSTRACT

Methods and apparatus are provided for thermally-induced renal neuromodulation. Thermally-induced renal neuromodulation may be achieved via direct and/or via indirect application of thermal energy to heat or cool neural fibers that contribute to renal function, or of vascular structures that feed or perfuse the neural fibers. In some embodiments, parameters of the neural fibers, of non-target tissue, or of the thermal energy delivery element, may be monitored via one or more sensors for controlling the thermally-induced neuromodulation. In some embodiments, protective elements may be provided to reduce a degree of thermal damage induced in the non-target tissues.

12 Claims, 8 Drawing Sheets

(56) References Cited

U.S. PATENT DOCUMENTS

| | | | |
|---|---|---|---|
| 2,276,996 A | 3/1942 | Milinowski | |
| 3,043,310 A | 7/1962 | Milinowski | |
| 3,127,895 A | 4/1964 | Kendall et al. | |
| 3,181,535 A | 5/1965 | Milinowski | |
| 3,270,746 A | 9/1966 | Kendall et al. | |
| 3,329,149 A | 7/1967 | Kendall et al. | |
| 3,522,811 A | 8/1970 | Schwartz et al. | |
| 3,563,246 A | 2/1971 | Puharich et al. | |
| 3,650,277 A | 3/1972 | Sjostrand et al. | |
| 3,670,737 A | 6/1972 | Pearo | |
| 3,760,812 A | 9/1973 | Timm et al. | |
| 3,774,620 A | 11/1973 | Hansjurgens | |
| 3,794,022 A | 2/1974 | Nawracaj et al. | |
| 3,800,802 A | 4/1974 | Berry et al. | |
| 3,803,463 A | 4/1974 | Cover | |
| 3,894,532 A | 7/1975 | Morey | |
| 3,895,639 A | 7/1975 | Rodler et al. | |
| 3,897,789 A | 8/1975 | Blanchard | |
| 3,911,930 A | 10/1975 | Hagfors et al. | |
| 3,952,751 A | 4/1976 | Yarger | |
| 3,987,790 A | 10/1976 | Eckenhoff et al. | |
| 4,011,861 A | 3/1977 | Enger | |
| 4,026,300 A | 5/1977 | DeLuca et al. | |
| 4,055,190 A | 10/1977 | Tany | |
| 4,071,033 A | 1/1978 | Nawracaj et al. | |
| 4,105,017 A | 8/1978 | Ryaby et al. | |
| 4,141,365 A | 2/1979 | Fischell et al. | |
| 4,266,532 A | 5/1981 | Ryaby et al. | |
| 4,266,533 A | 5/1981 | Ryaby et al. | |
| 4,305,115 A | 12/1981 | Armitage | |
| 4,315,503 A | 2/1982 | Ryaby et al. | |
| 4,360,019 A | 11/1982 | Portner et al. | |
| 4,379,462 A | 4/1983 | Borkan et al. | |
| 4,405,305 A | 9/1983 | Stephen et al. | |
| 4,454,883 A | 6/1984 | Fellus | |
| 4,467,808 A | 8/1984 | Brighton et al. | |
| 4,487,603 A | 12/1984 | Harris | |
| 4,530,840 A | 7/1985 | Tice et al. | |
| 4,587,975 A | 5/1986 | Salo et al. | |
| 4,602,624 A | 7/1986 | Naples et al. | |
| 4,608,985 A | 9/1986 | Crish et al. | |
| 4,649,936 A | 3/1987 | Ungar et al. | |
| 4,658,828 A | 4/1987 | Dory | |
| 4,671,286 A | 6/1987 | Renault | |
| 4,674,482 A | 6/1987 | Waltonen et al. | |
| 4,692,147 A | 9/1987 | Duggan | |
| 4,715,852 A | 12/1987 | Reinicke et al. | |
| 4,774,967 A | 10/1988 | Zanakis | |
| 4,791,931 A | 12/1988 | Slate | |
| 4,816,016 A | 3/1989 | Schulte et al. | |
| 4,852,573 A | 8/1989 | Kennedy | |
| 4,858,613 A | 8/1989 | Fry et al. | |
| 4,865,845 A | 9/1989 | Eckenhoff et al. | |
| 4,955,377 A | 9/1990 | Lennox et al. | |
| 4,976,711 A | 12/1990 | Parins et al. | |
| 4,979,511 A | 12/1990 | Terry, Jr. | |
| 4,981,146 A | 1/1991 | Bertolucci | |
| 4,986,275 A | 1/1991 | Ishida et al. | |
| 4,998,532 A | 3/1991 | Griffith | |
| 5,006,119 A | 4/1991 | Acker et al. | |
| RE33,590 E | 5/1991 | Dory | |
| 5,014,699 A | 5/1991 | Pollack et al. | |
| 5,019,034 A | 5/1991 | Weaver et al. | |
| 5,057,318 A | 10/1991 | Magruder et al. | |
| 5,058,584 A | 10/1991 | Bourgeois | |
| 5,059,423 A | 10/1991 | Magruder et al. | |
| 5,061,492 A | 10/1991 | Okada et al. | |
| 5,065,740 A | 11/1991 | Itoh | |
| 5,080,101 A | 1/1992 | Dory | |
| 5,094,242 A | 3/1992 | Gleason et al. | |
| 5,111,815 A | 5/1992 | Mower | |
| 5,112,614 A | 5/1992 | Magruder et al. | |
| 5,125,928 A | 6/1992 | Parins et al. | |
| 5,131,409 A | 7/1992 | Lobarev et al. | |
| 5,137,727 A | 8/1992 | Eckenhoff | |
| 5,188,837 A | 2/1993 | Domb | |
| 5,193,048 A | 3/1993 | Kaufman et al. | |
| 5,193,539 A | 3/1993 | Schulman et al. | |
| 5,193,540 A | 3/1993 | Schulman et al. | |
| 5,199,428 A | 4/1993 | Obel et al. | |
| 5,203,326 A | 4/1993 | Collins et al. | |
| 5,213,098 A | 5/1993 | Bennett et al. | |
| 5,215,086 A | 6/1993 | Terry, Jr. et al. | |
| 5,231,988 A | 8/1993 | Wernicke et al. | |
| 5,234,692 A | 8/1993 | Magruder et al. | |
| 5,234,693 A | 8/1993 | Magruder et al. | |
| 5,251,634 A | 10/1993 | Weinberg | |
| 5,251,643 A | 10/1993 | Osypka | |
| 5,263,480 A | 11/1993 | Wernicke et al. | |
| 5,269,303 A | 12/1993 | Wernicke et al. | |
| 5,282,468 A | 2/1994 | Klepinski | |
| 5,282,785 A | 2/1994 | Shapland et al. | |
| 5,286,254 A | 2/1994 | Shapland et al. | |
| 5,299,569 A | 4/1994 | Wernicke et al. | |
| 5,300,068 A | 4/1994 | Rosar et al. | |
| 5,304,120 A | 4/1994 | Crandell et al. | |
| 5,304,206 A | 4/1994 | Baker | |
| 5,317,155 A | 5/1994 | King | |
| 5,324,255 A | 6/1994 | Passafaro et al. | |
| 5,324,316 A | 6/1994 | Schulman et al. | |
| 5,334,193 A | 8/1994 | Nardella | |
| 5,335,657 A | 8/1994 | Terry, Jr. et al. | |
| 5,338,662 A | 8/1994 | Sadri | |
| 5,351,394 A | 10/1994 | Weinberg | |
| 5,358,514 A | 10/1994 | Schulman et al. | |
| 5,368,591 A * | 11/1994 | Lennox et al. | 606/27 |
| 5,370,680 A | 12/1994 | Proctor | |
| 5,389,069 A | 2/1995 | Weaver | |
| 5,397,308 A | 3/1995 | Ellis et al. | |
| 5,397,338 A | 3/1995 | Grey et al. | |
| 5,400,784 A | 3/1995 | Durand et al. | |
| 5,405,367 A | 4/1995 | Schulman et al. | |
| 5,423,744 A | 6/1995 | Gencheff et al. | |
| 5,429,634 A | 7/1995 | Narciso, Jr. | |
| 5,433,739 A | 7/1995 | Sluijter et al. | |
| 5,439,440 A | 8/1995 | Hofmann | |
| 5,454,782 A | 10/1995 | Perkins | |
| 5,454,809 A | 10/1995 | Janssen | |
| 5,458,568 A | 10/1995 | Racchini et al. | |
| 5,458,626 A | 10/1995 | Krause | |
| 5,458,631 A | 10/1995 | Xavier | |
| 5,470,352 A | 11/1995 | Rappaport | |
| 5,471,988 A * | 12/1995 | Fujio et al. | 600/439 |
| 5,472,406 A | 12/1995 | de la Torre et al. | |
| 5,478,303 A | 12/1995 | Foley-Nolan et al. | |
| 5,484,400 A | 1/1996 | Edwards et al. | |
| 5,494,822 A | 2/1996 | Sadri | |
| 5,498,238 A | 3/1996 | Shapland et al. | |
| 5,499,971 A | 3/1996 | Shapland et al. | |
| 5,505,700 A | 4/1996 | Leone et al. | |
| 5,507,724 A | 4/1996 | Hofmann et al. | |
| 5,507,791 A | 4/1996 | Sit'ko | |
| 5,531,778 A | 7/1996 | Maschino et al. | |
| 5,540,730 A | 7/1996 | Terry, Jr. et al. | |
| 5,540,734 A | 7/1996 | Zabara | |
| 5,553,611 A | 9/1996 | Budd et al. | |
| 5,560,360 A | 10/1996 | Filler et al. | |
| 5,569,198 A | 10/1996 | Racchini | |
| 5,571,147 A | 11/1996 | Sluijter et al. | |
| 5,571,150 A | 11/1996 | Wernicke et al. | |
| 5,573,552 A | 11/1996 | Hansjurgens | |
| 5,584,863 A | 12/1996 | Rauch et al. | |
| 5,588,434 A * | 12/1996 | Fujimoto | 600/443 |
| 5,589,192 A | 12/1996 | Okabe et al. | |
| 5,599,345 A | 2/1997 | Edwards et al. | |
| 5,618,563 A | 4/1997 | Berde et al. | |
| 5,626,576 A | 5/1997 | Janssen | |
| 5,626,862 A | 5/1997 | Brem et al. | |
| 5,628,730 A | 5/1997 | Shapland et al. | |
| 5,634,462 A | 6/1997 | Tyler et al. | |
| 5,634,899 A | 6/1997 | Shapland et al. | |
| 5,672,174 A | 9/1997 | Gough et al. | |
| 5,688,266 A | 11/1997 | Edwards et al. | |
| 5,689,877 A | 11/1997 | Grill, Jr. et al. | |

(56) References Cited

U.S. PATENT DOCUMENTS

| | | | |
|---|---|---|---|
| 5,690,691 A | 11/1997 | Chen et al. | |
| 5,700,282 A | 12/1997 | Zabara | |
| 5,700,485 A | 12/1997 | Berde et al. | |
| 5,704,908 A | 1/1998 | Hofmann et al. | |
| 5,707,400 A | 1/1998 | Terry, Jr. et al. | |
| 5,711,326 A | 1/1998 | Thies et al. | |
| 5,713,847 A | 2/1998 | Howard, III et al. | |
| 5,722,401 A | 3/1998 | Pietroski et al. | |
| 5,723,001 A | 3/1998 | Pilla et al. | |
| 5,725,563 A | 3/1998 | Klotz et al. | |
| 5,728,396 A | 3/1998 | Peery et al. | |
| 5,747,060 A | 5/1998 | Sackler et al. | |
| 5,755,750 A | 5/1998 | Petruska et al. | |
| 5,756,115 A | 5/1998 | Moo-Young et al. | |
| 5,772,590 A | 6/1998 | Webster, Jr. | |
| 5,779,644 A | 7/1998 | Eberle et al. | |
| 5,792,187 A | 8/1998 | Adams | |
| 5,800,464 A | 9/1998 | Kieval | |
| 5,807,306 A | 9/1998 | Shapland et al. | |
| 5,810,802 A | 9/1998 | Panescu et al. | |
| 5,814,079 A | 9/1998 | Kieval | |
| 5,824,087 A | 10/1998 | Aspden et al. | |
| 5,836,935 A | 11/1998 | Ashton et al. | |
| RE35,987 E | 12/1998 | Harris et al. | |
| 5,843,069 A | 12/1998 | Butler et al. | |
| 5,861,021 A | 1/1999 | Thorne et al. | |
| 5,865,787 A | 2/1999 | Shapland et al. | |
| 5,871,449 A | 2/1999 | Brown | |
| 5,891,181 A | 4/1999 | Zhu | |
| 5,893,885 A | 4/1999 | Webster et al. | |
| 5,902,242 A * | 5/1999 | Ustuner et al. | 600/443 |
| 5,906,636 A | 5/1999 | Casscells, III et al. | |
| 5,906,817 A | 5/1999 | Moullier et al. | |
| 5,913,876 A | 6/1999 | Taylor et al. | |
| 5,916,154 A | 6/1999 | Hobbs et al. | |
| 5,916,239 A | 6/1999 | Geddes et al. | |
| 5,919,187 A | 7/1999 | Guglielmi et al. | |
| 5,924,997 A | 7/1999 | Campbell | |
| 5,928,272 A | 7/1999 | Adkins et al. | |
| 5,935,075 A | 8/1999 | Casscells et al. | |
| 5,944,710 A | 8/1999 | Dev et al. | |
| 5,954,719 A | 9/1999 | Chen et al. | |
| 5,983,131 A | 11/1999 | Weaver et al. | |
| 5,983,141 A | 11/1999 | Sluijter et al. | |
| 6,006,134 A | 12/1999 | Hill et al. | |
| 6,009,877 A | 1/2000 | Edwards | |
| 6,010,613 A | 1/2000 | Walters et al. | |
| 6,026,326 A | 2/2000 | Bardy | |
| 6,041,252 A | 3/2000 | Walker et al. | |
| 6,051,017 A | 4/2000 | Loeb et al. | |
| 6,058,328 A | 5/2000 | Levine et al. | |
| 6,058,331 A | 5/2000 | King | |
| 6,066,134 A | 5/2000 | Eggers et al. | |
| 6,073,048 A | 6/2000 | Kieval et al. | |
| 6,077,227 A | 6/2000 | Miesel et al. | |
| 6,086,527 A | 7/2000 | Talpade | |
| 6,117,101 A | 9/2000 | Diederich et al. | |
| 6,122,548 A | 9/2000 | Starkebaum et al. | |
| 6,123,718 A | 9/2000 | Tu et al. | |
| 6,135,999 A | 10/2000 | Fanton et al. | |
| 6,146,380 A | 11/2000 | Racz et al. | |
| 6,149,596 A | 11/2000 | Bancroft | |
| 6,161,048 A | 12/2000 | Sluijter et al. | |
| 6,171,306 B1 | 1/2001 | Swanson | |
| 6,178,349 B1 | 1/2001 | Kieval | |
| 6,190,353 B1 | 2/2001 | Makower et al. | |
| 6,192,889 B1 | 2/2001 | Morrish | |
| 6,205,361 B1 | 3/2001 | Kuzma et al. | |
| 6,208,894 B1 | 3/2001 | Schulman et al. | |
| 6,210,356 B1 | 4/2001 | Anderson et al. | |
| 6,214,032 B1 | 4/2001 | Loeb et al. | |
| 6,216,704 B1 * | 4/2001 | Ingle et al. | 128/898 |
| 6,219,577 B1 | 4/2001 | Brown, III et al. | |
| 6,224,592 B1 | 5/2001 | Eggers et al. | |
| 6,238,702 B1 | 5/2001 | Berde et al. | |
| 6,245,026 B1 | 6/2001 | Campbell et al. | |
| 6,246,912 B1 | 6/2001 | Sluijter | |
| 6,251,130 B1 | 6/2001 | Dobak, III et al. | |
| 6,254,598 B1 * | 7/2001 | Edwards et al. | 606/41 |
| 6,258,087 B1 | 7/2001 | Edwards et al. | |
| 6,259,952 B1 | 7/2001 | Sluijter et al. | |
| 6,269,269 B1 | 7/2001 | Ottenhoff et al. | |
| 6,272,377 B1 | 8/2001 | Sweeney et al. | |
| 6,272,383 B1 | 8/2001 | Grey et al. | |
| 6,273,886 B1 | 8/2001 | Edwards | |
| 6,280,377 B1 | 8/2001 | Talpade | |
| 6,283,951 B1 | 9/2001 | Flaherty et al. | |
| 6,283,987 B1 * | 9/2001 | Laird et al. | 607/96 |
| 6,287,304 B1 | 9/2001 | Eggers et al. | |
| 6,287,608 B1 | 9/2001 | Levin et al. | |
| 6,292,695 B1 | 9/2001 | Webster, Jr. et al. | |
| 6,304,777 B1 | 10/2001 | Ben-Haim et al. | |
| 6,304,787 B1 | 10/2001 | Kuzma et al. | |
| 6,306,423 B1 | 10/2001 | Donovan et al. | |
| 6,314,325 B1 | 11/2001 | Fitz | |
| 6,322,558 B1 | 11/2001 | Taylor et al. | |
| 6,322,559 B1 | 11/2001 | Daulton et al. | |
| 6,326,020 B1 | 12/2001 | Kohane et al. | |
| 6,326,177 B1 | 12/2001 | Schoenbach et al. | |
| 6,328,699 B1 | 12/2001 | Eigler et al. | |
| 6,334,069 B1 | 12/2001 | George et al. | |
| 6,347,247 B1 | 2/2002 | Dev et al. | |
| 6,353,763 B1 | 3/2002 | George et al. | |
| 6,356,786 B1 | 3/2002 | Rezai et al. | |
| 6,356,787 B1 | 3/2002 | Rezai et al. | |
| 6,361,531 B1 | 3/2002 | Hissong | |
| 6,366,808 B1 | 4/2002 | Schroppel et al. | |
| 6,366,815 B1 | 4/2002 | Haugland et al. | |
| 6,393,324 B2 | 5/2002 | Gruzdowich et al. | |
| 6,400,982 B2 | 6/2002 | Sweeney et al. | |
| 6,405,079 B1 | 6/2002 | Ansarinia | |
| 6,405,732 B1 | 6/2002 | Edwards et al. | |
| 6,413,255 B1 | 7/2002 | Stern | |
| 6,415,183 B1 | 7/2002 | Scheiner et al. | |
| 6,415,187 B1 | 7/2002 | Kuzma et al. | |
| 6,438,423 B1 | 8/2002 | Rezai et al. | |
| 6,442,424 B1 | 8/2002 | Ben-Haim et al. | |
| 6,449,507 B1 | 9/2002 | Hill et al. | |
| 6,450,942 B1 | 9/2002 | Lapanashvili et al. | |
| 6,461,314 B1 | 10/2002 | Pant et al. | |
| 6,464,687 B1 | 10/2002 | Ishikawa et al. | |
| 6,473,644 B1 | 10/2002 | Terry, Jr. et al. | |
| 6,480,746 B1 * | 11/2002 | Ingle et al. | 607/99 |
| 6,482,619 B1 | 11/2002 | Rubinsky et al. | |
| 6,488,679 B1 | 12/2002 | Swanson et al. | |
| 6,500,174 B1 | 12/2002 | Maguire et al. | |
| 6,506,189 B1 | 1/2003 | Rittman et al. | |
| 6,508,774 B1 | 1/2003 | Acker et al. | |
| 6,514,226 B1 | 2/2003 | Levin et al. | |
| 6,514,249 B1 * | 2/2003 | Maguire et al. | 606/41 |
| 6,516,211 B1 | 2/2003 | Acker et al. | |
| 6,517,811 B2 | 2/2003 | John et al. | |
| 6,522,926 B1 | 2/2003 | Kieval et al. | |
| 6,522,932 B1 | 2/2003 | Kuzma et al. | |
| 6,524,607 B1 | 2/2003 | Goldenheim et al. | |
| 6,534,081 B2 | 3/2003 | Goldenheim et al. | |
| 6,536,949 B1 | 3/2003 | Heuser | |
| 6,546,934 B1 * | 4/2003 | Ingle et al. | 128/898 |
| 6,547,767 B1 | 4/2003 | Moein | |
| 6,547,788 B1 * | 4/2003 | Maguire et al. | 606/41 |
| 6,564,096 B2 | 5/2003 | Mest | |
| 6,571,127 B1 | 5/2003 | Ben-Haim et al. | |
| 6,592,567 B1 | 7/2003 | Levin et al. | |
| 6,599,256 B1 | 7/2003 | Acker et al. | |
| 6,600,954 B2 | 7/2003 | Cohen et al. | |
| 6,600,956 B2 | 7/2003 | Maschino et al. | |
| 6,601,459 B1 | 8/2003 | Jenni et al. | |
| 6,605,084 B2 | 8/2003 | Acker et al. | |
| 6,613,045 B1 | 9/2003 | Laufer et al. | |
| 6,615,071 B1 | 9/2003 | Casscells, III et al. | |
| 6,616,624 B1 | 9/2003 | Kieval | |
| 6,620,151 B2 | 9/2003 | Blischak et al. | |
| 6,622,041 B2 | 9/2003 | Terry, Jr. et al. | |
| 6,622,731 B2 | 9/2003 | Daniel et al. | |

(56) References Cited

U.S. PATENT DOCUMENTS

| | | | |
|---|---|---|---|
| 6,626,855 B1 | 9/2003 | Weng et al. | |
| 6,629,535 B2 * | 10/2003 | Ingle et al. | 128/898 |
| 6,632,196 B1 | 10/2003 | Houser | |
| 6,635,054 B2 | 10/2003 | Fjield et al. | |
| 6,654,636 B1 | 11/2003 | Dev et al. | |
| 6,656,136 B1 | 12/2003 | Weng et al. | |
| 6,666,845 B2 | 12/2003 | Hooper et al. | |
| 6,669,655 B1 | 12/2003 | Acker et al. | |
| 6,671,556 B2 | 12/2003 | Osorio et al. | |
| 6,672,312 B2 | 1/2004 | Acker | |
| 6,676,657 B2 | 1/2004 | Wood | |
| 6,681,136 B2 | 1/2004 | Schuler et al. | |
| 6,684,105 B2 | 1/2004 | Cohen et al. | |
| 6,690,971 B2 | 2/2004 | Schauerte et al. | |
| 6,692,490 B1 | 2/2004 | Edwards et al. | |
| 6,692,738 B2 | 2/2004 | MacLaughlin et al. | |
| 6,697,670 B2 | 2/2004 | Chornenky et al. | |
| 6,699,231 B1 | 3/2004 | Sterman et al. | |
| 6,718,208 B2 | 4/2004 | Hill et al. | |
| 6,719,694 B2 | 4/2004 | Weng et al. | |
| 6,735,471 B2 | 5/2004 | Hill et al. | |
| 6,738,663 B2 | 5/2004 | Schroppel et al. | |
| 6,749,598 B1 | 6/2004 | Keren et al. | |
| 6,767,544 B2 | 7/2004 | Brooks et al. | |
| 6,780,183 B2 | 8/2004 | Jimenez, Jr. et al. | |
| 6,786,904 B2 | 9/2004 | Doscher et al. | |
| 6,793,722 B2 | 9/2004 | Chien et al. | |
| 6,795,728 B2 | 9/2004 | Chornenky et al. | |
| 6,814,730 B2 | 11/2004 | Li | |
| 6,845,267 B2 | 1/2005 | Harrison et al. | |
| 6,850,801 B2 | 2/2005 | Kieval et al. | |
| 6,862,479 B1 | 3/2005 | Whitehurst et al. | |
| 6,865,416 B2 | 3/2005 | Dev et al. | |
| 6,866,662 B2 | 3/2005 | Fuimaono et al. | |
| 6,869,431 B2 | 3/2005 | Maguire et al. | |
| 6,885,888 B2 | 4/2005 | Rezai | |
| 6,916,656 B2 | 7/2005 | Walters et al. | |
| 6,927,049 B2 | 8/2005 | Rubinsky et al. | |
| 6,936,047 B2 | 8/2005 | Nasab et al. | |
| 6,939,345 B2 | 9/2005 | KenKnight et al. | |
| 6,939,346 B2 | 9/2005 | Kannenberg et al. | |
| 6,953,460 B2 | 10/2005 | Maguire et al. | |
| 6,954,977 B2 * | 10/2005 | Maguire et al. | 29/460 |
| 6,958,060 B2 | 10/2005 | Mathiesen et al. | |
| 6,969,388 B2 | 11/2005 | Goldman et al. | |
| 6,972,013 B1 | 12/2005 | Zhang et al. | |
| 6,976,492 B2 * | 12/2005 | Ingle et al. | 128/898 |
| 6,978,174 B2 | 12/2005 | Gelfand et al. | |
| 6,985,774 B2 | 1/2006 | Kieval et al. | |
| 6,994,700 B2 | 2/2006 | Elkins et al. | |
| 6,994,706 B2 | 2/2006 | Chornenky et al. | |
| 7,004,911 B1 | 2/2006 | Tu et al. | |
| 7,054,685 B2 | 5/2006 | Dimmer et al. | |
| 7,063,666 B2 | 6/2006 | Weng et al. | |
| 7,063,679 B2 | 6/2006 | Maguire et al. | |
| 7,081,114 B2 | 7/2006 | Rashidi | |
| 7,081,115 B2 | 7/2006 | Taimisto | |
| 7,083,614 B2 | 8/2006 | Fjield et al. | |
| 7,122,019 B1 | 10/2006 | Kesten et al. | |
| 7,155,284 B1 | 12/2006 | Whitehurst et al. | |
| 7,162,303 B2 | 1/2007 | Levin et al. | |
| 7,191,015 B2 | 3/2007 | Lamson et al. | |
| 7,373,204 B2 | 5/2008 | Gelfand et al. | |
| 7,381,200 B2 | 6/2008 | Katoh et al. | |
| 7,444,183 B2 | 10/2008 | Knudson et al. | |
| 7,470,241 B2 | 12/2008 | Weng et al. | |
| 7,510,536 B2 | 3/2009 | Foley et al. | |
| 7,540,846 B2 | 6/2009 | Harhen et al. | |
| 7,615,015 B2 | 11/2009 | Coleman | |
| 7,617,005 B2 | 11/2009 | Demarais et al. | |
| 7,620,451 B2 | 11/2009 | Demarais et al. | |
| 7,647,115 B2 | 1/2010 | Levin et al. | |
| 7,653,438 B2 | 1/2010 | Deem et al. | |
| 7,655,005 B2 | 2/2010 | Bhola | |
| 7,674,259 B2 | 3/2010 | Shadduck et al. | |
| 7,717,948 B2 | 5/2010 | Demarais et al. | |
| 7,756,583 B2 | 7/2010 | Demarais et al. | |
| 7,837,676 B2 | 11/2010 | Sinelnikov et al. | |
| 7,942,871 B2 | 5/2011 | Thapliyal et al. | |
| 7,950,397 B2 | 5/2011 | Thapliyal et al. | |
| 8,131,371 B2 | 3/2012 | Demarals et al. | |
| 8,131,372 B2 | 3/2012 | Levin et al. | |
| 8,137,274 B2 | 3/2012 | Weng et al. | |
| 8,145,316 B2 | 3/2012 | Deem et al. | |
| 8,145,317 B2 | 3/2012 | Demarais et al. | |
| 8,146,603 B2 | 4/2012 | Thapliyal et al. | |
| 8,150,518 B2 | 4/2012 | Levin et al. | |
| 8,150,519 B2 | 4/2012 | Demarais et al. | |
| 8,150,520 B2 | 4/2012 | Demarais et al. | |
| 8,167,805 B2 | 5/2012 | Emery et al. | |
| 8,175,711 B2 | 5/2012 | Demarais et al. | |
| 8,295,912 B2 | 10/2012 | Gertner | |
| 8,469,904 B2 | 6/2013 | Gertner | |
| 8,512,262 B2 | 8/2013 | Gertner | |
| 8,556,834 B2 | 10/2013 | Gertner | |
| 8,585,597 B2 | 11/2013 | Dae et al. | |
| 2001/0014819 A1 * | 8/2001 | Ingle et al. | 607/99 |
| 2001/0018606 A1 * | 8/2001 | Ingle et al. | 607/116 |
| 2001/0044596 A1 | 11/2001 | Jaafar | |
| 2002/0002329 A1 | 1/2002 | Avitall | |
| 2002/0002349 A1 | 1/2002 | Flaherty et al. | |
| 2002/0022833 A1 * | 2/2002 | Maguire et al. | 606/27 |
| 2002/0026222 A1 | 2/2002 | Schauerte et al. | |
| 2002/0026228 A1 | 2/2002 | Schauerte | |
| 2002/0032468 A1 | 3/2002 | Hill et al. | |
| 2002/0038137 A1 | 3/2002 | Stein | |
| 2002/0040204 A1 | 4/2002 | Dev et al. | |
| 2002/0045853 A1 | 4/2002 | Dev et al. | |
| 2002/0065541 A1 | 5/2002 | Fredricks et al. | |
| 2002/0072782 A1 | 6/2002 | Osorio et al. | |
| 2002/0087156 A1 | 7/2002 | Maguire et al. | |
| 2002/0107553 A1 | 8/2002 | Hill et al. | |
| 2002/0116030 A1 | 8/2002 | Rezai | |
| 2002/0120304 A1 | 8/2002 | Mest | |
| 2002/0165532 A1 | 11/2002 | Hill et al. | |
| 2002/0165535 A1 * | 11/2002 | Lesh et al. | 606/41 |
| 2002/0165586 A1 | 11/2002 | Hill et al. | |
| 2002/0169413 A1 | 11/2002 | Keren et al. | |
| 2002/0177846 A1 | 11/2002 | Mulier et al. | |
| 2002/0183682 A1 | 12/2002 | Darvish | |
| 2002/0183684 A1 | 12/2002 | Dev et al. | |
| 2002/0188325 A1 | 12/2002 | Hill et al. | |
| 2002/0198512 A1 | 12/2002 | Seward | |
| 2002/0198521 A1 * | 12/2002 | Maguire | 606/41 |
| 2003/0004549 A1 | 1/2003 | Hill et al. | |
| 2003/0009145 A1 | 1/2003 | Struijker-Boudier et al. | |
| 2003/0013960 A1 * | 1/2003 | Makin et al. | 600/439 |
| 2003/0013971 A1 | 1/2003 | Makin et al. | |
| 2003/0018367 A1 | 1/2003 | DiLorenzo | |
| 2003/0040774 A1 | 2/2003 | Terry, Jr. et al. | |
| 2003/0045909 A1 | 3/2003 | Gross et al. | |
| 2003/0050681 A1 | 3/2003 | Pianca | |
| 2003/0060848 A1 | 3/2003 | Kieval et al. | |
| 2003/0060857 A1 | 3/2003 | Perrson et al. | |
| 2003/0060858 A1 | 3/2003 | Kieval et al. | |
| 2003/0069620 A1 * | 4/2003 | Li | 607/101 |
| 2003/0082225 A1 | 5/2003 | Mason | |
| 2003/0083653 A1 | 5/2003 | Maguire et al. | |
| 2003/0100924 A1 | 5/2003 | Foreman et al. | |
| 2003/0120270 A1 | 6/2003 | Acker | |
| 2003/0125790 A1 | 7/2003 | Fastovsky | |
| 2003/0139790 A1 * | 7/2003 | Ingle et al. | 607/99 |
| 2003/0150464 A1 | 8/2003 | Casscells | |
| 2003/0158584 A1 | 8/2003 | Cates et al. | |
| 2003/0176816 A1 * | 9/2003 | Maguire et al. | 601/2 |
| 2003/0178032 A1 * | 9/2003 | Ingle et al. | 128/898 |
| 2003/0181081 A1 | 9/2003 | Thomas et al. | |
| 2003/0181963 A1 | 9/2003 | Pellegrino et al. | |
| 2003/0195496 A1 | 10/2003 | Maguire et al. | |
| 2003/0195510 A1 * | 10/2003 | Schaer | 606/41 |
| 2003/0199747 A1 | 10/2003 | Michlitsch et al. | |
| 2003/0199767 A1 | 10/2003 | Cespedes et al. | |
| 2003/0199768 A1 | 10/2003 | Cespedes et al. | |
| 2003/0199806 A1 | 10/2003 | Kieval | |

(56) References Cited

U.S. PATENT DOCUMENTS

| | | |
|---|---|---|
| 2003/0199863 A1 | 10/2003 | Swanson et al. |
| 2003/0204161 A1 | 10/2003 | Ferek-Petric |
| 2003/0216721 A1 | 11/2003 | Diederich et al. |
| 2003/0216792 A1 | 11/2003 | Levin et al. |
| 2003/0220521 A1 | 11/2003 | Reitz et al. |
| 2003/0236443 A1 | 12/2003 | Cespedes et al. |
| 2004/0010289 A1 | 1/2004 | Biggs et al. |
| 2004/0010303 A1 | 1/2004 | Bolea et al. |
| 2004/0019349 A1 | 1/2004 | Fuimaono et al. |
| 2004/0019364 A1 | 1/2004 | Kieval et al. |
| 2004/0019371 A1 | 1/2004 | Jaafar et al. |
| 2004/0054367 A1 | 3/2004 | Jimenez et al. |
| 2004/0064090 A1 | 4/2004 | Keren et al. |
| 2004/0064091 A1 | 4/2004 | Keren et al. |
| 2004/0065615 A1 | 4/2004 | Hooper et al. |
| 2004/0068186 A1* | 4/2004 | Ishida et al. ............ 600/439 |
| 2004/0073238 A1 | 4/2004 | Makower |
| 2004/0082978 A1 | 4/2004 | Harrison et al. |
| 2004/0101523 A1 | 5/2004 | Reitz et al. |
| 2004/0106880 A1 | 6/2004 | Weng et al. |
| 2004/0106953 A1 | 6/2004 | Yomtov et al. |
| 2004/0111080 A1 | 6/2004 | Harper et al. |
| 2004/0127942 A1 | 7/2004 | Yomtov et al. |
| 2004/0158143 A1 | 8/2004 | Flaherty |
| 2004/0162590 A1 | 8/2004 | Whitehurst et al. |
| 2004/0163655 A1 | 8/2004 | Gelfand et al. |
| 2004/0167415 A1 | 8/2004 | Gelfand et al. |
| 2004/0176699 A1 | 9/2004 | Walker et al. |
| 2004/0176757 A1 | 9/2004 | Sinelnikov et al. |
| 2004/0181178 A1 | 9/2004 | Aldrich et al. |
| 2004/0193228 A1 | 9/2004 | Gerber |
| 2004/0215186 A1 | 10/2004 | Cornelius et al. |
| 2004/0220511 A1 | 11/2004 | Scott et al. |
| 2004/0243102 A1 | 12/2004 | Berg et al. |
| 2004/0243206 A1 | 12/2004 | Tadlock |
| 2004/0249416 A1 | 12/2004 | Yun et al. |
| 2004/0254616 A1 | 12/2004 | Rossing et al. |
| 2004/0260277 A1 | 12/2004 | Maguire |
| 2005/0004522 A1 | 1/2005 | Katoh et al. |
| 2005/0010263 A1 | 1/2005 | Schauerte |
| 2005/0021092 A1 | 1/2005 | Yun et al. |
| 2005/0038409 A1 | 2/2005 | Segal et al. |
| 2005/0049542 A1 | 3/2005 | Sigg et al. |
| 2005/0065562 A1 | 3/2005 | Rezai |
| 2005/0065573 A1 | 3/2005 | Rezai |
| 2005/0065574 A1 | 3/2005 | Rezai |
| 2005/0075681 A1 | 4/2005 | Rezai et al. |
| 2005/0080409 A1 | 4/2005 | Young et al. |
| 2005/0080459 A1 | 4/2005 | Jacobson et al. |
| 2005/0096710 A1 | 5/2005 | Kieval |
| 2005/0113822 A1 | 5/2005 | Fuimaono et al. |
| 2005/0153885 A1 | 7/2005 | Yun et al. |
| 2005/0154418 A1 | 7/2005 | Kieval et al. |
| 2005/0165388 A1 | 7/2005 | Bhola |
| 2005/0171523 A1 | 8/2005 | Rubinsky et al. |
| 2005/0171574 A1 | 8/2005 | Rubinsky et al. |
| 2005/0171575 A1 | 8/2005 | Dev et al. |
| 2005/0187579 A1 | 8/2005 | Danek et al. |
| 2005/0197624 A1 | 9/2005 | Goodson et al. |
| 2005/0203399 A1* | 9/2005 | Vaezy et al. ............ 600/439 |
| 2005/0209548 A1 | 9/2005 | Dev et al. |
| 2005/0209642 A1 | 9/2005 | Palti |
| 2005/0228460 A1 | 10/2005 | Levin et al. |
| 2005/0234437 A1 | 10/2005 | Baxter et al. |
| 2005/0234523 A1 | 10/2005 | Levin et al. |
| 2005/0240126 A1 | 10/2005 | Foley et al. |
| 2005/0240170 A1 | 10/2005 | Zhang et al. |
| 2005/0240173 A1 | 10/2005 | Palti |
| 2005/0240228 A1 | 10/2005 | Palti |
| 2005/0240241 A1 | 10/2005 | Yun et al. |
| 2005/0245882 A1 | 11/2005 | Elkins et al. |
| 2005/0245892 A1 | 11/2005 | Elkins et al. |
| 2005/0251212 A1 | 11/2005 | Kieval et al. |
| 2005/0261672 A1 | 11/2005 | Deem et al. |
| 2005/0267010 A1 | 12/2005 | Goodson et al. |
| 2005/0282284 A1 | 12/2005 | Rubinsky et al. |
| 2005/0288730 A1 | 12/2005 | Deem et al. |
| 2006/0004417 A1 | 1/2006 | Rossing et al. |
| 2006/0004430 A1 | 1/2006 | Rossing et al. |
| 2006/0025821 A1 | 2/2006 | Gelfand et al. |
| 2006/0030814 A1 | 2/2006 | Valencia et al. |
| 2006/0036218 A1 | 2/2006 | Goodson et al. |
| 2006/0041277 A1 | 2/2006 | Deem et al. |
| 2006/0041283 A1 | 2/2006 | Gelfand et al. |
| 2006/0058678 A1 | 3/2006 | Vitek et al. |
| 2006/0058711 A1 | 3/2006 | Harhen et al. |
| 2006/0067972 A1 | 3/2006 | Kesten et al. |
| 2006/0069323 A1 | 3/2006 | Elkins et al. |
| 2006/0074453 A1 | 4/2006 | Kieval et al. |
| 2006/0079859 A1 | 4/2006 | Elkins et al. |
| 2006/0084966 A1 | 4/2006 | Maguire et al. |
| 2006/0085046 A1 | 4/2006 | Rezai et al. |
| 2006/0089674 A1 | 4/2006 | Walters et al. |
| 2006/0095029 A1 | 5/2006 | Young et al. |
| 2006/0100667 A1 | 5/2006 | Machado et al. |
| 2006/0106429 A1 | 5/2006 | Libbus et al. |
| 2006/0111754 A1 | 5/2006 | Rezai et al. |
| 2006/0116720 A1 | 6/2006 | Knoblich |
| 2006/0121016 A1 | 6/2006 | Lee |
| 2006/0121610 A1 | 6/2006 | Rubinsky et al. |
| 2006/0135998 A1 | 6/2006 | Libbus et al. |
| 2006/0136004 A1 | 6/2006 | Cowan et al. |
| 2006/0149350 A1 | 7/2006 | Patel et al. |
| 2006/0155344 A1 | 7/2006 | Rezai et al. |
| 2006/0167437 A1 | 7/2006 | Valencia |
| 2006/0167498 A1 | 7/2006 | DiLorenzo |
| 2006/0167499 A1 | 7/2006 | Palti |
| 2006/0189941 A1 | 8/2006 | Seward et al. |
| 2006/0189960 A1 | 8/2006 | Kesten et al. |
| 2006/0190044 A1 | 8/2006 | Libbus et al. |
| 2006/0206149 A1 | 9/2006 | Yun |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0229677 A1 | 10/2006 | Moffitt et al. |
| 2006/0235300 A1* | 10/2006 | Weng et al. ............ 600/439 |
| 2006/0235474 A1 | 10/2006 | Demarais |
| 2006/0241442 A1* | 10/2006 | Barthe et al. ............ 600/439 |
| 2006/0265014 A1 | 11/2006 | Demarais et al. |
| 2006/0265015 A1 | 11/2006 | Demarais et al. |
| 2006/0271111 A1 | 11/2006 | Demarais et al. |
| 2006/0276852 A1 | 12/2006 | Demarais et al. |
| 2007/0038056 A1 | 2/2007 | Pappone et al. |
| 2007/0038099 A1* | 2/2007 | Sugita et al. ............ 600/439 |
| 2007/0066897 A1 | 3/2007 | Sekins et al. |
| 2007/0066957 A1 | 3/2007 | Demarais et al. |
| 2007/0066972 A1 | 3/2007 | Ormsby et al. |
| 2007/0083239 A1 | 4/2007 | Demarais et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0142864 A1 | 6/2007 | Libbus et al. |
| 2007/0156200 A1 | 7/2007 | Kornet et al. |
| 2007/0167773 A1* | 7/2007 | Jeong et al. ............ 600/439 |
| 2007/0173899 A1 | 7/2007 | Levin et al. |
| 2007/0179558 A1 | 8/2007 | Weng et al. |
| 2007/0208329 A1* | 9/2007 | Ward et al. ............ 606/17 |
| 2007/0208382 A1 | 9/2007 | Yun |
| 2007/0265687 A1 | 11/2007 | Deem et al. |
| 2007/0282376 A1 | 12/2007 | Shuros et al. |
| 2007/0288070 A1 | 12/2007 | Libbus et al. |
| 2008/0004528 A1* | 1/2008 | Fitzsimons et al. ............ 600/439 |
| 2008/0004673 A1 | 1/2008 | Rossing et al. |
| 2008/0015659 A1 | 1/2008 | Zhang et al. |
| 2008/0039904 A1 | 2/2008 | Bulkes et al. |
| 2008/0091255 A1 | 4/2008 | Caparso et al. |
| 2008/0140150 A1 | 6/2008 | Zhou et al. |
| 2008/0195085 A1* | 8/2008 | Loeb ............ 606/3 |
| 2008/0213331 A1 | 9/2008 | Gelfand et al. |
| 2008/0249419 A1 | 10/2008 | Sekins et al. |
| 2008/0255478 A1 | 10/2008 | Burdette |
| 2008/0255642 A1 | 10/2008 | Zarins et al. |
| 2008/0319513 A1 | 12/2008 | Pu et al. |

(56) References Cited

U.S. PATENT DOCUMENTS

| | | |
|---|---|---|
| 2009/0024195 A1 | 1/2009 | Rezai et al. |
| 2009/0036774 A1 | 2/2009 | Weng et al. |
| 2009/0036948 A1 | 2/2009 | Levin et al. |
| 2009/0062697 A1 | 3/2009 | Zhang et al. |
| 2009/0062873 A1 | 3/2009 | Wu et al. |
| 2009/0076409 A1 | 3/2009 | Wu et al. |
| 2009/0157066 A1* | 6/2009 | Satake ................. 606/27 |
| 2009/0253988 A1* | 10/2009 | Slayton et al. ............ 600/439 |
| 2009/0312673 A1 | 12/2009 | Thapliyal et al. |
| 2009/0312693 A1 | 12/2009 | Thapliyal et al. |
| 2009/0312755 A1 | 12/2009 | Thapliyal et al. |
| 2010/0010567 A1 | 1/2010 | Deem et al. |
| 2010/0016762 A1 | 1/2010 | Thapliyal et al. |
| 2010/0049099 A1 | 2/2010 | Thapliyal et al. |
| 2010/0057150 A1 | 3/2010 | Demarais et al. |
| 2010/0113928 A1 | 5/2010 | Thapliyal et al. |
| 2010/0113985 A1 | 5/2010 | Thapliyal et al. |
| 2010/0114094 A1 | 5/2010 | Thapliyal et al. |
| 2010/0125198 A1 | 5/2010 | Thapliyal et al. |
| 2010/0130892 A1 | 5/2010 | Warnking |
| 2010/0137860 A1 | 6/2010 | Demarais et al. |
| 2010/0137952 A1 | 6/2010 | Demarais et al. |
| 2010/0152582 A1 | 6/2010 | Thapliyal et al. |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0179424 A1 | 7/2010 | Warnking |
| 2010/0191112 A1 | 7/2010 | Demarais et al. |
| 2010/0198065 A1 | 8/2010 | Thapliyal et al. |
| 2010/0204577 A1 | 8/2010 | Sekins et al. |
| 2010/0222851 A1 | 9/2010 | Deem et al. |
| 2010/0222854 A1 | 9/2010 | Demarais et al. |
| 2010/0249773 A1 | 9/2010 | Clark et al. |
| 2010/0268307 A1 | 10/2010 | Demarais et al. |
| 2011/0021913 A1 | 1/2011 | Weng et al. |
| 2011/0040184 A1* | 2/2011 | Mast et al. ............... 600/443 |
| 2011/0066085 A1 | 3/2011 | Weng et al. |
| 2011/0092781 A1 | 4/2011 | Gertner |
| 2011/0092880 A1 | 4/2011 | Gertner |
| 2011/0112400 A1 | 5/2011 | Emery et al. |
| 2011/0118598 A1 | 5/2011 | Gertner |
| 2011/0118600 A1 | 5/2011 | Gertner |
| 2011/0118632 A1 | 5/2011 | Sinelnikov et al. |
| 2011/0137149 A1 | 6/2011 | Gertner |
| 2011/0137298 A1 | 6/2011 | Nguyen et al. |
| 2011/0172527 A1 | 7/2011 | Gertner |
| 2011/0172528 A1 | 7/2011 | Gertner |
| 2011/0172529 A1 | 7/2011 | Gertner |
| 2011/0172654 A1* | 7/2011 | Barry et al. .............. 606/27 |
| 2011/0208096 A1 | 8/2011 | Demarais et al. |
| 2011/0257523 A1 | 10/2011 | Hastings et al. |
| 2011/0257561 A1 | 10/2011 | Gertner et al. |
| 2011/0257562 A1 | 10/2011 | Schaer |
| 2011/0257563 A1 | 10/2011 | Thapliyal et al. |
| 2011/0257564 A1 | 10/2011 | Demarais et al. |
| 2011/0319765 A1 | 12/2011 | Gertner et al. |
| 2012/0010902 A1 | 1/2012 | Goldberg |
| 2012/0016226 A1 | 1/2012 | Gertner |
| 2012/0022409 A1 | 1/2012 | Gertner et al. |
| 2012/0059286 A1 | 3/2012 | Hastings et al. |
| 2012/0065492 A1 | 3/2012 | Gertner et al. |
| 2012/0065493 A1 | 3/2012 | Gertner |
| 2012/0065494 A1 | 3/2012 | Gertner et al. |
| 2012/0095335 A1 | 4/2012 | Sverdlik et al. |
| 2012/0095371 A1 | 4/2012 | Sverdlik et al. |
| 2012/0101413 A1* | 4/2012 | Beetel et al. .............. 601/3 |
| 2012/0109018 A1 | 5/2012 | Gertner et al. |
| 2012/0109023 A1 | 5/2012 | Emery et al. |
| 2012/0123243 A1 | 5/2012 | Hastings |
| 2012/0123261 A1 | 5/2012 | Jenson et al. |
| 2012/0123303 A1 | 5/2012 | Sogard et al. |
| 2012/0143078 A1 | 6/2012 | Kassab et al. |
| 2012/0143097 A1 | 6/2012 | Pike, Jr. |
| 2012/0157984 A1 | 6/2012 | Thapliyal et al. |
| 2012/0172723 A1 | 7/2012 | Gertner |
| 2012/0172837 A1 | 7/2012 | Demarais et al. |
| 2012/0197166 A1 | 8/2012 | Gertner |
| 2012/0209118 A1 | 8/2012 | Warnking |
| 2012/0209261 A1 | 8/2012 | Mayse et al. |
| 2012/0232409 A1 | 9/2012 | Stahmann et al. |
| 2012/0232436 A1 | 9/2012 | Warnking |
| 2012/0238918 A1 | 9/2012 | Gertner |
| 2012/0238919 A1 | 9/2012 | Gertner |
| 2012/0245494 A1 | 9/2012 | Gertner |
| 2012/0253239 A1 | 10/2012 | Gertner et al. |
| 2012/0265227 A1 | 10/2012 | Sverdlik et al. |
| 2012/0271171 A1 | 10/2012 | Gertner |
| 2013/0006232 A1 | 1/2013 | Pellegrino et al. |
| 2013/0012844 A1 | 1/2013 | Demarais et al. |
| 2013/0023862 A1 | 1/2013 | Marrouche et al. |
| 2013/0060141 A1* | 3/2013 | Sinelnikov .............. 600/439 |
| 2013/0074661 A1 | 3/2013 | Chang |
| 2013/0090578 A1 | 4/2013 | Smith et al. |
| 2013/0110012 A1 | 5/2013 | Gertner |
| 2013/0123625 A1 | 5/2013 | Hastings et al. |
| 2013/0123670 A1 | 5/2013 | Smith |
| 2013/0123770 A1* | 5/2013 | Smith ................. 606/28 |
| 2013/0131668 A1* | 5/2013 | Schaer ................. 606/41 |
| 2013/0138018 A1 | 5/2013 | Gertner |
| 2013/0138095 A1 | 5/2013 | Gertner |
| 2013/0158441 A1 | 6/2013 | Demarais et al. |
| 2013/0158442 A1 | 6/2013 | Demarais et al. |
| 2013/0165822 A1 | 6/2013 | Demarais et al. |
| 2013/0184703 A1 | 7/2013 | Shireman et al. |
| 2013/0190716 A1 | 7/2013 | Gertner |
| 2013/0190748 A1 | 7/2013 | Coe et al. |
| 2013/0197555 A1 | 8/2013 | Schaer |
| 2013/0204167 A1 | 8/2013 | Sverdlik et al. |
| 2013/0211292 A1 | 8/2013 | Sverdlik et al. |
| 2013/0211396 A1 | 8/2013 | Sverdlik et al. |
| 2013/0211437 A1 | 8/2013 | Sverdlik et al. |
| 2013/0218054 A1 | 8/2013 | Sverdlik et al. |
| 2013/0218068 A1 | 8/2013 | Sverdlik et al. |
| 2013/0225973 A1 | 8/2013 | Gertner |
| 2013/0253381 A1 | 9/2013 | Gertner |
| 2013/0281889 A1 | 10/2013 | Gertner |
| 2013/0296646 A1 | 11/2013 | Barbut et al. |
| 2013/0331739 A1 | 12/2013 | Gertner |
| 2014/0012133 A1 | 1/2014 | Sverdlik et al. |
| 2014/0031727 A1 | 1/2014 | Warnking |
| 2014/0039477 A1 | 2/2014 | Sverdlik et al. |
| 2014/0039479 A1 | 2/2014 | Gertner |
| 2014/0046313 A1 | 2/2014 | Pederson et al. |
| 2014/0058188 A1 | 2/2014 | Gertner |
| 2014/0058293 A1 | 2/2014 | Hynynen et al. |
| 2014/0058294 A1 | 2/2014 | Gross et al. |
| 2014/0066883 A1 | 3/2014 | Azamian et al. |
| 2014/0066916 A1 | 3/2014 | Coe et al. |
| 2014/0066919 A1 | 3/2014 | Azamian et al. |
| 2014/0066920 A1 | 3/2014 | Azamian et al. |
| 2014/0066921 A1 | 3/2014 | Coe et al. |
| 2014/0066922 A1 | 3/2014 | Coe et al. |
| 2014/0066923 A1 | 3/2014 | Azamian et al. |
| 2014/0066924 A1 | 3/2014 | Azamian et al. |
| 2014/0074089 A1 | 3/2014 | Nishii |
| 2014/0135715 A1 | 5/2014 | Lambert et al. |

FOREIGN PATENT DOCUMENTS

| | | |
|---|---|---|
| EP | 0811395 | 6/1997 |
| EP | 1299035 | 4/2003 |
| EP | 1299038 | 4/2003 |
| EP | 1596746 | 11/2005 |
| EP | 1265674 | 9/2008 |
| EP | 2018129 | 1/2009 |
| EP | 2092957 | 8/2009 |
| EP | 2218479 | 8/2010 |
| EP | 2275174 | 1/2011 |
| EP | 2275175 | 1/2011 |
| EP | 2285304 | 2/2011 |
| EP | 2285334 | 2/2011 |
| EP | 2296573 | 3/2011 |
| EP | 2307098 | 4/2011 |
| EP | 2309939 | 4/2011 |

(56) References Cited

FOREIGN PATENT DOCUMENTS

| | | |
|---|---|---|
| EP | 2344039 | 7/2011 |
| EP | 2352559 | 8/2011 |
| EP | 2430996 | 3/2012 |
| EP | 2430997 | 3/2012 |
| EP | 2430998 | 3/2012 |
| EP | 2455015 | 5/2012 |
| EP | 2488250 | 8/2012 |
| EP | 2493568 | 9/2012 |
| EP | 2493569 | 9/2012 |
| EP | 2521593 | 11/2012 |
| EP | 2540246 | 1/2013 |
| EP | 2540347 | 1/2013 |
| EP | 2540348 | 1/2013 |
| EP | 2558165 | 2/2013 |
| EP | 2613724 | 7/2013 |
| EP | 2640300 | 9/2013 |
| EP | 2670315 | 12/2013 |
| EP | 2675525 | 12/2013 |
| WO | WO/93/07803 | 4/1933 |
| WO | WO/85/01213 | 3/1985 |
| WO | WO/91/04725 | 4/1991 |
| WO | WO/92/20291 | 11/1992 |
| WO | WO/93/02740 | 2/1993 |
| WO | WO/94/00188 | 1/1994 |
| WO | WO/94/11057 | 5/1994 |
| WO | WO/95/25472 | 9/1995 |
| WO | WO/95/33514 | 12/1995 |
| WO | WO/96/00039 | 1/1996 |
| WO | WO/96/04957 | 2/1996 |
| WO | WO/96/11723 | 4/1996 |
| WO | WO/97/13463 | 4/1997 |
| WO | WO/97/13550 | 4/1997 |
| WO | WO-9736548 | 10/1997 |
| WO | WO/97/49453 | 12/1997 |
| WO | WO/98/37926 | 9/1998 |
| WO | WO/98/42403 | 10/1998 |
| WO | WO/98/43700 | 10/1998 |
| WO | WO/98/43701 | 10/1998 |
| WO | WO/98/48888 | 11/1998 |
| WO | WO-9902096 | 1/1999 |
| WO | WO/99/33407 | 7/1999 |
| WO | WO/99/51286 | 10/1999 |
| WO | WO/99/52424 | 10/1999 |
| WO | WO-0056237 | 9/2000 |
| WO | WO-0122897 | 4/2001 |
| WO | WO0126729 | 4/2001 |
| WO | WO0170114 | 9/2001 |
| WO | WO-0170114 | 9/2001 |
| WO | WO/02/09808 | 2/2002 |
| WO | WO/02/26314 | 4/2002 |
| WO | WO/02/053207 | 7/2002 |
| WO | WO/02/070039 | 9/2002 |
| WO | WO/02/070047 | 9/2002 |
| WO | WO/02/085448 | 10/2002 |
| WO | WO /02085192 | 10/2002 |
| WO | WO/03/018108 | 3/2003 |
| WO | WO/03/028802 | 4/2003 |
| WO | WO/03/063692 | 8/2003 |
| WO | WO/03/071140 | 8/2003 |
| WO | WO/03/076008 | 9/2003 |
| WO | WO/03/082080 | 10/2003 |
| WO | WO/03/082403 | 10/2003 |
| WO | WO/2004/026370 | 4/2004 |
| WO | WO/2004/026371 | 4/2004 |
| WO | WO/2004/026374 | 4/2004 |
| WO | WO/2004/030718 | 4/2004 |
| WO | WO/2004/032791 | 4/2004 |
| WO | WO/2004/107965 | 12/2004 |
| WO | WO/2005/014100 | 2/2005 |
| WO | WO/2005/016165 | 2/2005 |
| WO | WO/2005/032646 | 4/2005 |
| WO | WO-2005/041748 A2 | 5/2005 |
| WO | WO/2005/065284 | 7/2005 |
| WO | WO/2005/084389 | 9/2005 |
| WO | WO/2005/097256 | 10/2005 |
| WO | WO/2005/110528 | 11/2005 |
| WO | WO-2005110528 | 11/2005 |
| WO | WO/2005/123183 | 12/2005 |
| WO | WO/2006/007048 | 1/2006 |
| WO | WO/2006/018528 | 2/2006 |
| WO | WO/2006/031899 | 3/2006 |
| WO | WO-2006022790 A1 | 3/2006 |
| WO | WO-2006041847 | 4/2006 |
| WO | WO-2006041881 | 4/2006 |
| WO | WO-2007008954 | 1/2007 |
| WO | WO-2007035537 | 3/2007 |
| WO | WO-2007078997 A2 | 7/2007 |
| WO | WO-2007086965 | 8/2007 |
| WO | WO-2007103879 | 9/2007 |
| WO | WO-2007103881 | 9/2007 |
| WO | WO-2007121309 | 10/2007 |
| WO | WO-2007134258 | 11/2007 |
| WO | WO-2007146834 | 12/2007 |
| WO | WO-2008003058 | 1/2008 |
| WO | WO-2008061150 | 5/2008 |
| WO | WO-2008061152 | 5/2008 |
| WO | WO-2008070413 | 6/2008 |
| WO | WO 2008151001 | 12/2008 |
| WO | WO-2008151001 | 12/2008 |
| WO | WO-2009152379 | 6/2009 |
| WO | WO-2009152354 | 12/2009 |
| WO | WO-2009152467 | 12/2009 |
| WO | WO-2010009472 | 1/2010 |
| WO | WO-2010009473 | 1/2010 |
| WO | WO-2010057211 | 5/2010 |
| WO | WO-2010078175 A1 | 7/2010 |
| WO | WO-2010080886 | 7/2010 |
| WO | WO-2011046879 | 4/2011 |
| WO | WO-2011046880 | 4/2011 |
| WO | WO-2011053757 | 5/2011 |
| WO | WO-2011053772 | 5/2011 |
| WO | WO-2011056514 | 5/2011 |
| WO | WO-2011059792 | 5/2011 |
| WO | WO-2011130531 | 10/2011 |
| WO | WO-2012033860 | 3/2012 |
| WO | WO-2012/052922 | 4/2012 |
| WO | WO-2012/052926 | 4/2012 |
| WO | WO-2012/052927 | 4/2012 |
| WO | WO-2012052921 | 4/2012 |
| WO | WO-2012052924 | 4/2012 |
| WO | WO-2012068354 | 5/2012 |
| WO | WO-2012106492 | 8/2012 |
| WO | WO-2012112165 | 8/2012 |
| WO | WO-2012120495 | 9/2012 |
| WO | WO-2012125172 | 9/2012 |
| WO | WO-2013013156 | 1/2013 |
| WO | WO-2013014583 | 1/2013 |
| WO | WO-2013/055685 | 4/2013 |
| WO | WO-2013074218 | 5/2013 |
| WO | WO-2013111136 | 8/2013 |
| WO | WO-2013116380 | 8/2013 |
| WO | WO-2013157009 | 10/2013 |
| WO | WO-2013157011 | 10/2013 |
| WO | WO-2013165935 | 11/2013 |
| WO | WO2014022777 | 2/2014 |
| WO | WO2014036463 | 3/2014 |

OTHER PUBLICATIONS

U.S. Appl. No. 12/790,639, filed May 28, 2010, Wu et al.
U.S. Appl. No. 12/871,457, filed Aug. 30, 2010, Wu et al.
U.S. Appl. No. 13/007,370, filed Jan. 18, 2011, Gelfand et al.
U.S. Appl. No. 12/996,897, filed Dec. 13, 2010, Demarais.
U.S. Appl. No. 13/009,748, filed Jan. 19, 2011, Beetel et al.
U.S. Appl. No. 12/910,631, filed Oct. 22, 2010, Wu et al.
International Search Report and Written Opinion, PCT/US05/35693, Mailed on Mar. 8, 2006, Applicant: Ardian, Inc., 29 pages.
International Search Report and Written Opinion, PCT/US05/35757, Mailed on Dec. 27, 2006, Applicant: Ardian, Inc., 8 pages.
International Search Report and Written Opinion, PCT/US06/48822, Mailed on Aug. 15, 2008, Applicant: Ardian, Inc., 12 pages.
International Search Report, PCT/US04/38498, Mailed Feb. 18, 2005, Applicant: G & L Consulting, LLC, 4 pages.

(56) References Cited

OTHER PUBLICATIONS

International Search Report and Written Opinion, PCT/US06/36120, Mailed on Jun. 25, 2008, Applicant: Ardian, Inc., 10 pages.
International Search Report and Written Opinion, PCT/US06/41889, Mailed on Oct. 20, 2008, Applicant: Ardian, Inc., 7 pages.
International Search Report and Written Opinion, PCT/US07/63322, Mailed on Mar. 3, 2008, Applicant: Ardian, Inc., 13 pages.
International Search Report and Written Opinion, PCT/US07/63324, Mailed on Oct. 10, 2008, Applicant: Ardian, Inc., 13 pages.
International Search Report and Written Opinion, PCT/US07/66539, Mailed on Jan. 28, 2008, Applicant: Ardian, Inc., 8 pages.
International Search Report and Written Opinion, PCT/US07/70799, Mailed on Jul. 2, 2008, Applicant: Ardian, Inc., 7 pages.
International Search Report and Written Opinion, PCT/US07/72396, Mailed on Aug. 27, 2008, Applicant: Ardian, Inc., 9 pages.
International Search Report and Written Opinion, PCT/US07/84701, Mailed on Aug. 21, 2008, Applicant Ardian, Inc., 11 pages.
International Search Report and Written Opinion, PCT/US07/84705, Mailed on Jul. 28, 2008, Applicant: Ardian, Inc., 12 pages.
International Search Report and Written Opinion, PCT/US07/84708, Mailed on Aug. 11, 2008, Applicant: Ardian, Inc., 9 pages.
International Search Report and Written Opinion for PCT/US2009/069334; Applicant: Ardian, Inc.; Mailing Date: Mar. 1, 2010, 10 pages.
European Search Report; European Patent Application No. 05806045.0; Applicant: Ardian, Inc.; Date of Mailing: Sep. 22, 2009, 8 pages.
European Search Report; European Patent Application No. 05811851.4; Applicant: Ardian, Inc.; Date of Mailing: Oct. 1, 2009, 7 pages.
European Search Report; European Patent Application No. 06847926.0; Applicant: Ardian, Inc.; Date of Mailing: Feb. 10, 2010, 6 pages.
European Search Report; European Patent Application No. 0775925.8; Applicant Ardian, Inc.; Date of Mailing: Apr. 29, 2010, 9 pages.
European Search Report; European Patent Application No. 07799148.7; Applicant: Ardian, Inc.; Date of Mailing: Jul. 23, 2009, 6 pages.
European Search Report; European Patent Application No. 09156661.2; Applicant: Ardian, Inc.; Date of Mailing: Jul. 23, 2009, 6 pages.
European Search Report; European Patent Application No. 09167937.3; Applicant: Ardian, Inc.; Date of Mailing: Nov. 11, 2009, 6 pages.
European Search Report; European Patent Application No. 09168202.1; Applicant: Ardian, Inc.; Date of Mailing: Nov. 11, 2009, 5 pages.
European Search Report; European Patent Application No. 09168204.7; Applicant: Ardian, Inc.; Date of Mailing: Nov. 19, 2009, 6 pages.
European Search Report; European Patent Application No. 07868755.5; Applicant: Ardian, Inc.; Date of Mailing: Jul. 28, 2010, 7 pages.
Hall, W. H., et al. "Combined embolization and percutaneous radiofrequency ablation of a solid renal tumor." Am. J. Roentgenol,174: 1592-1594 (2000).
Hanson, J. M., et al. "The transplanted human kidney does not achieve functional reinnervation." Clin. Sci, 87: 13-19 (1994).
Hendee, W. R. et al. "Use of Animals in Biomedical Research: The Challenge and Response." *American Medical Association White Paper* (1988).
Medical-Dictionary.com, Definition of "Animal Model," http://medical-dictionary.com (search "Animal Model"), 2005.
Medtronic, Inc., Annual Report (Form 10-K) (Jun. 28, 2011).
Ong, K. L., et al. "Prevalence, Awareness, Treatment, and Control of Hypertension Among United States Adults 1999-2004." Hypertension, 49: 69-75 (2007) (originally published online Dec. 11, 2006).
Renal Denervation (RDN), Symplicity RDN System Common Q&A (2011), http://www.medtronic.com/rdn/mediakit/RDN%20FAQ.pdf.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Blessing, Erwin et al., Cardiac Ablation and Renal Denervation Systems Have Distinct Purposes and Different Technical Requirements, JACC Cardiovascular Interventions, vol. 6, No. 3, 2013.
Mount Sinai School of Medicine clinical trial for Impact of Renal Sympathetic Denervation of Chronic Hypertenion, Mar. 2013, http://clinicaltrials.gov/ct2/show/NCT01628198.
Prochnau, Dirk et al., Catheter-based renal denervation for drug-resistant hypertension by using a standard electrophysiology catheter; EuroIntervention 2012, vol. 7, pp. 1077-1080.
Schneider, Peter A . . . , "Endovascular Skills—Guidewires, Catheters, Arteriography, Balloon Angioplasty, Stents", pp. 70-71, 101 and 188-190 (1998).
Kandarpa, Krishna et al., "Handbook of Interventional Radiologic Procedures", Third Edition, pp. 194-210 (2002).
ThermoCool Irrigated Catheter and Integrated Ablation System, Biosense Webster (2006).
ClinicalTrials.gov, Renal Denervation in Patients with uncontrolled Hypertension in Chinese (2011), www.clinicaltrials.gov/ct2/show/NCT01390831.
U.S. Appl. No. 60/813,589, filed Dec. 29, 2005, Demarais et al.
2003 European Society of Hypertension—European Society of Cardiology guidelines for the management of arterial hypertension, Guidelines Committee, Journal of Hypertension 2003, vol. 21, No. 6, pp. 1011-1053.
Aars, H. and S. Akre, Reflex Changes in Sympathetic Activity and Arterial Blood Pressure Evoked by Afferent Stimulation of the Renal Nerve, Feb. 26, 1999, Acta physiol. Scand., vol. 78, 1970, pp. 184-188.
Abramov, G.S. et al., Alteration in sensory nerve function following electrical shock, Burns vol. 22, No. 8, 1996 Elsevier Science Ltd., pp. 602-606.
Achar, Suraj, M.D., and Suriti Kundu, M.D., Principles of Office Anesthesia: Part I. Infiltrative Anesthesia, Office Procedures, American Family Physician, Jul. 1, 2002, vol. 66, No. 1, pp. 91-94.
Advanced Neuromodulation Systems' Comparison Chart, 1 page, Dec. 16, 2008.
Advances in the role of the sympathetic nervous system in cardiovascular medicine, 2001 SNS Report, No. 3, Springer, Published with an educational grant from Servier, pp. 1-8.
Aggarwal, A. et al., Regional sympathetic effects of low-dose clonidine in heart failure. Hypertension. 2003;41:553-7.
Agnew, William F. et al., Evolution and Resolution of Stimulation-Induced Axonal Injury in Peripheral Nerve, May 21, 1999, Muscle & Nerve, vol. 22, Oct. 1999, John Wiley & Sons, Inc. 1999, pp. 1393-1402.
Ahadian, Farshad M., M.D., Pulsed Radiofrequency Neurotomy: Advances in Pain Medicine, Current Pain and Headache Reports 2004, vol. 8, 2004 Current Science Inc., pp. 34-40.
Alexander, B.T. et al., Renal denervation abolishes hypertension in low-birth-weight offspring from pregnant rats with reduced uterine perfusion, Hypertension, 2005; 45 (part 2): 754-758.
Alford, J. Winslow, M.D. and Paul D. Fadale, M.D., Evaluation of Postoperative Bupivacaine Infusion for Pain Management After Anterior Cruciate Ligament Reconstruction, The Journal of Arthroscopic and Related Surgery, vol. 19, No. 8, Oct. 2003 Arthroscopy Association of North America, pp. 855-861.
Allen, E.V., Sympathectomy for essential hypertension, Circulation, 1952, 6:131-140.
Amersham Health. Hypaque-Cysto 6 pgs. 2003.
Andrews, B.T. et al., The use of surgical sympathectomy in the treatment of chronic renal pain. Br J Urol. 1997;80:6-10.
Antman, Elliott M. and Eugene Braunwald, Chapter 37—Acute Myocardial Infarction, Heart Disease—A Textbook of Cardiovascular Medicine, 5th Edition, vol. 2, 1997, Edited by Eugene Braunwald, pp. 1184-1288.
Archer, Steffen et al., Cell Reactions to Dielectrophoretic Manipulation, Mar. 1, 1999, Biochemical and Biophysical Research Communications, 1999 Academic Press, pp. 687-698.

(56) References Cited

OTHER PUBLICATIONS

Arentz, T. et al., Incidence of pulmonary vein stenosis 2 years after radiofrequency catheter ablation of refractory atrial fibrillation. European Heart Journal. 2003. 24; pp. 963-969.
Arias, M.D., Manuel J., Percutaneous Radio-Frequency Thermocoagulation with Low Temperature in the Treatment of Essential Glossopharyngeal Neuralgia, Surg. Neurol. 1986, vol. 25, 1986 Elsevier Science Publishing Co., Inc., pp. 94-96.
Aronofsky, David H., D.D.S., Reduction of dental postsurgical symptoms using nonthermal pulsed high-peak-power electromagnetic energy, Oral Surg., Nov. 1971, vol. 32, No. 5, pp. 688-696.
Aspelin, Peter, M.D., Ph.D. et al., Nephrotoxic Effects in High-Risk Patients Undergoing Angiography, Feb. 6, 2003, New England Journal of Medicine 2003, vol. 348, No. 6, 2003 Massachusetts Medical Society, pp. 491-499.
Atrial Fibrillation Heart and Vascular Health on Yahoo! Health. 2 pgs. <URL: http://health.yahoo.com/topic/heart/overview/article/healthwise/hw160872;_ylt=AiBT43Ey74HQ7ft3jAb4C.sPu7cF> Feb. 21, 2006.
Augustyniak, Robert A. et al., Sympathetic Overactivity as a Cause of Hypertension in Chronic Renal Failure, Aug. 14, 2001, Journal of Hypertension 2002, vol. 20, 2002 Lippincott Williams & Wilkins, pp. 3-9.
Awwad, Ziad M., FRCS and Bashir A. Atiyat, GBA, JBA, Pain relief using continuous bupivacaine infusion in the paravertebral space after loin incision, May 15, 2004, Saudi Med J 2004, vol. 25 (10), pp. 1369-1373.
Badyal, D. K., H. Lata and A.P. Dadhich, Animal Models of Hypertension and Effect of Drugs, Aug. 19, 2003, Indian Journal of Pharmacology 2003, vol. 35, pp. 349-362.
Baker, Carol E. et al., Effect of pH of Bupivacaine on Duration of Repeated Sciatic Nerve Blocks in the Albino Rat, Anesth Analg, 1991, vol. 72, The International Anesthesia Research Society 1991, pp. 773-778.
Balazs, Tibor, Development of Tissue Resistance to Toxic Effects of Chemicals, Jan. 26, 1974, Toxicology, 2 (1974), Elsevier/North-Holland, Amsterdam, pp. 247-255.
Barajas, L. Innervation of the renal cortex. Fex Proc. 1978;37:1192-201.
Barrett, Carolyn J. et al., Long-term control of renal blood flow: what is the role of the renal nerves?, Jan. 4, 2001, Am J Physiol Regulatory Integrative Comp Physiol 280, 2001, the American Physiological Society 2001, pp. R1534-R1545.
Barrett, Carolyn J. et al., What Sets the Long-Term Level of Renal Sympathetic Nerve Activity, May 12, 2003, Integrative Physiology, Circ Res. 2003, vol. 92, 2003 American Heart Association, pp. 1330-1336.
Bassett, C. Andrew L. et al., Augmentation of Bone Repair by Inductively Coupled Electromagnetic Fields, May 3, 1974, Science, vol. 184, pp. 575-577.
Bassett, C. Andrew L., Fundamental and Practical Aspects of Therapeutic Uses of Pulsed Electromagnetic Fields (PEMFs), Critical Reviews in Biomedical Engineering, vol. 17, Issue 5, 1989, pp. 451-514.
Beebe, Stephen J. et al., Nanosecond pulsed electric fields modulate cell function through intracellular signal transduction mechanisms, Apr. 8, 2004, Physiol. Meas. 25, 2004, IOP Publishing Ltd. 2004, pp. 1077-1093.
Beebe, Stephen J., et al., Nanosecond Pulsed Electric Field (nsPEF) Effects on Cells and Tissues: Apoptosis Induction and Tumor Growth Inhibition, Oct. 11, 2001, IEEE Transactions on Plasma Science, vol. 30, No. 1, Feb. 2002, IEEE 2002, pp. 286-292.
Bello-Reuss, E. et al., Acute unilateral renal denervation in rats with extracellular volume expansion, Departments of Medicine and Physiology, University of North Carolina School of Medicine. F26-F32 Jul. 1975.
Bello-Reuss, E. et al., Effect of renal sympathetic nerve stimulation on proximal water and sodium reabsorption, J Clin Invest, 1976;57:1104-1107.
Bello-Reuss, E. et al., Effects of Acute Unilateral Renal Denervation in the Rat, J Clin Invest, 1975;56:208-217.
Berde, C. et al., Local Anesthetics, Anesthesia, Chapter 13, 5th addition, Churchill-Livingston, Philadelphia 2000, pp. 491-521.
Bhadra, Niloy and Kevin L. Kilgore, Direct Current Electrical Conduction Block of Peripheral Nerve, Feb. 25, 2004, IEEE Transactions on Neural Systems and Rehabilitation Engineering, vol. 12, No. 3, Sep. 2004, pp. 313-324.
Bhandari, A. and Ellias, M., Loin pain hematuria syndrome: Pain control with RFA to the Splanchanic plexus, The Pain Clinic, 2000, vol. 12, No. 4, pp. 323-327.
Bhatt, Deepak L. et al., Rhabdomyolysis Due to Pulsed Electric Fields, May 11, 1989, Plastic and Reconstructive Surgery Jul. 1990, pp. 1-11.
Bichet, D., et al., Renal intracortical blood flow and renin secretion after denervation by 6-hydroxydopamine. Can J Physiol Pharmacol. 1982;60:184-92.
Bigler, D. et al., Tachyphylaxis during postoperative epidural analgesia—new insights, Apr. 15, 1987, Letter to the Editor, Acta Anaesthesiol Scand. 1987, vol. 31, pp. 664-665.
Binder, Allan et al., Pulsed Electromagnetic Field Therapy of Persistent Rotator Cuff Tendinitis, The Lancet, Saturday Mar. 31, 1984, The Lancet Ltd., pp. 695-698.
Black, M.D., Henry R., Resistant Hypertension 2004, presentation at Rush University Medical Center, Jul. 15, 2004, 40 pages.
Blad, B., et al., An Electrical Impedance index to Assess Electroporation in Tissue, Tissue and Organ (Therapy), 2001, Oslo, pp. 31-34, www.bl.uk <http://www.bl.uk> British Library, 2001, Oslo.
Blair, M. L. et al, Sympathetic activation cannot fully account for increased plasma renin levels during water deprivation, Sep. 23, 1996, Am. J. Physiol., vol. 272, 1997, the American Physiological Society 1997, pp. R1197-R1203.
Blomberg, S.G., M.D., PhD, Long-Term Home Self-Treatment with High Thoracic Epidural Anesthesia in Patients with Severe Coronary Artery Disease, Mar. 29, 1994, Anesth Analg 1994, vol. 79, 1994 International Anesthesia Research Society, pp. 413-421.
Boehmer, J.P., Resynchronization Therapy for Chronic CHF: Indications, Devices and Outcomes. Penn State College of Medicine: Penn State Heart and Vascular Institute. Transcatheter Cardiovascular Therapeutics 2005. 31 slides.
Bourge, R.C., Heart Failure Monitoring Devices: Rationale and Status 28 pages, Feb. 2001.
Braunwald, E., Heart Disease, A Textbook of Cardiovascular Medicine, 5th Ed., vol. 2, 1997, pp. 480-481, 824-825, 1184-1288 and 1923-1925, W.B. Saunders Company.
Bravo, E.L., et al., Renal denervation for resistant hypertension, American Journal of Kidney Diseases, 2009, 3 pgs.
Bunch, Jared T. et al. Mechanisms of Phrenic Nerve Injury During Radiofrequency Ablation at the Pulmonary Vein Orifice. Journal of Cardiovascular Electrophysiclody. vol. 16, No. 12. pp. 1318-1325. Dec. 2005.
Burkhoff, D., Interventional Device-Based Therapy for CHF Will Redefine Current Treatment Paradigms. Columbia University. 2004. 32 slides.
Burns, J. et al., Relationship between central sympathetic drive and magnetic resonance imaging-determined left ventricular mass in essential hypertension. Circulation. 2007;115:1999-2005.
Cahana, A. et al., Acute Differential Modulation of Synaptic Transmission and Cell Survival During Exposure to Pulsed and Continuous Radiofrequency Energy, May 2003, The Journal of Pain, vol. 4, No. 4, © 2003 by the American Pain Society, pp. 197-202.
Cahana, Alex, M.D., Pulsed Radiofrequency: A Neurobiologic and Clinical Reality, May 17, 2005, Anesthesiology 2005, vol. 103, No. 6, Dec. 2005, 2005 American Society of Anesthesiologists, Inc. Lippincott Williams & Wilkins, Inc., p. 1311.
Calaresu, F.R. et al., Haemodynamic Responses and Renin Release During Stimulation of Afferent Renal Nerves in the Cat, Aug. 12, 1975, J. Physiol. 1976, vol. 255, pp. 687-700.
Cameron, Tracy. Micromodular Implants to Provide Electrical Stimulation of Paralyzed Muscles and Limbs. IEEE Transactions on Biomedical Engineering, vol. 44, No. 9, Sep. 1997. pp. 781-790.
Campese, V.M. et al., Renal afferent denervation prevents hypertension in rats with chronic renal failure. Hypertension. 1995;25:878-82.

(56) References Cited

OTHER PUBLICATIONS

Campese, V.M. et al., Renal Afferent Denervation Prevents the Progression of Renal Disease in the Renal Ablation Model of Chronic Renal Failure in the Rat, Am J Kidney Dis. 1995;26:861-5.
Campese, V.M., A new model of neurogenic hypertension caused by renal injury: pathophysiology and therapeutic implications, Clin Exp Nephrol (2003) 7: 167-171, Japanese Society of Nephrology 2003.
Campese, V.M., Neurogenic factors and hypertension in chronic renal failure, Journal of Nephrology, vol. 10, No. 4, 1997, Societa Italiana di Nefrologia, pp. 184-187.
Campese, V.M., Neurogenic factors and hypertension in renal disease. Kidney Int. 2000;57 Suppl 75:S2-3.
Canbaz, S. et al., Electrophysiological evaluation of phrenic nerve injury during cardiac surgery—a prospective, controlled clinical study. BioMed Central. 5 pgs. 2004.
Cardiac Glycosides, Heart Disease—A Textbook of Cardiovascular Medicine vol. 2, Edited by Eugene Braunwald, 5th Edition, WB Saunders Company, pp. 480-481, 1997.
Carls, G. et al., Electrical and magnetic stimulation of the intercostal nerves: a comparative study, Electromyogr, clin. Neurophysiol. 1997, vol. 37, pp. 509-512.
Carlson, Scott H. and J. Michael Wyss, e-Hypertension—Opening New Vistas, Introductory Commentary, Hypertension 2000, vol. 35, American Heart Association, Inc. 2000, p. 538.
Carson, P., Device-based Treatment for Chronic Heart Failure: Electrical Modulation of Myocardial Contractility. Transcatheter Cardiovascular Therapeutics 2005. 21 slides.
Chang, Donald C., Cell poration and cell fusion using an oscillating electric field, Biophysical Journal, vol. 56, Oct. 1989, Biophysical Society, pp. 641-652.
Chen, S.A. et al., Initiation of atrial fibrillation by ectopic beats originating from the pulmonary veins: electrophysiological characteristics, pharmacological responses, and effects of radiofrequency ablataion, Circulation, 1999, 100:1879-1886.
Chin, J.L. et al., Renal autotransplantation for the loin pain-hematuria syndrome: long term follow up of 26 cases, J Urol, 1998, vol. 160, pp. 1232-1236.
Chiou, C.W. et al., Efferent Vagal Innervation of the Canine Atria and Sinus and Atrioventricular Nodes. Circulation. Jun. 1997. 95(11):2573-2584. Abstract only. 2 pgs.
Chobanian, Aram V. et al., Seventh Report of the Joint National Committee on Prevention, Detection, Evaluation, and Treatment of High Blood Pressure, Nov. 6, 2003, Hypertension 2003, vol. 42, 2003 American Heart Association, Inc., pp. 1206-1252.
*Clinical Trials in Hypertension and Renal Diseases, Slide Source,* www.hypertensiononline.org 33 pages Aug. 13, 2001.
Conradi, E. and Ines Helen Pages, Effects of Continous and Pulsed Microwave Irradiation on Distribution of Heat in the Gluteal Region of Minipigs, Scand J Rehab Med, vol. 21, 1989, pp. 59-62.
Converse, R.L., Jr. et al., Sympathetic Overactivity in Patients with Chronic Renal Failure, N Engl J Med. Dec. 31, 1992, vol. 327 (27), pp. 1912-1918.
Cosman, E.R., Jr. et al., Electric and Thermal Field Effects in Tissue Around Radiofrequency Electrodes, Pain Medicine, vol. 6, No. 6, 2005, American Academy of Pain Medicine, pp. 405-424.
Cosman, E.R., Ph.D., A Comment on the History of the Pulsed Radiofrequency Technique for Pain Therapy, Anesthesiology Dec. 2005, vol. 103, No. 6, 2005 American Society of Anesthesiologists, Inc. Lippincott Williams & Wilkins, Inc., p. 1312.
Crawford, William H. et al., Pulsed Radio Frequency Therapy of Experimentally Induced Arthritis in Ponies, Dec. 18, 1989, Can. J. Vet. Res. 1991, vol. 55, pp. 76-85.
Cryovascular Systems, Inc. Pre-Clinical Testing Establishing Parameters. PowerPoint Presentation. 18 slides.
Curtis, J.J. et al., Surgical theray for persistent hypertension after renal transplantation, Transplantation, 1981, 31(2):125-128.
Dahm, Peter et al., Efficacy and Technical Complications of Long-Term Continuous Intraspinal Infusions of Opioid and/or Bupivacaine in Refractory Nonmalignant Pain . . . , Oct. 6, 1997, The Clinical Journal of Pain, vol. 14, No. 1, 1998, Lippincott-Raven Publishers 1998, pp. 4-16.
Dahm, Peter O. et al., Long-Term Intrathecal Infusion of Opioid and/or Bupivacaine in the Prophylaxis and Treatment of Phantom Limb Pain, Neuromodulation, vol. 1, No. 3, 1998, International Neuromodulation Society 1998, pp. 111-128.
Dang, Nicholas C. et al., A Novel Approach to Increase Total Urine Output in Heart Failure: Renal Nerve Blockade, ACC 2005 poster; 1 page.
Daniel, Alan and Honig, Carl R. Does Histamine Influence Vasodilation Caused by Prolonged Arterial Occlusion or Heavy Exercise? The Journal of Pharmacology and Experimental Therapeutics. vol. 215 No. 2. Aug. 21, 1980. pp. 533-538.
Davalos, R. et al., Electrical Impedance Tomography for Imaging Tissue Electroporation, Jul. 25, 2003, IEEE Transactions on Biomedical Engineering, vol. 51, No. 5, May 2004, IEEE 2004, pp. 761-767.
Davalos, R.V. et al., Tissue Ablation with Irreversible Electroporation, Sep. 7, 2004, Annals of Biomedical Engineering, Feb. 2005, vol. 33, No. 2, 2005 Biomedical Engineering Society, pp. 223-231.
De Leeuw, Peter W. et al., Renal Vascular Tachyphylaxis to Angiotensin II: Specificity of the Response for Angiotensin, Dec. 28, 1981, Life Sciences, vol. 30, 1982 Pergamon Press Ltd., pp. 813-819.
Deng, Jingdong et al., The Effects of Intense Submicrosecond Electrical Pulses on Cells, Nov. 26, 2002, Biophysical Journal, vol. 84, Apr. 2003, Biophysical Society 2003, pp. 2709-2714.
Denton, Kate M. et al., Differential Neural Control of Glomerular Ultrafiltration, Jan. 30, 2004, Proceedings of the Australian Physiological and Pharmacological Society Symposium: Hormonal, Metabolic and Neural Control of the Kidney, Clinical and Experimental Pharmacology and Physiology (2004) 31, pp. 380-386.
Dev, Nagendu B., Ph.D. et al., Intravascular Electroporation Markedly Attenuates Neointima Formation After Balloon Injury of the Carotid Artery in the Rat, Journal of Interventional Cardiology, vol. 13, No. 5, 2000, pp. 331-338.
Dev, Nagendu B., Ph.D. et al., Sustained Local Delivery of Heparin to the Rabbit Arterial Wall with an Electroporation Catheter, May 5, 1998, Catheterization and Cardiovascular Diagnosis, vol. 45, 1998, Wiley-Liss, Inc. 1998, pp. 337-345.
Devereaux, R.B. et al., Regression of Hypertensive Left Ventricular Hypertrophy by Losartan Compared With Atenolol: The Losartan Intervention for Endpoint Reduction in Hypertension (LIFE) Trial, Circulation, 2004, vol. 110, pp. 1456-1462.
Dibona, Gerald F. and Linda L. Sawin, Role of renal nerves in sodium retention of cirrhosis and congestive heart failure, Sep. 27, 1990, Am. J. Physiol. 1991, vol. 260, 1991 the American Physiological Society, pp. R298-R305.
Dibona, Gerald F. and Susan Y. Jones, Dynamic Analysis of Renal Nerve Activity Responses to Baroreceptor Denervation in Hypertensive Rats, Sep. 19, 2000, Hypertension Apr. 2001, American Heart Association, Inc. 2001, pp. 1153-1163.
Dibona, Gerald F. and Ulla C. Kopp, Neural Control of Renal Function, Physiological Reviews, vol. 77, No. 1, Jan. 1997, the American Physiological Society 1997, pp. 75-197.
Dibona, Gerald F. and Ulla C. Kopp, Role of the Renal Sympathetic Nerves in Pathophysiological States, Neural Control of Renal Function, vol. 77, pp. 142-197 Jan. 1997.
Dibona, Gerald F., Functionally Specific Renal Sympathetic Nerve Fibers: Role in Cardiovascular Regulation, Mar. 6, 2001, American Journal of Hypertension, 2001, vol. 14, 2001 American Journal of Hypertension, Ltd. Published by Elsevier Science Inc., pp. 163S-170S.
Dibona, Gerald F., L.L. Sawin, Effect of renal nerve stimulation on NaCl and H2O transport in Henle's loop of the rat,: 1982, American Physiological Society, F576-F580, 5 pgs.
Dibona, Gerald F., Nervous Kidney—Interaction Between Renal Sympathetic Nerves and the Renin-Angiotensin System in the Control of Renal Function, Jun. 21, 2000, Hypertension 2000, vol. 36, 2000 American Heart Association, Inc., pp. 1083-1088.
Dibona, Gerald F., Neural Control of the Kidney—Past, Present and Future, Nov. 4, 2002, Novartis Lecture, Hypertension 2003, 41 part 2, 2002 American Heart Association, Inc., pp. 621-624.

(56) References Cited

OTHER PUBLICATIONS

DiBona, Gerald F., Neural Control of the Kidney: Functionally Specific Renal Sympathetic Nerve Fibers, Starling Lecture, Am J Physiol Regulatory Integrative Comp Physiol, 2000, 279, 2000 The American Physiological Society, pp. R1517-R1524.

Dibona, Gerald F., Peripheral and Central Interactions between the Renin-Angiotensin System and the Renal Sympathetic Nerves in Control of Renal Function, Annals New York Academy of Sciences, pp. 395-406 Jan. 25, 2006.

Dibona, Gerald F., Renal Innervation and Denervation: Lessons from Renal Transplantation Reconsidered, Artificial Organs, vol. 11, No. 6, Raven Press, Ltd., 1987 International Society for Artificial Organs, pp. 457-462.

Dibona, Gerald F., Sympathetic Nervous System and the Kidney in Hypertension, Current Opinion in Nephrology and Hypertension 2002, vol. 11, 2002 Lippincott Williams & Wilkins, pp. 197-200.

Dibona, Gerald F., The Sympathetic Nervous System and Hypertension, Dec. 4, 2003, Hypertension Highlights, Hypertension Feb. 2004, vol. 43, 2004 American Heart Association, Inc., pp. 147-150.

Dibona, Gerald, LL Sawin, Effect of renal denervation on dynamic autoregulation of renal blood flow, Feb. 12, 2004, AmJ Physiol Renal Physiol 286, pp. F1209-1218.

Dong, Jun et al. Incidence and Predictors of Pulmonary Vein Stenosis Following Catheter Ablation of Atrial Fibrillation Using the Anatomic Pulmonary Vein Ablation Approach: Results from Paired Magnetic Resonance Imaging. Journal of Cardiovascular Electrophysiology. vol. 16, No. 8, Aug. 2005. pp. 845-852.

Dorros, Gerald, M.D., Renal Artery Stenting State of the Art, presentation, TCT, Washington D.C., Sep. 2003, 27 pages.

Dueck, Ron, M.D., Noninvasive Cardiac Output Monitoring, The Cardiopulmonary and Critical Care Journal, Chest, vol. 120, sec. 2, Aug. 2001, American College of Chest Physicians 2005, pp. 339-341, 5 pages.

Dunn, Matthew D. et al., Laparoscopic Nephrectomy in Patients With End-Stage Renal Disease and Autosomal Dominant Polycystic Kidney Disease,Oct. 25, 1999, American Journal of Kidney Diseases, vol. 35, No. 4 Apr. 2000, National Kidney Foundation, Inc. 2000, pp. 720-725.

Durand, D.M., Electric Field Effects in Hyperexcitable Neural Tissue: A Review, Radiation Protection Dosimetry, vol. 106, No. 4, 2003 Nuclear Technology Publishing, pp. 325-331.

*ECM 830 Specifications Sheet*. tech@genetronics.com 20-001796-01 Rev D. 2 pgs.

Effects of Renal Failure on the Cardiovascular System, 5th Edition Heart Disease, A Textbook of Cardiovascular Medicine, vol. 2, Edited by Eugene Braunwald, W.B. Saunders Company, pp. 1923-1925 1997.

Electrical Stimulation for the Treatment of Chronic Wounds, Radiation Protection Standard, Maximum Exposure Levels to Radiofrequency Fields—3 KHz to 300 GHz, Radiation Protection Series No. 3, Australian Radiation Protection and Nuclear Safety Agency, Apr. 1996, 322 pgs.

*Electropermeabilization (Electroporation)*, Cyto Pulse Sciences, Inc., http://www.cytopulse.com/electroporation.html (last accessed Mar. 3. 2005), 3 pgs.

*Electroporation based Technologies and Treatments*, ESPE Newsletter No. 6. QLK 02002-2003, Jan. 2005, www.cliniporator.com, 4 pgs.

End-stage renal disease payment policies in traditional Medicare, Chapter 8, Report to the Congress: Medicare Payment Policy, Mar. 2001, Medpac, pp. 123-138.

Epidemiology of Renal Disease in Hypertension, slide presentation by hypertensiononline.org, 21 pages Mar. 30, 2001.

Erdine, Serap and Alev Arat-Ozkan, Resistant Hypertension, European Society of Hypertension Scientific Newsletter: Update on Hypertension Management 2003, vol. 4, No. 15, 2 pages.

Esler, M. et al., Mechanism of elevated plasma noradrenaline in the course of essential hypertension. J Cardiovasc Pharmacol. 1986;8:S39-43.

Esler, M. et al., Noradrenaline release and the pathophysiology of primary human hypertension. Am J Hypertens. 1989; 2:140S-146S.

Esler, M. et al., Sympathetic nerve biology in essential hypertension, Clin and Exp Pharmacology and Physiology, 2001, 28:986-989.

European Examination Report; European Patent Application No. 07799148.7; Applicant: Ardian, Inc.; Date of Mailing: Jan. 19, 2010, 4 pgs.

European Search Report; European Patent Application No. 07798341.9; Applicant: Ardian, Inc.; Date of Mailing: Aug. 4, 2011, 6 pgs.

European Examination Report; European Patent Application No. 09156661.2; Applicant: Ardian, Inc.; Date of Mailing: Jan. 19, 2010, 6 pgs.

Evelyn, K.A. et al., Effect of thoracolumbar sympathectomy on the clinical course of primary (essential) hypertension, Am J Med, 1960;28:188-221.

*Ex parte Quayle* Office Action; U.S. Appl. No. 11/144,173; Mailed on May 28, 2009, 4 pgs.

Fact Book Fiscal Year 2003, National Institutes of Health National Heart, Lung, and Blood Institute, Feb. 2004, 197 pgs.

Fajardo, J. et al., Effect of chemical sympathectomy on renal hydroelectrolytic handling in dogs with chronic caval constriction. Clin Physiol Biochem. 1986;4:252-6.

Fareed, Jawed, Ph.D. et al., Some Objective Considerations for the Use of Heparins and Recombinant Hirudin in Percutaneous Transluminal Coronary Angoplasty, Seminars in Thrombosis and Hemostasis 1991, vol. 17, No. 4, 1991 by Thieme Medical Publishers, Inc., pp. 455-470.

Fava, M. et al., Initial Human Experience with CryoPlasty™ in the Treatment of Infrainguinal Arterial Disease, Abstract. 1 page.

Fava, M., Clinical Testing Establishing Safety & Efficacy, PowerPoint Presentation. Cryovascular Systems, Inc. 14 slides.

Ferguson, D.R. et al., Responses of the pig isolated renal artery to transmural electrical stimulation and drugs, Dec. 7, 1984, Br. J. Pharmac. 1985, vol. 84, The Macmillan Press Ltd. 1985, pp. 879-882.

Fernandez-Ortiz, Antonio, et al., A New Approach for Local Intravascular Drug Delivery—Iontophoretic Balloon, Intravascular Iontophoretic Local Delivery, Circulation, vol. 89, No. 4, Apr. 1994, pp. 1518-1522.

Fields, Larry E. et al., The Burden of Adult Hypertension in the United States 1999 to 2000—A Rising Tide, May 18, 2004, American Heart Association 2004, Hypertension Oct. 2004, pp. 1-7.

Final Office Action; U.S. Appl. No. 11/233,814; Mailed on Jan. 29, 2009, 11 pgs.

Final Office Action; U.S. Appl. No. 11/266,993; Mailed on Jan. 8, 2010, 7 pgs.

Final Office Action; U.S. Appl. No. 11/363,867; Mailed on May 1, 2009, 8 pgs.

Final Office Action; U.S. Appl. No. 11/451,728; Mailed on Jan. 13, 2009, 7 pgs.

Final Office Action; U.S. Appl. No. 11/599,649; Mailed on Jan. 15, 2009, 10 pgs.

Final Office Action; U.S. Appl. No. 11/599,723; Mailed on Apr. 5, 2010, 17 pgs.

Final Office Action; U.S. Appl. No. 11/599,890; Mailed on Apr. 29, 2009, 9 pgs.

Fischell, Tim A. et al., Ultrasonic Energy: Effects on Vascular Function and Integrity, Circulation: Journal of the American Heart Association. 1991. 84;pp. 1783-1795.

Freeman, Scott A. et al., Theory of Electroporation of Planar Bilayer Membranes: Predictions of the Aqueous Area, Change in Capacitance, and Pore-Pore Separation, Feb. 23, 1994, Biophysical Journal, Jul. 1994, vol. 67, 1994 by the Biophysical Society, pp. 42-56.

Fukuoka, Yuko et al., Imaging of neural conduction block by neuromagnetic recording, Oct. 16, 2002, Clinical Neurophysiology, vol. 113, 2002, Elsevier Science Ireland Ltd. 2002, pp. 1985-1992.

Fuster, Valentin et al. ACC/AHA/ESC Practice Guidelines: ACA/AHA/ESC 2006 Guidelines for the Management of Patients with Atrial Fibrillation. JACC vol. 48, No. 4, Aug. 15, 2006.

Gami, Apoor S., M.D. and Vesna D. Garovic, M.D., Contrast Nephropathy After Coronary Angiography, Mayo Clin Proc. 2004, vol. 79, 2004 Mayo Foundation for Medical Education and Research, pp. 211-219.

(56) References Cited

OTHER PUBLICATIONS

Gattone II, Vincent H. et al., Contribution of Renal Innervation to Hypertension in Polycystic Kidney Disease in the Rat, University of Chicago Section of Urology, 16 pages, Mar. 17, 2008.

Gaylor, D.C. et al., Significance of Cell Size and Tissue Structure in Electrical Trauma, Jan. 26, 1988, J. theor. Biol. 1988, vol. 133, 1988 Academic Press Limited, pp. 223-237.

Gazdar, A.F. and G.J. Dammin, Neural degeneration and regeneration in human renal transplants, NEJM, Jul. 30, 1970, 283:222-244.

Gehl, Julie et al., In Vivo Electroporation of Skeletal Muscle: Threshold, Efficacy and Relation to Electric Field Distribution, Biochimica et Biophysica Acta, 1428, 1999, Elsevier Science B.V. 1999, pp. 233-240, www.elsevier.com/locate/bba <http:www.elsevier.com/locate/bba>.

Getts, R.T. et al., Regression of left ventricular hypertrophy after bilateral nephrectomy, Nephrol Dial Transplant, 2006, vol. 21, pp. 1089-1091.

Ghoname, El-sayed A. et al., Percutaneous electrical nerve stimulation: an alternative to TENS in the management of sciatica, Apr. 26, 1999, Pain 1999, vol. 83, 1999 International Association for the Study of Pain / Published by Elsevier Science B.V., pp. 193-199.

Gimple, M.D., Lawrence et al., Effect of Chronic Subcutaneous or Intramural Administration of Heparin on Femoral Artery Restenosis After Balloon Angioplasty in Hypercholesterolemic Rabbits, Laboratory Investigation, Circulation, vol. 86, No. 5, Nov. 1992, pp. 1536-1546.

Goldberger, Jeffrey J. et al., New technique for vagal nerve stimulation, Jun. 2, 1999, Journal of Neuroscience Methods 91, 1999, Elsevier Science B.V. 1999, pp. 109-114.

Gorbunov, F.E. et al., The Use of Pulsed and Continuous Short Wave Diathermy (Electric Field) in Medical Rehabilitation of the Patients with Guillan-Barre Syndrome and Other Peripheral Myelinopathies, May 6, 1994, 5 pages (most of article in Russian language).

Gottschalk, C.W., Renal nerves and sodium excretion, Ann. Rev. Physiol., 1979, 41:229-240.

Greenwell, T.J. et al., the outcome of renal denervation for managing loin pain haematuria syndrome. BJU International, 2004; 4 pgs.

Gruberg, Luis, M.D. et al., The Prognostic Implications of Further Renal Function Deterioration Within 48 h of Interventional Coronary Procedures in Patients with Pre-existent Chronic Renal Insufficiency, Jun. 19, 2000, Journal of the American College of Cardiology 2000, vol. 36, No. 5, 2000 by the American College of Cardiology, pp. 1542-1548.

Guimaraes, Sarfim. Vascular Adrenoceptors: An Update. pp. 319-356, Jun. 1, 2001.

Haissaguerre, M. et al., Spontaneous initiation of atrial fibrillation by ectopic beats orginating in the pulmonary veins, New England Journal of Medicine, 1998, 339: 659-666.

Hajjar, Ihab, M.D., M.S. and Theodore A. Kotchen, M.D., Trends in Prevalence, Awareness, Treatment, and Control of Hypertension in the United States, 1988-2000, JAMA, Jul. 9, 2003, vol. 290, No. 2, pp. 199-206.

Hammer, Leah W. Differential Inhibition of Functional Dilation of Small Arterioles by Indomethacin and Glibenclamide. Hypertension. Feb. 2001 Part II. pp. 599-603.

Hampers, C.L. et al., A hemodynamic evaluation of bilateral nephrectomy and hemodialysis in hypertensive man, Circulation. 1967;35:272-288.

Hamza, M.D., Mohamed A. et al., Effect of the Duration of Electrical Stimulation on the Analgesic Response in Patients with Low Back Pain, Anesthesiology, vol. 91, No. 6, Dec. 1999, American Society of Anesthesiologists, Inc. 1999, pp. 1622-1627.

Han, Hyo-Kyung and Gordon L. Amidon, Targeted Prodrug Design to Optimize Drug Delivery, Mar. 21, 2000, AAPS Pharmsci 2000, 2 (1) article 6, pp. 1-11.

Hansen, J.M. et al., The transplanted human kidney does not achieve functional reinnervation, Clin Science, 1994, vol. 87, pp. 13-20.

Hasking, G.J. et al., Norepinephrine spillover to plasma in patients with congestive heart failure: evidence of increased overall and cardiorenal sympathetic nervous activity. Circulation. 1986;73:615-21.

Hausberg, M. et al., Sympathetic nerve activity in end-stage renal disease, Circulation, 2002, 106: 1974-1979.

Heart Arrhythmia Heart and Vascular Health on Yahoo! Health. 13 pgs. <URL: http://health.yahoo.com/topic/heart/overview/article/mayoclinic/21BBE2B0-128D-4AA2- A5CE215065586678;_ylt=Aqd9M5rNyHD0sbPOmHXFhLcPu7cF> Feb. 16, 2005.

Heart Disease and Stroke Statistics—2004 Update, American Heart Association, American Stroke Association, Dallas, Texas, 2003 American Heart Association, 52 pgs.

Heida, Tjitske, et al., Investigating Membrane Breakdown of Neuronal Cells Exposed to Nonuniform Electric Fields by Finite-Element Modeling and Experiments, May 9, 2002, IEEE Transactions on Biomedical Engineering, vol. 49, No. 10, Oct. 2002, IEEE 2002, pp. 1195-1203.

Heuer, G.J., The surgical treatment of essential hypertension, Annals of Surgery, 1936; 104 (4): 771-786.

Higuchi, Yoshinori, M.D., Ph.D. et al, Exposure of the Dorsal Root Ganglion in Rats to Pulsed Radiofrequency Currents Activates Dorsal Horn Lamina I and II Neurons, Dec. 4, 2001, Experimental Studies, Neurosurgery, vol. 50, No. 4, Apr. 2002, pp. 850-856.

Hildebrand, Keith R., D.V.M., Ph.D. et al., Stability, Compatibility, and Safety of Intrathecal Bupivacaine Administered Chronically via an Implantable Delivery System, May 18, 2001, The Clinical Journal of Pain, vol. 17, No. 3, 2001 Lippincott Williams & Wilkins, Inc., pp. 239-244.

Hing, Esther, M.P.H. and Kimberly Middleton, B.S.N., M.P.H., National Hospital Ambulatory Medical Care Survey: 2001 Outpatient Department Summary, Aug. 5, 2003, Advance Data from Vital and Health Statistics, No. 338, CDC, 32 pages.

Hodgkin, Douglas D. et al., Electrophysiologic Characteristics of a Pulsed Iontophoretic Drug-Delivery System in Coronary Arteries, Journal of Cardiovascular Pharmacology. 29(1):pp. 39-44, Jan. 1997. Abstract. 2 pgs.

Hopp, F.A. et al., Respiratory Responses to Selective Blockade of Carotid Sinus Baroreceptors in the Dog, Jun. 22, 2005, Am J Physiol Regul Integr Comp Physiol 1998, vol. 275, 2005 American Physiological Society, pp. R10-R18.

Hortobagyi, Gabriel N., Randomized Trial of High-Dose Chemotherapy and Blood Cell Autographs for High-Risk Primary Breast Carcinoma, Journal of the National Cancer Institute, vol. 92, No. 3, Feb. 2, 2000, pp. 225-233.

Horwich, Tamara, M.D., New Advances in the Diagnosis and Management of Acute Decompensated Heart Failure, the heart.org satellite program, Rapid Review, CME Symposium presented on Nov. 8, 2004 at the Sheraton New Orleans Hotel, 4 pages.

Huang, Wann-Chu et al. Renal Denervation Prevents and Reverses Hyperinsulinemia-Induced Hypertension in Rats, Mar. 25, 1998, Hypertension 1998, vol. 32, 1998 American Heart Association, pp. 249-254.

Huang, Yifei et al., Remodeling of the chronic severely failing ischemic sheep heart after coronary microembolization: functional, energetic, structural and cellular responses, Jan. 8, 2004, Am J Physiol. Heart Circ. Physiol. 2004, vol. 286, 2004 the American Physiological Society, pp. H2141-H2150.

Hughes, Gordon B., M.D. et al., A Comparative Study of Neuropathologic Changes Following Pulsed and Direct Current Stimulation of the Mouse Sciatic Nerve, Jun. 27, 1980, American Journal of Otolaryngology, Nov. 1980, vol. 1, No. 5, pp. 378-384.

*Hypertension and Renal Disease: Mechanisms.* Slide Show by www.hypertensiononline.org, 22 pages Mar. 30, 2001.

Hypertension Incidence and Prevalence, Age-Specific Rates, by Gender, B.C., 2001/2002, Graph, Chronic Disease Management, May 2003, British Columbia Ministry of Health Services, 1 page.

Implantable Neurostimulation Systems, Medtronic Neurological, http://medtronic.com/neuro/paintherapies/pain_treatment_ladder/pdf/implantable_brochure.pdf.

Implantable Pump—The Medtronic MiniMed 2007 Implantable Insulin Pump System, Medtronic MiniMed 2004, 4 pgs.

(56) References Cited

OTHER PUBLICATIONS

Infumedics Inc., Background and products paper and comparison of Medtronic SynchroMed II and Infumedics Prometra pumps, 3 pgs.
International Search Report, PCT/US02/0039, Mailed Sep. 11, 2002, Applicant: Advanced Neuromodulation Systems, Inc.
International Search Report, PCT/US02/25712, Mailed on Apr. 23, 2003, Applicant: Cyberonics, Inc.
International Search Report, PCT/US03/08014, Mailed on Sep. 23, 2003, Applicant: The General Hospital Corporation.
International Search Report, PCT/US03/09764, Mailed on Oct. 28, 2003, Applicant: CVRX, Inc.
Introduction to Autonomic Pharmacology, Chapter 3, Part 2 Autonomic Pharmacology, pp. 18-26, May 24, 2002.
Isovue: Data Sheet. Regional Health Limited. 8 pgs. Mar. 11, 2003.
Israili, Z.H., Clinical pharmacokinetics of angiotensin II (AT) receptor blockers in hypertension, Journal of Human Hypertension, 2000, Macmillan Publishers Ltd., vol. 14, pp. S73-S86.
Janda, J., Impact of the electrical stimulation apparatus rebox on the course of ischemic renal damage in rats, British Library—The world's knowledge pp. 252-254 (translated and untranslated versions) 1996.
Janssen, Ben J.A. et al., Effects of complete renal denervation and selective afferent renal denervation on the hypertension induced by intrarenal norepinephrine infusion in conscious rats, Jan. 4, 1989, Journal of Hypertension 1989, vol. 7, No. 6, Current Science Ltd, pp. 447-455.
Jia, Jianping et al., Cold injury to nerves is not due to ischaemia alone, Brain. 121;pp. 989-1001. 1998.
Jia, Jianping et al . . . , The pathogenesis of non-freezing cold nerve injury: Observations in the rat, Brain. 120; pp. 631-646. 1997.
Jin, Yuanzhe et al., Pulmonary Vein Stenosis and Remodeling After Electrical Isolation for Treatment of Atrial Fibrillation: Short- and Medium-Term Follow-Up, PACE, vol. 27. pp. 1362-1370. Oct. 2004.
Johansson, Bjorn, Electrical Membrane Breakdown, A Possible Mediator of the Actions of Electroconvulsive Therapy, Medical Hypotheses 1987, vol. 24, Longman Group UK Ltd 1987, pp. 313-324.
Joles, J.A. et al., Causes and Consequences of Increased Sympathetic Activity in Renal Disease. Hypertension. 2004;43:699-706.
Jorgensen, William A. et al., Electrochemical Therapy of Pelvic Pain: Effects of Pulsed Electromagnetic Fields (PEMF) on Tissue Trauma, Eur J Surg 1994, Suppl 574, vol. 160, 1994 Scandinavian University Press, pp. 83-86.
Joshi, R. P. and K. H. Schoenbach, Mechanism for membrane electroporation irreversibility under high-intensity, ultrashort electrical pulse conditions, Nov. 11, 2002, Physical Review E 66, 2002, The American Physical Society 2002, pp. 052901-1-052901-4.
Joshi, R. P. et al., Improved energy model for membrane electroporation in biological cells subjected to electrical pulses, Apr. 9, 2002, Physical Review E, vol. 65, 041920-1, 2002 The American Physical Society, 8 pages.
Joshi, R. P. et al., Self-consistent simulations of electroporation dynamics in biological cells subjected to ultrashort electrical pulses, Jun. 21, 2001, Physical Review E, vol. 64, 011913, 2001 The American Physcial Society, pp. 1-10.
Joye, James D.et al., In Vitro Studies of Arterial Freezing Injury, 4 pgs.
Joye, James D.et al., In Vivo Study of Endovascular Cryotherapy for the Prevention of Restenosis, 4 pages, 2003.
Kanduser, Masa et al., Effect of surfactant polyoxyethylene glycol (C12E8) on electroporation of cell line DC3F, Aug. 20, 2002, Colloids and Surfaces A: Physicochem. Eng. Aspects 214, 2003, Elsevier Science B.V. 2002, pp. 205-217.
Kassab, S. et al., Renal denervation attenuates the sodium retention and hypertension associated with obesity, Hypertension, 1995, 25:893-897.
Katholi, R.E. et al., Importance of the renal nerves in established two-kidney, one clip Goldblatt hypertension, Hypertension, 1982, 4 (suppl II):II-166-II-174.

Katholi, R.E. et al., Role of the renal nerves in the pathogenesis of one-kidney renal hypertension in the rat, Hypertension, 1981, 3(4) 404-409.
Katholi, R.E., Renal nerves and hypertension: an update, Fed Proc., 1985, 44:2846-2850.
Katholi, Richard E., Renal nerves in the pathogenesis of hypertension in experimental animals and humans, Am. J. Physiol. vol. 245, 1983, the American Physiological Society 1983, pp. F1-F14.
Kaye, D.M. et al., Functional and neurochemical evidence for partial cardiac sympathetic reinnervation after cardiac transplantation in humans, Circulation, 1993, vol. 88, pp. 1101-1109.
Kelleher, Catherine L. et al., Characteristics of Hypertension in Young Adults with Autosomal Dominant Polycystic Kidney Disease Compared with the General U.S. Population, Jun. 9, 2004, American Journal of Hypertension 2004, pp. 1029-1034.
King, Ronald W. P., Nerves in a Human Body Exposed to Low-Frequency Electromagnetic Fields, Jun. 7, 1999, IEEE Transactions on Biomedical Engineering, vol. 46, No. 12, Dec. 1999, IEEE 1999, pp. 1426-1431.
Kinney, Brian M., M.D., High-Tech Healing—The evolution of therapeutic electromagnetic fields in plastic surgery, Plastic Surgery Products, Jun. 2004, pp. 32-36, 3 pages.
Kirchheim, H. et al., Sympathetic modulation of renal hemodynamics, renin release and sodium excretion, Klin Wochenschr, 1989, 67:858-864.
Klein, K. et al., Impaired autofeedback regulation of hypothalamic norepinephrine release in experimental uremia. J Am Soc Nephrol. 2005;16:2081-7.
Knot, H. J. et al., Regulation of arterial diameter and wall [Ca2+] in cerebral arteries of rat by membrane potential and intravascular pressure. The Journal of Physiology. 1998. 508; pp. 199-209.
Kok, Lai Chow et al. Effect of Heating on Pulmonary Veins: How to Avoid Pulmonary Vein Stenosis. Journal of Cardiovascular Electrophysiology. vol. 14, No. 3, Mar. 2003. pp. 250-254.
Kok, R. J. et al., Specific Delivery of Captopril to the Kidney with the Prodrug Captopril-Lysozyme, Aug. 16, 1998, Journal of Pharmacology and Experimental Therapeutics, vol. 288, No. 1, 1999 by The American Society for Pharmacology and Experimental Therapeutics, pp. 281-285.
Kon, V. Neural Control of Renal Circulation, Miner Electrolyte Metab. 1989;15:33-43.
Koomans, H.A., et al., Sympathetic hyperactivity in chronic renal failure: a wake-up call. J Am Soc Nephrol. 2004;15:524-37.
Kopp, U. et al., Dietary sodium loading increases arterial pressure in afferent renal-denervated rats, Hypertension, 2003, 42:968-973.
Kopp, U.C. et al., Renal sympathetic nerve activity modulates afferent renal nerve activity by PGE2-dependent activation of alpha1- and alpha2-adrenoceptors on renal sensory nerve fibers. Am J Physiol Regul Integr Comp Physiol. 2007;293:R1561-72.
Koyama, Shozo et al., Relative Contribution of Renal Nerve and Adrenal Gland to Renal Vascular Tone During Prolonged Canine Hemorrhagic Hypotension, Sep. 24, 1992, Circulatory Shock 1993, vol. 39, Wiley-Liss, Inc. 1993, pp. 269-274.
Kozak, Lola Jean, Ph.D et al., National Hospital Discharge Survey: 2001 Annual Summary with Detailed Diagnosis and Procedure Data, Vital and Health Statistics, Serices 13 No. 156, Jun. 2004, CDC, 206 pages.
Kumagai, K. et al. New Approach to Pulmonary Vein Isolation for Atrial Fibrillation Using a Multielectrode Basket Catheter. Circulation Journal. 2006;70:88-93.
Lafayette, Richard A., M.D., How Does Knocking Out Angiotensin II Activity Reduce Renal Injury in Mice?, Jun. 14, 1999, Journal Club, American Journal of Kidney Diseases, vol. 35, No. 1, Jan. 2000, National Kidney Foundation, Inc. 2000, pp. 166-172.
Lavie, Peretz, Ph.D. and Victor Hoffstein, M.D., Sleep Apnea Syndrome: A Possible Contributing Factor to Resistant Hypertension, Jun. 2001, Sleep 2001, vol. 24, No. 6, pp. 721-725.
Le Noble, J.L. et al., Pharmacological evidence for rapid destruction of efferent renal nerves in rats by intrarenal infusion of 6-hydroxydopamine. J Hypertens Suppl. 1985;3:S137-40.
Lee, Michael A. (editor). SPORTSMed. Connecticut State Medical Society Committee on the Medical Aspects of Sports. Fall/Winter 2005. 10 pgs.

(56) References Cited

OTHER PUBLICATIONS

Lee, Raphael C. et al., Biophysical Injury Mechanisms in Electronic Shock Trauma, Annu. Rev. Biomed. Eng., 2000, vol. 2, Copyright © 2000 by Annual Reviews, pp. 477-509.

Lee, Raphael C. et al., Clinical Sequelae Manifested in Electrical Shock Survivors, Presentation by the Electrical Trauma Research Program, The University of Chicago, 37 pages Dec. 24, 2004.

Lee, Raphael C. et al., Membrane Biology and Biophysics, Chapter 25, Surgical Research, 2001 Academic Press, pp. 297-305.

Lee, Raphael C., M.D., Sc.D. and Michael S. Kolodney, S.B., Electrical Injury Mechanisms: Electrical Breakdown of Cell Membranes, Oct. 1, 1986, Plastic and Reconstructive Surgery, Nov. 1987, vol. 80, No. 5, pp. 672-679.

Lenoble, L.M. et al., Selective efferent chemical sympathectomy of rat kidneys. Am J Physiol. 1985;249:R496-501.

Ligtenberg, Gerry M.D. et al., Reduction of Sympathetic Hyperactivity by Enalapril in Patients with Chronic Renal Failure, Apr. 29, 1999, New England Journal of Medicine 1999, vol. 340, No. 17, 1999 Massachusetts Medical Society, pp. 1321-1328.

Lin, Vernon W. H. et al., High intensity magnetic stimulation over the lumbosacral spine evokes antinociception in rats, Apr. 16, 2002, Clinical Neurophysiology, vol. 113, 2002 Elsevier Science Ireland Ltd., pp. 1006-1012.

Lipfert, Peter, M.D. et al., Tachyphylaxis to Local Anesthetics Does Not Result form Reduced Drug Effectiveness at the Nerve Itself, Aug. 3, 1988, Anesthesiology 1989, vol. 70, pp. 71-75.

Lohmeier, Thomas E. and Drew A. Hildebrandt, Renal Nerves Promote Sodium Excretion in Angiotensin-Induced Hypertension, Oct. 20, 1997, Hypertension 1998, vol. 31, part 2, 1998 American Heart Association, Inc., pp. 429-434.

Lohmeier, Thomas E. et al., Prolonged Activation of the Baroreflex Produces Sustained Hypotension, Harry Goldblatt Award, Nov. 26, 2003, Hypertension 2004, vol. 43, Part 2, 2004 American Heart Association, Inc., pp. 306-311.

Lohmeier, Thomas E. et al., Renal Nerves Promote Sodium Excretion During Long-Term Increases in Salt Intake, Oct. 23, 1998, Hypertension 1999, vol. 33, part II, 1999 American Heart Association, Inc., pp. 487-492.

Lohmeier, Thomas E. et al., Sustained influence of the renal nerves to attenuate sodium retention in angiotensin hypertension, Apr. 13, 2001, Am J Physiol Regulatory Integrative Comp Physiol, vol. 281, 2001 the American Physiological Society, pp. R434-R443.

Lohmeier, Thomas E., et al., Baroreflexes prevent neurally induced sodium retention in angiotensin hypertension, American Journal Physiol Regulatory Integrative Comp Physiol, vol. 279, 2000 the American Physiological Society, pp. R1437-R1448.

Lohmeier, Thomas E., Interactions Between Angiotensin II and Baroreflexes in Long-Term Regulation of Renal Sympathetic Nerve Activity, Circulation Research, Jun. 27, 2003, American Heart Association, Inc.2003, pp. 1282-1284.

Luff, S.E. et al., Two types of sympathetic axon innervating the juxtaglomerular arterioles of the rabbit and rat kidney differ structurally from those supplying other arteries, May 1, 1991, Journal of Neurocytology 1991, vol. 20, 1991 Chapman and Hall Ltd., pp. 781-795.

Luippold, G. et al., Chronic renal denervation prevents glomerular hyperfiltration in diabetic rats, Nephrol Dial Transplant (2004) 19:342-347.

Lundborg, C. et al., Clinical experience using intrathecal (IT) bupivacaine infusion in three patients with complex regional pain syndrome type I (CRPS-I), Acta Anaesthesiol Scand 1999, vol. 43, pp. 667-678.

MacArthur, Dr. Alison, Spinal Anesthesia and Sever Gestational Hypertension, presentation at Mount Sinai Hospital, 25 pages.

Maeder, Micha, M.D. et al., Contrast Nephropathy: Review Focusing on Prevention, Jun. 22, 2004, Journal of the American College of Cardiology Nov. 2, 2004, vol. 44, No. 9, 2004 by the American College of Cardiology Foundation, pp. 1763-1771.

Malpas, Simon C., What sets the long-term level of sympathetic nerve activity: is there a role for arterial baroreceptors?, Invited Review, Am J Physiol Regul Integr Comp Physiol 2004, vol. 286, 2004 the American Physiological Society, pp. R1-R12.

Mancia, G., Grassi, G., Giannattasio, C., Seravalle, G., Sympathetic actrivation of pathogenesis of hypertension and progression of organ damage, Hypertension 1999, 34 (4 Pt 2): 724-728.

Marenzi, Giancarlo, M.D. et al., The Prevention of Radiocontrast-Agent-Induced Nephropathy by Hemofiltration, New England Journal of Medicine, Oct. 2, 2003, vol. 349 (14), 2003 Massachusetts Medical Society, pp. 1333-1340.

Market for infusion pumps grows with an aging population, NWL 97-01, The BBI Newsletter, vol. 20, No. 2, Feb. 1, 1997, American Health Consultants, Inc., 6 pages.

Martin, Jason B. et al., Gene Transfer to Intact Mesenteric Arteries by Electroporation, Mar. 27, 2000, Journal of Vascular Research 2000, vol. 37, 2000 S. Karger AG, Basel, pp. 372-380.

Mathur, Vandana S., Intra-Renal Drug Delivery for Fluid Overload, FlowMedica. Transcatheter Cardiovascular Therapeutics 2005. 31 slides.

McCreery, Douglas B. et al., Charge Density and Charge Per Phase as Cofactors in Neural Injury Induced by Electrical Stimulation, IEEE Transactions on Biomedical Engineering, vol. 17, No. 10, Oct. 1990, pp. 996-1000.

McCullough, Peter A., M.D., MPH et al., Acute Renal Failure after Coronary Intervention: Incidence, Risk Factors and Relationship to Mortality, Apr. 14, 1997, AM J Med. 1997, vol. 103, 1997 Excerpta Medica, Inc., pp. 368-375.

McMurray, John J.V., M.D. and Eileen O'Meara, M.D., Treatment of Heart Failure with Spironolactone—Trial and Tribulations, Aug. 5, 2004, New England Journal of Medicine, vol. 351, No. 6, 2004 Massachusetts Medical Society, pp. 526-528.

McRobbie, D. and M.A. Foster, Thresholds for biological effects of time-varying magnetic fields, Dec. 16, 1983, Clin. Phys. Physiol. Meas. 1984, vol. 5, No. 2, 1984 The Institute of Physics, pp. 67-78.

Medtronic Inc., MiniMed 2007, Implantable Insulin Pump System (Shoreview, MN) 4 pgs.

Medtronic Neurostimulation Systems, Expanding the Array of Pain Control Solutions, informational pamphlet, 1999 Medtronic, Inc., 6 pages.

Medtronic, Spinal Cord Stimulation, Patient Management Guidelines for Clinicians, Medtronic, Inc. 1999, 115 pages.

Medtronic, SynchroMed Infusion System—Clinical Reference Guide for Pain Therapy, Medtronic, Inc. 1998, 198 pages.

Mehran, Roxana, Renal insufficiency and contrast nephropathy: The most common, least understood risk factor, Cardiovascular Research Foundation. Columbia University Medical Center. 2005. 86 slides.

Mess, Sarah A., M.D. et al., Implantable Baclofen Pump as an Adjuvant in Treatment of Pressure Sores, Mar. 1, 2003, Annals of Plastic Surgery, vol. 51, No. 5, Nov. 2003, Lippincott Williams & Wilkins 2003, pp. 465-467.

Micro ETS Hyperhidrosis USA Hyperhidrosis USA. 2 pgs. <URL: http://www.hyperhidrosis-usa.com/Index.html>. Nov. 6, 2006.

Mihran, Richard T. et al., Temporally-Specific Modification of Myelinated Axon Excitability in Vitro Following a Single Ultrasound Pulse, Sep. 25, 1989, Ultrasound in Med. & Biol. 1990, vol. 16, No. 3, pp. 297-309.

Miklavčič, D. et al, A Validated Model of in Vivo Electric Field Distribution in Tissues for Electrochemotherapy and for DNA Electrotransfer for Gene Therapy, Biochimica et Biophysica Acta, 1523, 2000, pp. 73-83, <http:www.elsevier.com/locate/bba>.

Mitchell, G. A. G., The Nerve Supply of the Kidneys, Aug. 20, 1949, Acta Anatomica, vol. X, Fasc. ½, 1950, pp. 1-37.

Morrisey, D.M. et al., Sympathectomy in the treatment of hypertension: Review of 122 cases, Lancet. 1953;1:403-408.

Moss, Nicholas G., Renal function and renal afferent and efferent nerve activity, Am. J. Physiol. 1982, vol. 243, 1982 the American Physiological Society, pp. F425-F433.

Munglani, Rajesh, The longer term effect of pulsed radiofrequency for neuropathic pain, Jun. 8, 1998, Pain 80, 1999, International Association for the Study of Pain 1999, Published by Elsevier Science B.V., pp. 437-439.

Naropin (ropivacaine HCl) Injection, RX only Description, AstraZeneca 2001, 3 pages.

(56) References Cited

OTHER PUBLICATIONS

National High Blood Pressure Education Program, 1995 Update of the Working Group Reports on Chronic Renal Failure and Renovascular Hypertension, presentation, 13 pages.
National Kidney Foundation, Are You At Increased Risk for Chronic Kidney Disease?, 2002 National Kidney Foundation, Inc., 14 pages.
Nelson, L. et al., Neurogenic Control of Renal Function in Response to Graded Nonhypotensive Hemorrahage in Conscious Dogs, Sep. 13, 1992, Am J. Physiol. 264, 1993, American Physiological Society 1993, pp. R661-R667.
Nikolsky, Eugenia, M.D. et al., Radiocontrast Nephropathy: Identifying the High-Risk Patient and the Implications of Exacerbating Renal Function, Rev Cardiovasc Med. 2003, vol. 4, Supp. 1, 2003 MedReviews, LLC, pp. S7-S14.
Non-Final Office Action; U.S. Appl. No. 10/408,665; Mailed on Mar. 21, 2006, 14 pgs.
Non-Final Office Action; U.S. Appl. No. 11/129,765; Mailed on May 18, 2007, 10 pgs.
Non-Final Office Action; U.S. Appl. No. 11/129,765; Mailed on Sep. 10, 2007, 5 pgs.
Non-Final Office Action; U.S. Appl. No. 11/129,765; Mailed on Oct. 6, 2006, 30 pgs.
Non-Final Office Action; U.S. Appl. No. 11/133,925; Mailed on Oct. 8, 2008, 41 pgs.
Non-Final Office Action; U.S. Appl. No. 11/144,173; Mailed on Apr. 5, 2007, 33 pgs.
Non-Final Office Action; U.S. Appl. No. 11/144,173; Mailed on Sep. 10, 2007, 5 pgs.
Non-Final Office Action; U.S. Appl. No. 11/144,298; Mailed Oct. 29, 2009, 8 pgs.
Non-Final Office Action; U.S. Appl. No. 11/144,298; Mailed on Apr. 5, 2007, 33 pgs.
Non-Final Office Action; U.S. Appl. No. 11/144,298; Mailed on Sep. 10, 2007, 5 pgs.
Non-Final Office Action; U.S. Appl. No. 11/144,298; Mailed on Dec. 29, 2008, 7 pgs.
Non-Final Office Action; U.S. Appl. No. 11/145,122; Mailed on Apr. 11, 2007, 33 pgs.
Non-Final Office Action; U.S. Appl. No. 11/145,122; Mailed on Sep. 10, 2007, 5 pgs.
Non-Final Office Action; U.S. Appl. No. 11/189,563; Mailed on May 28, 2009, 5 pgs.
Non-Final Office Action; U.S. Appl. No. 11/233,814; Mailed on Jun. 17, 2008, 12 pgs.
Non-Final Office Action; U.S. Appl. No. 11/252,462; Mailed on Feb. 22, 2010, 6 pgs.
Non-Final Office Action; U.S. Appl. No. 11/266,993; Mailed on Jul. 8, 2009, 5 pgs.
Non-Final Office Action; U.S. Appl. No. 11/266,993; Mailed on Dec. 30, 2008, 7 pgs.
Non-Final Office Action; U.S. Appl. No. 11/363,867; Mailed on Sep. 25, 2008, 10 pgs.
Non-Final Office Action; U.S. Appl. No. 11/368,553; Mailed on May 18, 2010, 4 pgs.
Non-Final Office Action; U.S. Appl. No. 11/368,553; Mailed on Oct. 7, 2009, 5 pgs.
Non-Final Office Action; U.S. Appl. No. 11/368,809; Mailed on Dec. 3, 2009, 4 pgs.
Non-Final Office Action; U.S. Appl. No. 11/368,949; Mailed on Jun. 11, 2010, 6 pgs.
Non-Final Office Action; U.S. Appl. No. 11/368,971; Mailed on Aug. 24, 2010, 9 pgs.
Non-Final Office Action; U.S. Appl. No. 11/451,728; Mailed on Jun. 12, 2008, 41 pgs.
Non-Final Office Action; U.S. Appl. No. 11/451,728; Mailed on Jul. 2, 2009, 5 pgs.
Non-Final Office Action; U.S. Appl. No. 11/451,728; Mailed on Dec. 28, 2009, 7 pgs.
Non-Final Office Action; U.S. Appl. No. 11/504,117; Mailed on Mar. 31, 2009, 10 pgs.
Non-Final Office Action; U.S. Appl. No. 11/599,649; Mailed on Mar. 30, 2009, 10 pgs.
Non-Final Office Action; U.S. Appl. No. 11/599,649; Mailed on Jun. 23, 2008, 9 pgs.
Non-Final Office Action; U.S. Appl. No. 11/599,723; Mailed on Jun. 26, 2009, 17 pgs.
Non-Final Office Action; U.S. Appl. No. 11/599,723; Mailed on Oct. 15, 2010, 16 pgs.
Non-Final Office Action; U.S. Appl. No. 11/599,882; Mailed on Jul. 6, 2009, 13 pgs.
Non-Final Office Action; U.S. Appl. No. 11/688,178; Mailed on Jun. 28, 2010, 5 pgs.
Non-Final Office Action; U.S. Appl. No. 11/840,142; Mailed on Apr. 3, 2009, 13 pgs.
Non-Final Office Action; U.S. Appl. No. 12/567,521; Mailed on Sep. 3, 2010, 9 pgs.
Non-Final Office Action; U.S. Appl. No. 12/616,708; Mailed Sep. 16, 2010, 10 pgs.
Non-Final Office Action; U.S. Appl. No. 12/725,375; Mailed on Oct. 12, 2010, 14 pgs.
Nozawa, T. et al., Effects of Long Term Renal Sympathetic Denervation on Heart Failure After Myocardial Infarction in Rats, Sep. 22, 2001, Heart Vessels, 2002, 16, Springer-Verlag 2002, pp. 51-56.
O'Hagan, K.P. et al., Renal denervation decreases blood pressure in DOCA-treated miniature swine with established hypertension, Am J Hypertens., 1990, 3:62-64.
Onesti, G. et al., Blood pressure regulation in end-stage renal disease and anephric man, Circ Res Suppl., 1975, 36 & 37: 145-152.
Osborn, et al., Effect of renal nerve stimulation on renal blood flow autoregulation and antinatriuresis during reductions in renal perfusion pressure, in Proceedings of the Society for Experimental Biology and Medicine, vol. 168, 77-81, 1981. (Abstract).
Packer, Douglas L. et al., Clinical Presentation, Investigation, and Management of Pulmonary Vein Stenosis Complication Ablation for Atrial Fibrillation, Circulation: Journal of the American Heart Association. Feb. 8, 2005. pp. 546-554.
Page, I.H. et al., The Effect of Renal Denervation on the Level of Arterial Blood Pressure and Renal Function in Essential Hypertension. J Clin Invest. 1935;14:27-30.
Page, I.H., et al., The Effect of Renal Efficiency of Lowering Arterial Blood Pressure in Cases of Essential Nephritis, Hospital of the Rockefeller Institue, Jul. 12, 1934, 7 pgs.
Palmer, Biff, F., M.D., Managing Hyperkalemia Caused by Inhibitors of the Renin-Angiotensin-Aldosterone System, Aug. 5, 2004, The New England Journal of Medicine 2004, vol. 351;6, 2004 Massachusetts Medical Society, pp. 585-592.
Pappone, Carlo et al., [2005][P2-70] Safety Report of Circumferential Pulmonary Vein Ablation. A 9-Year Single-Center Experience on 6,442 Patients with Atrial Fibrillation, Abstract only. 1 page, May 2005.
Pappone, Carlo et al., [2004][759] Pulmonary Vein Denervation Benefits Paroxysmal Atrial Fibrillation Patients after Circumferential Ablation, Abstract only. 1 page, Jan. 5, 2004.
Pappone, Carol and Santinelli, Vincenzo. Multielectrode basket catheter: A new tool for curing atrial fibrillation? Heart Rhythm, vol. 3, Issue 4, pp. 385-386. Apr. 2006.
Peacock, J.M. and R. Orchardson, Action potential conduction block of nerves in vitro by potassium citrate, potassium tartrate and potassium oxalate, May 6, 1998, Journal of Clinical Periodontology, Munksgaard 1999, vol. 26, pp. 33-37.
Petersson, M. et al., Long-term outcome in relation to renal sympathetic activity in patients with chronic heart failure. Eur Heart J. 2005;26:906-13.
Pettersson, A. et al., Renal interaction between sympathetic activity and ANP in rats with chronic ischaemic heart failure, Nov. 25, 1988, Acta Physiol Scand 1989, 135, pp. 487-492.
*PHCL 762 Pharmacology of the Autonomic Nervous System*, Chapter 2 and 6.8 in Mosby, http://www.kumc.edu/research/medicine/pharmacology/CAI/phcl762.html, last accessed Aug. 24. 2004, 14 pgs.
Pitt, B. et al., Effects of Eplerenone, Enalapril, and Eplerenone/Enalapril in Patients With Essential Hypertension and Left

(56) References Cited

OTHER PUBLICATIONS

Ventricular Hypertrophy: The 4E-Left Ventricular Hypertrophy Study, Circulation, 2003, vol. 108, pp. 1831-1838.
Pliquett, U., Joule heating during solid tissue electroporation, Oct. 22, 2002, Med. Biol. Eng. Comput., 2003, vol. 41, pp. 215-219.
Podhajsky R.J. et al, The Histologic Effects of Pulsed and Continuous Radiofrequency Lesions at 42 C to Rat Dorsal Root Ganglion and Sciatic Nerve, Spine, vol. 30, No. 9, pp. 1008-1013, 2005, Lippincott Williams & Wilkins Inc.
Pope, Jill. Fixing a Hole: Treating Injury by Repairing Cells. The New York Academy of Sciences. Jul. 6, 2006. 6 pgs.
Popovic, Jennifer R. and Margaret J. Hall, 1999 National Hospital Discharge Survey, Apr. 24, 2001, Advance Data, No. 319, CDC, pp. 1-17 & 20.
Practice Guidelines Writing Committee and ESH/ESC Hypertension Guidelines Committee, Practice Guidelines for Primary Care Physicians: 2003 ESH/ESC Hypertension Guidelines, Published in Journal of Hypertension 2003, vol. 21, No. 10: 1011-1053, European Society of Hypertension 2003, pp. 1779-1786.
Programmable Infusion System, Pumps and Pump Selection, Medtronic Pain Therapies, Medtronic, Inc. Sep. 5, 2001, 2 pgs.
Pucihar, Gorazd et al., The influence of medium conductivity on electropermeabilization and survival of cells in vitro, May 31, 2001, Bioelectrochemistry, vol. 54, 2001, Elsevier Science B.V. 2001, pp. 107-115.
*Pulmonary Concepts in Critical Care Breath Sounds*. http://rnbob.tripod.com/breath.htm. last accessed Aug. 23, 2004, 5 pages.
*Pulmonary Function Testing*, http://jan.ucc.nau.edu/~daa/lecture/pft.htm, last accessed Aug. 23, 2004, 8 pages.
Purerfellner, Helmut and Martinek, Martin. Pulmonary vein stenosis following catheter ablation of atrial fibrillation. Current Opinion in Cardiology. 20; pp. 484-490. 2005.
Purerfellner, Helmut et al., Pulmonary Vein Stenosis by Ostial Irrigated-Tip Ablation: Incidence, Time Course, and Prediction, Journal of Cardiovascular Electrophysiology. vol. 14, No. 2, Feb. 2003. pp. 158-164.
Raji, A. R. M. and R. E. M. Bowden, Effects of High-Peak Pulsed Electromagnetic Field on the Degeneration and Regeneration of the Common Peroneal Nerve in Rats, The Journal of Bone and Joint Surgery Aug. 1983, vol. 65-B, No. 4, 1983 British Editorial Society of Bone and Joint Surgery, pp. 478-492.
Ram, C. Venkata S., M.D., Understanding refractory hypertension, May 15, 2004, Patient Care May 2004, vol. 38, pp. 12-16, 7 pages from http://www.patientcareonline.com/patcare/content/printContentPopup.jsp?id=108324.
Ravalia, A. et al., Tachyphylaxis and epidural anaesthesia, Edgware General Hospital, Correspondence, p. 529, Jun. 1989.
Renal Parenchymal Disease, Ch. 26, 5th Edition Heart Disease, A Textbook of Cardiovascular Medicine vol. 2, Edited by Eugene Braunwald, WB Saunders Company, pp. 824-825 1997.
Ribstein, Jean and Michael H. Humphreys, Renal nerves and cation excretion after acute reduction in functioning renal mass in the rat, Sep. 22, 1983, Am. J. Physiol., vol. 246, 1984 the American Physiological Society, pp. F260-F265.
Richebe, Philippe, M.D. et al., Immediate Early Genes after Pulsed Radiofrequency Treatment: Neurobiology in Need of Clinical Trials, Oct. 13, 2004, Anesthesiology Jan. 2005, vol. 102, No. 1, 2004 American Society of Anesthesiologists, Inc. Lippincott Williams & Wilkins, Inc., pp. 1-3.
Rihal, Charanjit S. et al., Incidence and Prognostic Importance of Acute Renal Failure After Percutaneous Coronary Intervention, Mar. 6, 2002, Circulation May 14, 2002, vol. 10, 2002 American Heart Association, Inc., pp. 2259-2264.
Rosen, S.M. et al., Relationship of Vascular Reactivity to Plasma Renin Concentration in Patients with Terminal Renal Failure, Proc. Dialysis Transplant Forum 1974, pp. 45-47.
Roth, Bradley J. and Peter J. Basser, A Model of the Stimulation of a Nerve Fiber by Electromagnetic Induction, IEEE Transactions on Biomedical Engineering, vol. 37, No. 6, Jun. 1990, pp. 588-597.
Rudin, Asa, M.D. et al., Postoperative Epidural or Intravenous Analgesia after Major Abdominal or Thoraco-Abdominal Surgery, The Journal of the American Society of Anesthesiologists, Inc., Anesthesiology 2001, vol. 95, A-970, 1 page.
Rudnick, Michael R. et al., Contrast-induced nephropathy: How it develops, how to prevent it, Cleveland Clinic Journal of Medicine Jan. 2006, vol. 73, No. 1, pp. 75-87.
Rump, L.C., The Role of Sympathetic Nervous Activity in Chronic Renal Failure, J Clinical Basic Cardiology 2001, vol. 4, pp. 179-182.
Ruohonen, Jarmo et al., Modeling Peripheral Nerve Stimulation Using Magnetic Fields, Journal of the Peripheral Nervous System, vol. 2, No. 1, 1997, Woodland Publications 1997, pp. 17-29.
Saad, Eduardo B. et al., Pulmonary Vein Stenosis After Radiofrequency Ablation of Atrial Fibrillation: Functional Characterization, Evolution, and Influence of the Ablation Strategy, Circulation. 108; pp. 3102-3107. 2003.
Sabbah, Hani N., Animal Models for Heart Failure and Device Development, Henry Ford Health System. 24 slides, Oct. 17, 2005.
Schauerte, P et al., Focal atrial fibrillation: experimental evidence for a pathophysiologic role of the autonomic nervous system, Journal of Cardiovascular Electrophysiology. 12(5). May 2001. Abstract only. 2 pgs.
Schauerte, P et al., Catheter ablation of cardiac autonomic nerves for prevention of vagal atrial fibrillation, Circulation. 102(22). Nov. 28, 2000. Abstract only. 2 pgs.
Schauerte, P et al., Transvenous parasympathetic nerve stimulation in the inferior vena cava and atrioventricular conduction, Journal of Cardiovascular Electrophysiology. 11(1). Jan. 2000. Abstract only. 2 pgs.
Scheiner, Avram, Ph.D., The design, development and implementation of electrodes used for functional electrial stimulation, Thesis paper, Case Western Reserve University, May 1992, 220 pages.
Scherlag, BJ and Po, S., The intrinsic cardiac nervous system and atrial fibrillation, Current Opinion in Cardiology. 21(1):51-54, Jan. 2006. Abstract only. 2 pgs.
Schlaich, M.P. et al., Relation between cardiac sympathetic activity and hypertensive left ventricular hypertrophy. Circulation. 2003;108:560-5.
Schlaich, M.P. et al., Sympathetic augmentation in hypertension: role of nerve firing, norepinephrine reuptake, and angiotensin neuromodulation, Hypertension, 2004, 43:169-175.
Schmitt, Joseph et al., Intravascular Optical Coherence Tomography—Opening a Window into Coronary Artery Disease, LightLab Imaging, Inc. Business Briefing: European Cardiology 2005.
Schoenbach, Karl H. et al, Intracellular Effect of Ultrashort Electrical Pulses, Dec. 26, 2000, Bioelectromagnetics, vol. 22, 2001, Wiley-Liss, Inc. 2001, pp. 440-448.
Schrier, Robert et al., Cardiac and Renal Effects of Standard Versus Rigorous Blood Pressure Control in Autosomal-Dominant Polycistic Kidney Disease, Mar. 23, 2002, Journal of the American Society of Nephrology, American Society of Nephrology 2002, pp. 1733-1739.
Scremin, Oscar U., M.D., Ph.D. and Daniel P. Holschneider, M.D., 31 & 32.. An Implantable Bolus Infusion Pump for the Neurosciences, FRP, 04-05, 3 pages, Apr. 2005.
Sensorcaine—MPF Spinal Injection, informational document, AstraZeneca 2001, 2 pgs.
Serrador, Jorge M., Autonomic Regulation of the Cardiovascular System, MIT Lecture. 8 pages, 48 slides.
Shah, D.C., Haissaguerre, M., Jais, P., Catheter ablation of pulmonary vein foci for atrial fibrillation: pulmonary vein foci ablation for atrial fibrillation, Thorac Cardiovasc Surg, 1999, 47 (suppl. 3): 352-356.
Shannon, J.L. et al., Studies on the innervation of human renal allografts, J Pathol. 1998, vol. 186, pp. 109-115.
Shlipak, M.G. et al., The clinical challenge of cardiorenal syndrome. Circulation. 2004;110:1514-7.
Shupak, Naomi M., Therapeutic Uses of Pulsed Magnetic-Field Exposure: A Review, Radio Science Bulletin Dec. 2003, No. 307, pp. 9-32.
Shu-Qing, Liu et al., Old spinal cord injury treated by pulsed electric stimulation, General Hospital of Beijing Command, Beijing, 5 pages (full article in Chinese; abstract on last page) Dec. 6, 1990.

(56) References Cited

OTHER PUBLICATIONS

Siegel, RJ et al., Clinical demonstration that catheter-delivered ultrasound energy reverses arterial vasoconstriction, Journal of the American College of Cardiology. 1992. 20; 732-735. Summary only. 2 pgs.
Simpson, B. et al., Implantable spinal infusion devices for chronic pain and spasticity: an accelerated systematic review, ASERNIP-S Report No. 42, Adelaide, South Australia, ASERNIP-S, May 2003, 56 pages.
Sisken, B.F. et al., 229.17 Influence of Non-Thermal Pulsed Radiofrequency Fields (PRF) on Neurite Outgrowth, Society for Neuroscience, vol. 21, 1995, 2 pages.
Skeie, B. et al., Effect of chronic bupivacaine infusion on seizure threshold to bupivacaine, Dec. 28, 1986, Acta Anaesthesiol Scand 1987, vol. 31, pp. 423-425.
Skopec M., *A Primer on Medical Device interactions with Magnetic Resonance Imaging Systems*, Feb. 4, 1997, CDRH Magnetic Resonance Working Group, U.S. Department of Heatlh and Human Services, Food and Drug Administration Center for Devices and Radiological Health, Updated May 23, 1997, 17 pages, http://www.fda.gov/cdrh/ode/primerf6.html, (last accessed Jan. 23, 2006.
Slappendel, Robert et al., The efficacy of radiofrequency lesioning of the cervical spinal dorsal root ganglion in a double blinded randomized study, Jun. 26, 1997, Pain 73, 1997 International Association for the Study of Pain, Elsevier Science B.V., pp. 159-163.
Sluijter, M.D., Ph.D., Pulsed Radiofrequency, May 17, 2005, Anesthesiology Dec. 2005, vol. 103, No. 6, 2005 American Society of Anesthesiologists, Inc. Lippincott Williams & Wilkins, Inc., pp. 1313-1314.
Sluijter, M.D., Ph.D., Radiofrequency Part 1: The Lumbosacral Region, Chapter 1 Mechanisms of Chronic Pain and part of Chapter 2 Spinal Pain, 2001 FlivoPress SA, Meggen (LU), Switzerland, pp. 1-26.
Sluijter, M.D., Ph.D., Radiofrequency Part 2: Thoracic and Cervical Region, Headache and Facial Pain, various pages from, FlivoPress SA, Meggen (LU), Switzerland, 13 pages 2002.
Sluijter, M.D., Ph.D., The Role of Radiofrequency in Failed Back Surgery Patients, Current Review of Pain 2000, vol. 4, 2000 by Current Science Inc., pp. 49-53.
Smithwick, R.H. et al., Hypertension and associated cardiovascular disease: comparison of male and female mortality rates and their influence on selection of therapy, JAMA, 1956, 160:1023-1033.
Smithwick, R.H. et al., Splanchnicectomy for essential hypertension, Journal Am Med Assn, 1953;152:1501-1504.
Smithwick, R.H., Surgical treatment of hypertension, Am J Med 1948, 4:744-759.
Sobotka, Paul A., Treatment Strategies for Fluid Overload, CHF Patients, CHF Solutions. Transcatheter Cardiovascular Therapeutics 2005. 20 slides.
Solis-Herruzo, J.A. et al., Effects of lumbar sympathetic block on kidney function in cirrhotic patients with hepatorenal syndrome, Journal of Hepatology, 1987; 5: 167-173.
Souza, D.R.B. et al., Chronic experimental myocardial infarction produces antinatriuresis by a renal nerve-dependent mechanism, Oct. 14, 2003, Brazilian Journal of Medical and Biological Research 2004, vol. 37, pp. 285-293.
Standl, Thomas, M.D., et al., Patient-controlled epidural analgesia reduces analgesic requirements compared to continuous epidural infusion after major abdominal surgery, Aug. 29, 2002, Canada Journal of Anesthesia 2003, vol. 50 (3), pp. 258-264.
Steffen, W. et al., Catheter-delivered high intensity, low frequency ultrasound induces vasodilation in vivo, European Heart Journal. 1994. 15;pp. 369-376.
Steg, PG et al., Pulsed ultraviolet laser irradiation produces endothelium-independent relaxation of vascular smooth muscle, Circulation: Journal of the American Heart Association. 1989. pp. 189-197.
Stone, Gregg W., M.D. et al., Fenoldopam Mesylate for the Prevention of Contrast-Induced Nephropathy, JAMA Nov. 5, 2003, vol. 290, No. 17, 2003 American Medical Association, pp. 2284-2291.

Strojek, K. et al., Lowering of microalbuminuria in diabetic patients by a sympathicoplegic agent: novel approach to prevent progression of diabetic nephropathy? J Am Soc Nephrol. 2001;12:602-5.
Summary, Critical Reviews in Biomedical Engineering, vol. 17, Issue 5, 1989, pp. 515-529.
Sung, Duk Hyun, M.D. et al., Phenol Block of Peripheral Nerve Conduction: Titrating for Optimum Effect, Jun. 27, 2000, Arch. Phys. Med. Rehabil. vol. 82, May 2001, pp. 671-676.
Taka, Tomomi et al., Impaired Flow-Mediated Vasodilation in vivo and Reduced Shear-Induced Platelet Reactivity in vitro in Response to Nitric Oxide in Prothrombotic, Stroke-Prone Spontaneously Hypertensive Rats, Pathophysiology of Haemostasis and Thrombosis. Dec. 23, 2002. pp. 184-189.
Taler, Sandra J. et al., Resistant Hypertension, Comparing Hemodynamic Management to Specialist Care, Mar. 12, 2002, Hypertension 2002, vol. 39, 2002 American Heart Association, Inc., pp. 982-988.
Tamborero, David et al., Incidence of Pulmonary Vein Stenosis in Patients Submitted to Atrial Fibrillation Ablation: A Comparison of the Selective Segmental Ostial Ablation vs. the Circumferential Pulmonary Veins Ablation, Journal of Intervocational Cardiac Electrophysiology. 14; pp. 41-25. 2005.
Tay, Victoria KM, et al., Computed tomography fluoroscopy-guided chemical lumbar sympathectomy: Simple, safe and effective, Oct. 31, 2001, Diagnostic Radiology, Australasian Radiology 2002, vol. 46, pp. 163-166.
Terashima, Mitsuyasu et al. Feasibility and Safety of a Novel CryoPlasty™ System. Poster. 1 page, Mar. 15, 2002.
Thatipelli et al., CT Angiography of Renal Artery Anatomy for Evaluating Embolic Protection Devices, Journal of Vascular and Interventional Radiology, Jul. 2007, pp. 842-846.
The Antihypertensive and Lipid-Lowering Treatment to Prevent Heart Attack Trial, ALLHAT Research Group, JAMA, 2002, vol. 288, pp. 2981-2997.
Thomas, John R. and Oakley, E. Howard N. Chapter 15: Nonfreezing Cold Injury Medical Aspects of Harsh Environments, vol. 1. pp. 467-490, 2001.
Thompson, Gregory W., et al., Bradycardia Induced by Intravascular Versus Direct Stimulation of the Vagus Nerve, Aug. 24, 1997, The Society of Thoracic Surgeons 1998, pp. 637-642.
Thrasher, Terry N., Unloading arterial baroreceptors causes neurogenic hypertension, Dec. 4, 2001, Am J. Physiol Regulatory Integrative Comp Physiol, vol. 282, 2002 the American Physiological Society, pp. R1044-R1053.
Tokuno, Hajime A. et al., Local anesthetic effects of cocaethylene and isopropylcocaine on rat peripheral nerves, Oct. 7, 2003, Brain Research 996, 2004, Elsevier B.V. 2003, pp. 159-167.
Trapani, Angelo J. et al., Neurohumoral interactions in conscious dehydrated rabbit, Am. J. Physiol. 254, 1988, the American Physiological Society 1988, pp. R338-R347.
Trock, David H. et al., The Effect of Pulsed Electromagnetic Fields in the Treatment of Osteoarthritis of the Knee and Cervical Spine. Report of Randomized, Double Blind, Placebo Controlled Trials, Mar. 22, 1994, The Journal of Rheumatology 1994, vol. 21, pp. 1903-1911.
Troiano, Gregory C. et al., The Reduction in Electroporation Voltages by the Addition of a Surfactant to Planar Lipid Bilayers, May 12, 1998, Biophysical Journal, vol. 75, Aug. 1998, the Biophysical Society 1998, pp. 880-888.
Trumble, Dennis R. and James A. MaGovern, Comparison of Dog and Pig Models for Testing Substernal Cardiac Compression Devices, Nov. 2003, ASAIO Journal 2004, pp. 188-192.
Tsai, E., Intrathecal drug delivery for pain indications, technique, results, Pain Lecture presentation, Jun. 8, 2001, 31 pages.
Uematsu, Toshihiko, M.D., Ph.D., F.I.C.A. et al., Extrinsic Innervation of the Canine Superior Vena Cava, Pulmonary, Portal and Renal Veins, Angiology—Journal of Vascular Diseases, Aug. 1984, pp. 486-493.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.

(56) References Cited

OTHER PUBLICATIONS

Upadhyay, Pramod, Electroporation of the skin to deliver antigen by using a piezo ceramic gas igniter, Jan. 27, 2001, International Journal of Pharmaceutics, vol. 217, 2001 Elsevier Science B.V., pp. 249-253.
Valente, John F. et al., Laparoscopic renal denervation for intractable ADPKD-related pain, Aug. 24, 2000, Nephrol Dial Transplant 2001, vol. 16, European Renal Association-European Dialysis and Transplant Association, p. 160.
Van Antwerp, Bill and Poonam Gulati, Protein Delivery from Mechanical Devices Challenges and Opportunities, Medtronic presentation, 19 pages, Jul. 2003.
Velazquez, Eric J., An international perspective on heart failure and left ventricular systolic dysfunction complicating myocardial infarction: the VALIANT registry, Aug. 5, 2004, European Heart Journal vol. 25, 2004 Elsevier, pp. 1911-1919.
Velez-Roa, Sonia, M.D. et al., Peripheral Sympathetic Control During Dobutamine Infusion: Effects of Aging and Heart Failure, Jul. 7, 2003, Journal of the American College of Cardiology, vol. 42, No. 9, 2003, American College of Cardiology Foundation 2003, pp. 1605-1610.
Vigilance, Deon W. et al., A Novel Approach to Increase Total Urine Output in Acute Heart Failure: Unilateral Renal Nerve Blockade, RNB Abstract AHA, 2 pages.
Villarreal, Daniel et al., Effects of renal denervation on postprandial sodium excretion in experimental heart failure, Oct. 29, 1993, Am J Physiol 266, 1994, pp. R1599-R1604.
Villarreal, Daniel et al., Neurohumoral modulators and sodium balance in experimental heart failure, Nov. 6, 1992, Am. J. Physiol, vol. 264, 1993, pp. H1187-H1193.
Vince, D. Geoffrey. Virtual Histology: A new technique for the assessment of plaque composition. The Cleveland Clinic Foundation. 28 pgs.
Vonend, O. et al., Moxonidine treatment of hypertensive patients with advanced renal failure. J Hypertens. 2003;21:1709-17.
Wagner, C.D. et al., Very low frequency oscillations in arterial blood pressure after autonomic blockade in conscious dogs, Feb. 5, 1997, Am J Physiol Regul Integr Comp Physiol 1997, vol. 272, 1997 the American Physiological Society, pp. 2034-2039.
Wald, Jan D., Ph.D, et al., Cardiology Update: 2003, Sep. 11, 2003, AG Edwards 2003, 120 pages.
Wang, Xi et al., Alterations of adenylyl cyclase and G proteins in aortocaval shunt-induced heart failure, Jul. 2004, AM J Physiol Heart Circ Physiol vol. 287, 2004 the American Physiological Society, pp. H118-H125.
Weaver, James C., Chapter 1 Electroporation Theory, Concepts and Mechanisms, Methods in Molecular Biology, vol. 55, Plant Cell Electroporation and Electrofusion Protocols, Edited by J.A. Nickoloff, Humana Press Inc., pp. 3-28, 1995.
Weaver, James C., Electroporation: A General Phenomenon for Manipulating Cells and Tissues, Oct. 22, 1992, Journal of Cellular Biochemistry, vol. 51, 1993 Wiley-Liss, Inc., pp. 426-435.
Weiner, Richard L., M.D., Peripheral nerve neurostimulation, Neurosurg. Clin. N. Am. vol. 14, 2003, Elsevier, Inc. 2003, pp. 401-408.
Weisbord, Steven D., M.D. and Paul M. Palevsky, M.D., Radiocontrast-Induced Acute Renal Failure, Jul. 10, 2004, Journal of Intensive Care Medicine 2005, vol. 20 (2), 2005 Sage Publications, pp. 63-75.
Whitelaw, G.P., Kinsey, D., Smithwick, R.H., Factors influencing the choice of treatment in essential hypertension: surgical, medical, or a combination of both, Am J Surg, 1964, 107:220-231.
Wilson, D.H. et al., The Effects of Pulsed Electromagnetic Energy on Peripheral Nerve Regeneration, Annals New York Academy of Sciences, pp. 575-585, Oct. 1974.
Wolinsky, Harvey, M.D. PhD and Swan N. Thung, M.D., Use of a Perforated Balloon Catheter to Deliver Concentrated Heparin Into the Wall of the Normal Canine Artery, Aug. 30, 1989, JACC 1990, vol. 15, 1990 by the American College of Cardiology, pp. 475-481.

Wyss, J. Michael et al., Neuronal control of the kidney: Contribution to hypertension, Apr. 8, 1991, Can. J. Physiol. Pharmacol. 1992;70: 759-770.
Yamaguchi, Jun-ichi, M.D. et al., Prognostic Significance of Serum Creatinine Concentration for In-Hospital Mortality in Patients with Acute Myocardial Infarction Who Underwent Successful Primary Percutaneous Coronary Intervention (from the Heart Institute of Japan Acute Myocardial Infarction [HIJAMI] Registry), Feb. 24, 2004, The American Journal of Cardiology vol. 93, Jun. 15, 2004, 2004 by Excerpta Medica, Inc., pp. 1526-1528.
Ye, Richard D., M.D., Ph.D., Pharmacology of the Peripheral Nervous System, E-425 MSB, 6 pages, Jan. 2000.
Ye, S. et al., A limited renal injury may cause a permanent form of neurogenic hypertension. Am J Hypertens. 1998;11:723-8.
Ye, Shaohua et al., Renal Injury Caused by Intrarenal Injection of Pheno Increases Afferent and Efferent Renal Sympathetic Nerve Activity, Mar. 12, 2002, American Journal of Hypertension, Aug. 2002, vol. 15, No. 8, 2002 the American Journal of Hypertension, Ltd. Published by Elsevier Science Inc., pp. 717-724.
Yong-Quan, Dong et al., The therapeutic effect of pulsed electric field on experimental spinal cord injury, Beijing Army General Hospital of People's Liberation Army, Beijing, 5 pages (full article in Chinese; abstract on last page) Mar. 30, 1992.
Young, James B., M.D., FACC, Management of Chronic Heart Failure: What Do Recent Clinical Trials Teach Us?, Reviews in Cardiovascular Medicine, vol. 5, Suppl. 1, 2004, MedReviews, LLC 2004, pp. S3-S9.
Yu, Wen-Chung et al. Acquired Pulmonary Vein Stenosis after Radiofrequency Catheter Ablation of Paroxysmal Atrial Fibrillation. Journal of Cardiovascular Electrophysiology. vol. 12, No. 8. Aug. 2001. pp. 887-892.
Zanchetti, A. et al., Neural Control of the Kidney—Are There Reno-Renal Reflexes?, Clin. And Exper. Hyper. Theory and Practice, A6 (1&2), 1984, Marcel Dekker, Inc. 1984, pp. 275-286.
Zanchetti, A. et al., Practice Guidelines for Primary Care Physicians: 2003 ESH/ESC Hypertension Guidelines, Journal of Hypertension, vol. 21, No. 10, 2003, pp. 1779-1786.
Zanchetti, A.S., Neural regulation of renin release: Experimental evidence and clinical implications in arterial hypertension, Circulation, 1977, 56(5) 691-698.
Zimmermann, Ulrich, Electrical Breakdown, Electropermeabilization and Electrofusion, Rev. Physiol. Biochem. Pharmacol., vol. 105, Springer-Verlag 1986, pp. 175-256.
Zoccali, C. et al., Plasma norepinephrine predicts survival and incident cardiovascular events in patients with end-stage renal disease. Circulation. 2002;105:1354-9.
Zucker, Irving H. et al., The origin of sympathetic outflow in heart failure: the roles of angiotensin II and nitric oxide, Progress in Biophysics & Molecular Biology, vol. 84, 2004, Elsevier Ltd. 2003, pp. 217-232.
Zundert, Jan Van, M.D. FIPP and Alex Cahana, M.D. DAAPM, Pulsed Radiofrequency in Chronic Pain Management: Looking for the Best Use of Electrical Current, Pain Practice 2005, vol. 5, Issue 2, 2005 World Institute of Pain, pp. 74-76.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
Avitall et al., "The creation of linear contiguous lesions in the atria with an expandable loop catheter," Journal of the Americam College of Cardiology, 1999; 33; pp. 972-984.
Benito, F., et al. "Radiofrequency cateheter ablation of accessory pathways in infants." Heart, 78:160-162 (1997).
Dubuc, M., et al., "Feasibility of cardiac cryoablation using a transvenous steerable electrode catheter." J Interv Cardiac Electrophysiol, 2:285-292 (1998).

(56) References Cited

OTHER PUBLICATIONS

Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Han, Y.-M, et al., "Renal artery ebolization with diluted hot contrast medium: An experimental study." J Vasc Interv RadioI, 12: 862-868 (2001).
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Lustrgarten, D.L.,et al., "Cryothermal ablation: Mechanism of tissue injury and current experience in the treatment of tachyarrhythmias." Progr Cardiovasc Dis, 41:481-498 (1999).
Oliverira, V., et al., "Renal denervation normalizes pressure and baroreceptor reflex in high renin hypertension in conscious rats." Hypertension, 19:II-17-II-21 (1992).
Opposition to European Patent No. EP2092957, Granted Jan. 5, 2011, Date of Opposition Oct. 5, 2011, 26 pages.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Peet, M., "Hypertension and its Surgical Treatment by bilateral supradiaphragmatic splanchnicectomy" Am J Surgery (1948) pp. 48-68.
Schauerte, P., et al. "Catheter ablation of cardiac autonomic nerves for prevention of vagal atrial fibrillation." Circulation, 102:2774-2780 (2000).
Stella, A., et al., "Effects of reversible renal deneravation on haemodynamic and excretory functions on the ipsilateral and contralateral kidney in the cat." Hypertension, 4:181-188 (1986).
Swartz, J.F., et al., "Radiofrequency endocardial cateheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Weinstock, M., et al., "Renal denervation prevents sodium rentention and hypertension in salt sensitive rabbits with genetic baroreflex impairment." Clinical Science, 90:287-293 (1996).
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardian Electrophysiology, 2001, pp. 401-410.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life- Investor Relations, Nov. 8, 2012, 2 pages, <http://phx.corporate-ir.net/phoenix.zhtml?c=62272&p=irol-newsArticle&id=1756108>.

"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison AwardsTM" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global SYMPLICITY registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Final Office Action; U.S. Appl. No. 12/827,700; Mailed on Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gertner, Jon, "Meet the Tech Duo That's Revitalizing the Medical Device Industry." Fast Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).

(56) References Cited

OTHER PUBLICATIONS

Hering, Dagmara et al., "Chronic kidney disease: role of sympathetic nervous system activation and potential benefits of renal denervation." EuroIntervention, vol. 9, 2013, 9 pages.
Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Linz, Dominik et al., "Renal denervation suppresses ventricular arrhythmias during acute ventricular ischemia in pigs." Heart Rhythm, vol. 0, No. 0, 2013, 6 pages.
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Millard, F. C., et al, "Renal Embolization for ablation of function in renal failure and hypertension." Postgraduate Medical Journal, 65, 729-734, (1989).
Ormiston, John et al., "First-in-human use of the OneShotTM renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Stouffer, G. A. et al., Journal of Molecular and Cellular Cardiology, vol. 62, 2013, 6 pages.
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Oz, Mehmet, Pressure Relief, TIME, Jan. 9, 2012, 2 pages. <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Schneider, Peter A., "Endovascular Skills—Guidewire and Catheter Skills for Endovascular Surgery," Second Edition Revised and Expanded, 10 pages, (2003).
Tsao, Hsuan-Ming, Evaluation of Pulmonary Vein Stenosis after Catheter Ablation of Atrial Fibrillation, Cardiac Electrophysiology Review, 6, 2002, 4 pages.
European Search Report for Application No. 10159584.1, Date of Mailing: Jun. 10, 2013, 9 pages.

\* cited by examiner

ULTRASOUND APPARATUSES FOR THERMALLY-INDUCED RENAL NEUROMODULATION

REFERENCE TO RELATED APPLICATIONS

The present application is a continuation of U.S. patent application No. 11/840,142, filed Aug. 16, 2007, now U.S. Pat. No. 7,717,948 which is a continuation of U.S. patent application Ser. No. 11/504,117, filed Aug. 14, 2006, now U.S. Pat. No. 7,617,005, which claims the benefit of U.S. Provisional Application No. 60/816,999 filed on Jun. 28, 2006. U.S. patent application Ser. No. 11/504,117, filed Aug. 14, 2006, now U.S. Pat. No. 7,617,005 is also a Continuation-In-Part application of each of the following:

(A) U.S. patent application Ser. No. 10/408,665, filed on Apr. 8, 2003, now U.S. Pat. No. 7,162,303, which claims the benefit of U.S. Provisional Application Nos. (a) 60/370,190, filed on Apr. 8, 2002, (b) 60/415,575, filed on Oct. 3, 2002, and (c) 60/442,970, filed on Jan. 29, 2003.

(B) U.S. patent application Ser. No. 11/189,563, filed on Jul. 25, 2005 now U.S. Pat. No. 8,145,316, which is a Continuation-In-Part application of U.S. patent application Ser. No. 11/129,765, filed on May 13, 2005, now U.S. Pat. No. 7,653,438, which claims the benefit of U.S. Provisional Application Nos. (a) 60/616,254, filed on Oct. 5, 2004, and (b) 60/624,793, filed on Nov. 2, 2004.

All of these applications are incorporated herein by reference in their entireties.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present invention relates to methods and apparatus for neuromodulation. More particularly, the present invention relates to methods and apparatus for achieving renal neuromodulation via thermal heating and/or cooling mechanisms.

BACKGROUND

Congestive Heart Failure ("CHF") is a condition that occurs when the heart becomes damaged and reduces blood flow to the organs of the body. If blood flow decreases sufficiently, kidney function becomes altered, which results in fluid retention, abnormal hormone secretions and increased constriction of blood vessels. These results increase the workload of the heart and further decrease the capacity of the heart to pump blood through the kidneys and circulatory system.

It is believed that progressively decreasing perfusion of the kidneys is a principal non-cardiac cause perpetuating the downward spiral of CHF. Moreover, the fluid overload and associated clinical symptoms resulting from these physiologic changes result in additional hospital admissions, poor quality of life and additional costs to the health care system.

In addition to their role in the progression of CHF, the kidneys play a significant role in the progression of Chronic Renal Failure ("CRF"), End-Stage Renal Disease ("ESRD"), hypertension (pathologically high blood pressure) and other cardio-renal diseases. The functions of the kidneys can be summarized under three broad categories: filtering blood and excreting waste products generated by the body's metabolism; regulating salt, water, electrolyte and acid-base balance; and secreting hormones to maintain vital organ blood flow. Without properly functioning kidneys, a patient will suffer water retention, reduced urine flow and an accumulation of waste toxins in the blood and body. These conditions result from reduced renal function or renal failure (kidney failure) and are believed to increase the workload of the heart. In a CHF patient, renal failure will cause the heart to further deteriorate as fluids are retained and blood toxins accumulate due to the poorly functioning kidneys.

It has been established in animal models that the heart failure condition results in abnormally high sympathetic activation of the kidneys. An increase in renal sympathetic nerve activity leads to decreased removal of water and sodium from the body, as well as increased renin secretion. Increased renin secretion leads to vasoconstriction of blood vessels supplying the kidneys, which causes decreased renal blood flow. Reduction of sympathetic renal nerve activity, e.g., via denervation, may reverse these processes.

Applicants have previously described methods and apparatus for treating renal disorders by applying a pulsed electric field to neural fibers that contribute to renal function. See, for example, Applicants' co-pending U.S. patent application Ser. No. (a) 11/129,765, filed on May 13, 2005, Ser. No. (b) 11/189,563, filed on Jul. 25, 2005, and Ser. No. (c) 11/363,867, filed Feb. 27, 2006, all of which are incorporated herein by reference in their entireties. A pulsed electric field ("PEF") may initiate renal neuromodulation, e.g., denervation, for example, via irreversible electroporation or via electrofusion. The PEF may be delivered from apparatus positioned intravascularly, extravascularly, intra-to-extravascularly or a combination thereof. Additional methods and apparatus for achieving renal neuromodulation, e.g., via localized drug delivery (such as by a drug pump or infusion catheter) or via use of a stimulation electric field, etc, are described, for example, in co-owned and co-pending U.S. patent application Ser. No. 10/408,665, filed Apr. 8, 2003, and U.S. Pat. No. 6,978,174, both of which are incorporated herein by reference in their entireties.

A potential challenge of using PEF systems for treating renal disorders is to selectively electroporate target cells without affecting other cells. For example, it may be desirable to irreversibly electroporate renal nerve cells that travel along or in proximity to renal vasculature, but it may not be desirable to damage the smooth muscle cells of which the vasculature is composed. As a result, an overly aggressive course of PEF therapy may persistently injure the renal vasculature, but an overly conservative course of PEF therapy may not achieve the desired renal neuromodulation.

Applicants have previously described methods and apparatus for monitoring changes in tissue impedance or conductivity in order to determine the effects of pulsed electric field therapy, e.g., to determine an extent of electroporation and/or its degree of irreversibility. See, for example, Applicant's co-pending U.S. patent application Ser. No. 11/233,814, filed Sep. 23, 2005, which is incorporated herein by reference in its entirety. However, in some patients it may be difficult or impractical to achieve such real-time monitoring when utilizing pulsed electric field neuromodulatory mechanisms. In some patients, this may necessitate re-intervention should it be established after the procedure that a degree of induced neuromodulation was not sufficient to achieve a desired treatment outcome. Thus, it would be desirable to achieve renal neuromodulation via more easily monitored and/or controlled neuromodulatory mechanisms.

BRIEF DESCRIPTION OF THE DRAWINGS

Several embodiments of the present invention will be apparent upon consideration of the following detailed description, taken in conjunction with the accompanying drawings, in which like reference characters refer to like parts throughout, and in which.

DETAILED DESCRIPTION

A. Overview

Figure 1:
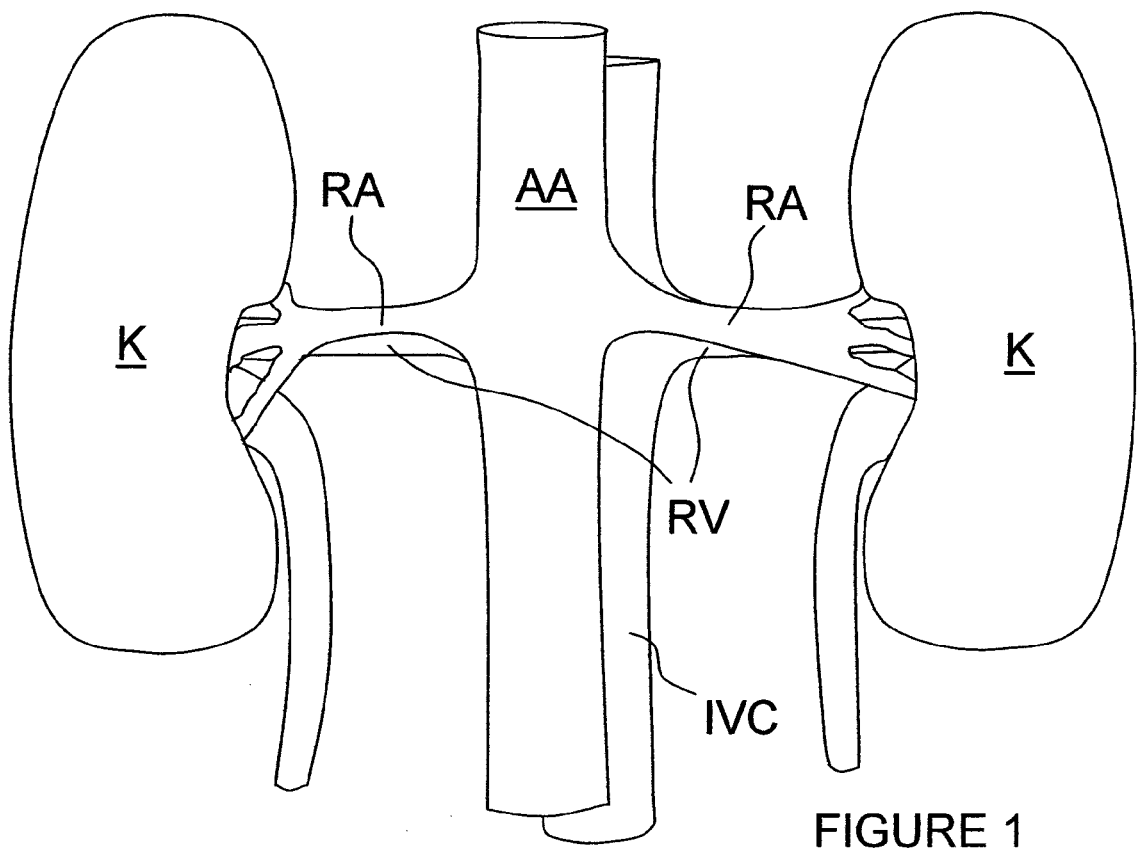
FIG. 1 is a schematic view illustrating human renal anatomy.

The present invention provides methods and apparatus for renal neuromodulation via thermal heating and/or thermal cooling mechanisms, e.g., to achieve a reduction in renal sympathetic nerve activity. Thermally-induced (via heating and/or cooling) neuromodulation may be achieved via apparatus positioned proximate target neural fibers, for example, positioned within renal vasculature (i.e., positioned intravascularly), positioned extravascularly, positioned intra-to-extravascularly or a combination thereof. Thermal neuromodulation by either heating or cooling may be due to direct effect to, or alteration of, the neural structures that is induced by the thermal stress. Additionally or alternatively, the thermal neuromodulation may at least in part be due to alteration of vascular structures, e.g., arteries, arterioles, capillaries or veins, which perfuse the target neural fibers or surrounding tissue. Furtherstill, the modulation may at least in part be due to electroporation of the target neural fibers or of surrounding tissue.

As used herein, thermal heating mechanisms for neuromodulation include both thermal ablation and non-ablative thermal injury or damage (e.g., via sustained heating or resistive heating). Thermal heating mechanisms may include raising the temperature of target neural fibers above a desired threshold, for example, above a body temperature of about 37° C., e.g., to achieve non-ablative thermal injury, or above a temperature of about 45° C. (e.g., above about 60° C.) to achieve ablative thermal injury.

As used herein, thermal cooling mechanisms for neuromodulation include non-freezing thermal slowing of nerve conduction and/or non-freezing thermal nerve injury, as well as freezing thermal nerve injury. Thermal cooling mechanisms may include reducing the temperature of target neural fibers below a desired threshold, for example, below the body temperature of about 37° C. (e.g., below about 20° C.) to achieve non-freezing thermal injury. Thermal cooling mechanisms also may include reducing the temperature of the target neural fibers below about 0° C., e.g., to achieve freezing thermal injury.

In addition to monitoring or controlling the temperature during thermal neuromodulation, a length of exposure to thermal stimuli may be specified to affect an extent or degree of efficacy of the thermal neuromodulation. The length of exposure to thermal stimuli is longer than instantaneous exposure, such as longer than about 30 seconds, or even longer than 2 minutes. Furthermore, the length of exposure can be less than 10 minutes, though this should in no way be construed as the upper limit of the exposure period. Exposure times measured in hours, days or longer, may be utilized to achieve desired thermal neuromodulation.

When conducting neuromodulation via thermal mechanisms, the temperature threshold discussed previously may be determined as a function of the duration of exposure to thermal stimuli. Additionally or alternatively, the length of exposure may be determined as a function of the desired temperature threshold. These and other parameters may be specified or calculated to achieve and control desired thermal neuromodulation.

In some embodiments, thermally-induced renal neuromodulation may be achieved via direct application of thermal cooling or heating energy to the target neural fibers. For example, a chilled or heated fluid can be applied at least proximate to the target neural fiber, or heated or cooled elements (e.g., a thermoelectric element or a resistive heating element) can be placed in the vicinity of the neural fibers. In other embodiments, thermally-induced renal neuromodulation may be achieved via indirect generation and/or application of the thermal energy to the target neural fibers, such as through application of a 'thermal' electric field, of high-intensity focused ultrasound, of laser irradiation, etc., to the target neural fibers. For example, thermally-induced renal neuromodulation may be achieved via delivery of a pulsed or continuous thermal electric field to the target neural fibers, the electric field being of sufficient magnitude and/or duration to thermally induce the neuromodulation in the target fibers (e.g., to heat or thermally ablate or necrose the fibers). Additional and alternative methods and apparatus may be utilized to achieve thermally-induced renal neuromodulation, as described hereinafter.

When utilizing thermal heating mechanisms for thermal neuromodulation, protective cooling elements, such as convective cooling elements, optionally may be utilized to protect smooth muscle cells or other non-target tissue from thermal damage during the thermally-induced renal neuromodulation. Likewise, when utilizing thermal cooling mechanisms, protective heating elements, such as convective heating elements, may be utilized to protect the non-target tissue. When thermal neuromodulation is achieved via thermal energy delivered intravascularly, the non-target tissue may be protected by utilizing blood flow as a conductive and/or convective heat sink that carries away excess thermal energy (hot or cold). For example, when blood flow is not blocked, the circulating blood may provide a relatively constant temperature medium for removing the excess thermal energy from the non-target tissue during the procedure. The non-target tissue additionally or alternatively may be protected by focusing the thermal heating or cooling energy on the target neural fibers such that an intensity of the thermal energy is insufficient to induce the thermal damage in the non-target tissue distant from the target neural fibers.

In some embodiments, methods and apparatus for real-time monitoring of an extent or degree of neuromodulation or denervation (e.g., an extent or degree of thermal damage) in the target neural fibers and/or of thermal damage in the non-target tissue may be provided. Likewise, real-time monitoring of the thermal energy delivery element may be provided. Such methods and apparatus may, for example, comprise a thermocouple or other temperature sensor for measuring the temperature of the monitored tissue or of the thermal energy delivery element. Power or total energy delivered additionally or alternatively may be monitored.

To better understand the structures of devices of the present invention and the methods of using such devices for thermally-induce renal neuromodulation, it is instructive to examine the renal anatomy in humans.

B. Renal Anatomy Summary

With reference to FIG. 1, the human renal anatomy includes the kidneys K, which are supplied with oxygenated blood by the renal arteries RA. The renal arteries are connected to the heart via the abdominal aorta AA. Deoxygenated blood flows from the kidneys to the heart via the renal veins RV and the inferior vena cava IVC.

Figure 2:
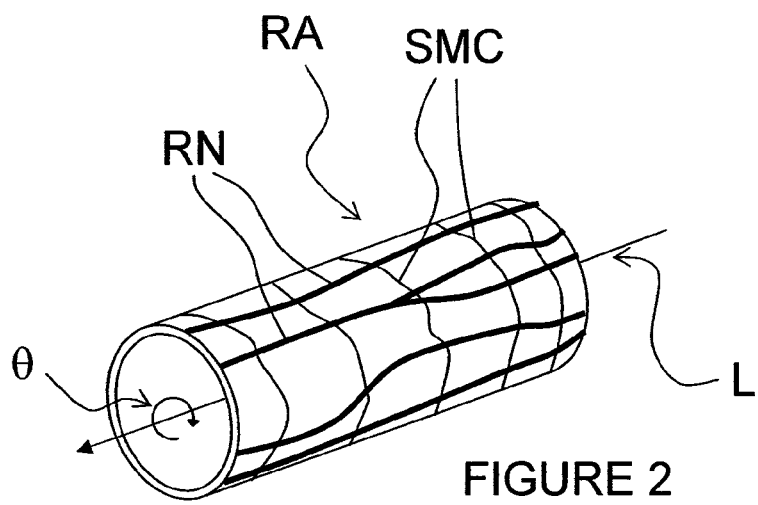
FIG. 2 is a schematic isometric detail view showing the location of the renal nerves relative to the renal artery.

FIG. 2 illustrates a portion of the renal anatomy in greater detail. More specifically, the renal anatomy also includes renal nerves RN extending longitudinally along the lengthwise dimension L of renal artery RA, generally within the adventitia of the artery. The renal artery RA has smooth muscle cells SMC that surround the arterial circumference and spiral around the angular axis θ of the artery. The smooth muscle cells of the renal artery accordingly have a lengthwise or longer dimension extending transverse (i.e., non-parallel) to the lengthwise dimension of the renal artery. The misalignment of the lengthwise dimensions of the renal nerves and the smooth muscle cells is defined as "cellular misalignment."

C. Embodiments of Apparatus and Methods for Neuromodulation

Figure 3:
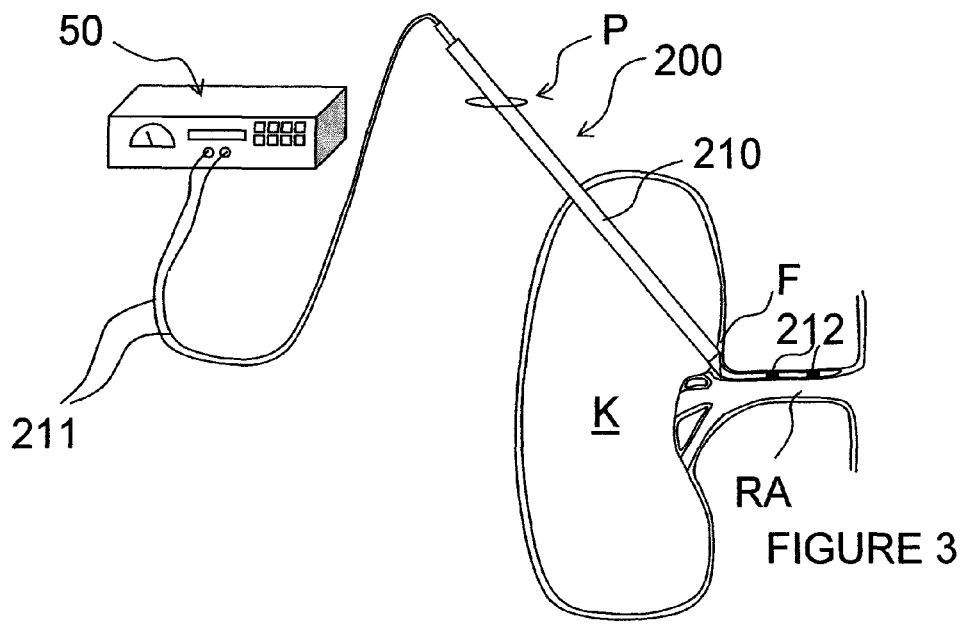
FIG. 3 is a schematic side view, partially in section, illustrating an example of an extravascular method and apparatus for thermal renal neuromodulation.

FIGS. 3-13 illustrate examples of systems and methods for thermally-induced renal neuromodulation. FIG. 3 shows one embodiment of an extravascular apparatus 200 that includes one or more electrodes configured to deliver a thermal electric field to renal neural fibers in order to achieve renal neuromodulation via heating. The apparatus of FIG. 3 is configured for temporary extravascular placement; however, it should be understood that partially or completely implantable extravascular apparatus additionally or alternatively may be utilized. Applicants have previously described extravascular pulsed electric field systems, for example, in co-pending U.S. patent application Ser. No. 11/189,563, filed Jul. 25, 2005, which has been incorporated herein by reference in its entirety.

In FIG. 3, apparatus 200 comprises a laparoscopic or percutaneous system having a probe 210 configured for insertion in proximity to the track of the renal neural supply along the renal artery or vein or hilum and/or within Gerota's fascia under, e.g., CT or radiographic guidance. At least one electrode 212 is configured for delivery through the probe 210 to a treatment site for delivery of a thermal electric field therapy. The electrode(s) 212, for example, may be mounted on a catheter and electrically coupled to a thermal electric field generator 50 via wires 211. In an alternative embodiment, a distal section of the probe 210 may have at least one electrode 212, and the probe may have an electrical connector to couple the probe to the field generator 50 for delivering a thermal electric field to the electrode(s) 212.

The field generator 50 is located external to the patient. The generator, as well as any of the electrode embodiments described herein, may be utilized with any embodiment of the present invention for delivery of a thermal electric field with desired field parameters, e.g., parameters sufficient to thermally or otherwise induce renal neuromodulation in target neural fibers via heating and/or electroporation. It should be understood that electrodes of embodiments described hereinafter may be electrically connected to the generator even though the generator is not explicitly shown or described with each embodiment. Furthermore, the field generator optionally may be positioned internal to the patient. Furtherstill, the field generator may additionally comprise or may be substituted with an alternative thermal energy generator, such as a thermoelectric generator for heating or cooling (e.g., a Peltier device), or a thermal fluid injection system for heating or cooling, etc.

The electrode(s) 212 can be individual electrodes that are electrically independent of each other, a segmented electrode with commonly connected contacts, or a continuous electrode. A segmented electrode may, for example, be formed by providing a slotted tube fitted onto the electrode, or by electrically connecting a series of individual electrodes. Individual electrodes or groups of electrodes 212 may be configured to provide a bipolar signal. The electrodes 212 may be dynamically assignable to facilitate monopolar and/or bipolar energy delivery between any of the electrodes and/or between any of the electrodes and an external ground pad. Such a ground pad may, for example, be attached externally to the patient's skin, e.g., to the patient's leg or flank. In FIG. 3, the electrodes 212 comprise a bipolar electrode pair. The probe 210 and the electrodes 212 may be similar to the standard needle or trocar-type used clinically for RF nerve block. Alternatively, the apparatus 200 may comprise a flexible and/or custom-designed probe for the renal application described herein.

In FIG. 3, the percutaneous probe 210 has been advanced through a percutaneous access site P into proximity with a patient's renal artery RA. The probe pierces the patient's Gerota's fascia F, and the electrodes 212 are advanced into position through the probe and along the annular space between the patient's artery and fascia. Once properly positioned, the target neural fibers may be heated via a pulsed or continuous electric field delivered across the bipolar electrodes 212. Such heating may, for example, ablate or cause non-ablative thermal injury to the target neural fibers, thereby at least partially denervating the kidney innervated by the target neural fibers. The electric field also may induce reversible or irreversible electroporation in the target neural fibers, which may compliment the thermal injury induced in the neural fibers. After treatment, the apparatus 200 may be removed from the patient to conclude the procedure.

Figure 4A:
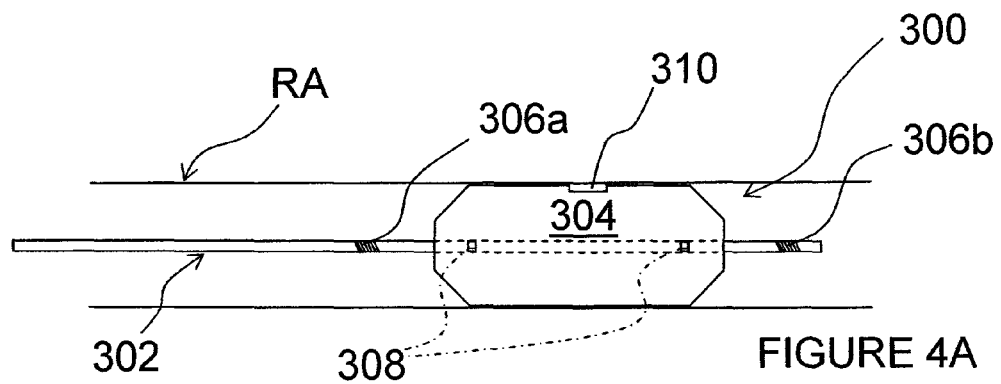
FIGS. 4A and 4B are schematic side views, partially in section, illustrating examples of intravascular methods and apparatus for thermal renal neuromodulation.
Figure 4B:
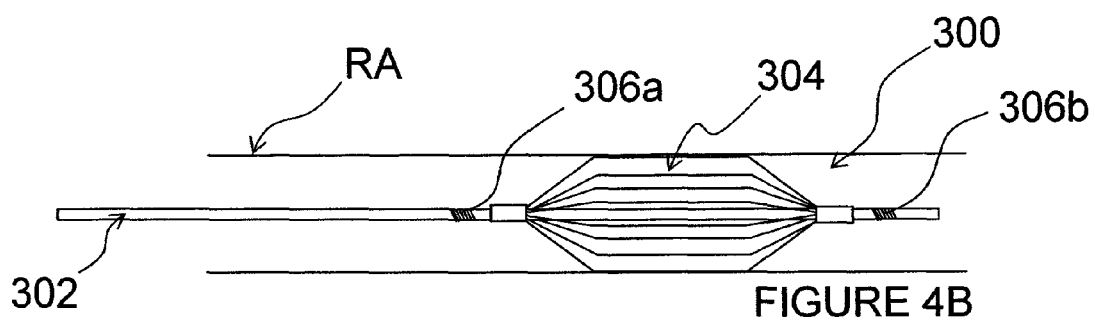

Referring now to FIGS. 4A and 4B, embodiments of intravascular systems for thermally-induced renal neuromodulation is described. Applicants have previously described intravascular pulsed electric field systems, for example, in co-pending U.S. patent application Ser. No. 11/129,765, filed May 13, 2005, which has been incorporated herein by reference in its entirety. The embodiments of FIG. 4 include an apparatus 300 comprising a catheter 302 having an optional positioning element 304 (e.g., a balloon, an expandable wire basket, other mechanical expanders, etc.), shaft electrodes 306a and 306b disposed along the shaft of the catheter, and optional radiopaque markers 308 disposed along the shaft of the catheter in the region of the positioning element 304. The electrodes 306a-b, for example, can be arranged such that the electrode 306a is near a proximal end of the positioning element 304 and the electrode 306b is near the distal end of the positioning element 304. The electrodes 306 are electrically coupled to the field generator 50 (see FIG. 3), which is disposed external to the patient, for delivery of a thermal electric field for heating of target neural fibers. In an alternative embodiment, one or more of the electrodes may comprise Peltier electrodes for cooling the target neural fibers to modulate the fibers.

The positioning element 304 optionally may center or otherwise position the electrodes 306a and 306b within a vessel. Additionally, as in FIG. 4A, the positioning element may comprise an impedance-altering element that alters the impedance between electrodes 306a and 306b during the therapy, for example, to better direct the thermal electric field across the vessel wall. This may reduce an energy required to achieve desired renal neuromodulation and may reduce a risk of injury to non-target tissue. Applicants have previously described use of a suitable impedance-altering element in co-pending U.S. patent application Ser. No. 11/266,993, filed Nov. 4, 2005, which is incorporated herein by reference in its entirety. When the positioning element 304 comprises an inflatable balloon as in FIG. 4A, the balloon may serve as both a centering element for the electrodes 306 and as an impedance-altering electrical insulator for directing an electric field delivered across the electrodes, e.g., for directing the electric field into or across the vessel wall for modulation of target neural fibers. Electrical insulation provided by the positioning element 304 may reduce the magnitude of applied energy or other parameters of the thermal electric field necessary to achieve desired heating at the target fibers.

Furthermore, the positioning element 304 optionally may be utilized as a cooling element and/or a heating element. For example, the positioning element 304 may be inflated with a chilled fluid that serves as a heat sink for removing heat from tissue that contacts the element. Conversely, the positioning element 304 optionally may be a heating element by inflating it with a warmed fluid that heats tissue in contact with the element. The thermal fluid optionally may be circulated and/or exchanged within the positioning element 304 to facilitate more efficient conductive and/or convective heat transfer. Thermal fluids also may be used to achieve thermal neuromodulation via thermal cooling or heating mechanisms, as described in greater detail herein below. The positioning element 304 (or any other portion of apparatus 300) additionally or alternatively may comprise one or more sensors for monitoring the process. In one embodiment, the positioning element 304 has a wall-contacting thermocouple 310 (FIG. 4A) for monitoring the temperature or other parameters of the target tissue, the non-target tissue, the electrodes, the positioning element and/or any other portion of the apparatus 300.

The electrodes 306 can be individual electrodes (i.e., independent contacts), a segmented electrode with commonly connected contacts, or a single continuous electrode. Furthermore, the electrodes 306 may be configured to provide a bipolar signal, or the electrodes 306 may be used together or individually in conjunction with a separate patient ground pad for monopolar use. As an alternative or in addition to placement of the electrodes 306 along the central shaft of the catheter 302, as in FIG. 4, the electrodes 306 may be attached to the positioning element 304 such that they contact the wall of the renal artery RA. In such a variation, the electrodes may, for example, be affixed to the inside surface, outside surface or at least partially embedded within the wall of the positioning element. FIG. 5 illustrate alternative wall-contacting electrodes.

In use, the catheter 302 may be delivered to the renal artery RA as shown, or it may be delivered to a renal vein or to any other vessel in proximity to neural tissue contributing to renal function, in a low profile delivery configuration through a guide catheter or other device. Alternatively, catheters may be positioned in multiple vessels for thermal renal neuromodulation, e.g., within both the renal artery and the renal vein. Multi-vessel techniques for pulsed electric field renal neuromodulation have been described previously, for example, in Applicant's co-pending U.S. patent application Ser. No. 11/451,728, filed Jul. 12, 2006, which is incorporated herein by reference in its entirety.

Once positioned within the renal vasculature as desired, the optional positioning element 304 may be expanded into contact with an interior wall of the vessel. A thermal electric field then may be generated by the field generator 50, transferred through the catheter 302 to the electrodes 306, and delivered via the electrodes 306 across the wall of the artery. The electric field thermally modulates the activity along neural fibers that contribute to renal function via heating. In several embodiments, the thermal modulation at least partially denervates the kidney innervated by the neural fibers via heating. This may be achieved, for example, via thermal ablation or via non-ablative damage of the target neural fibers. The electric field also may induce electroporation in the neural fibers.

In the embodiment of FIG. 4A, the positioning element 304 illustratively comprises an inflatable balloon, which may preferentially direct the electric field as discussed. In the embodiment of FIG. 4B, the positioning element comprises an expandable wire basket that substantially centers the electrodes 306 within the vessel without blocking blood flow through the vessel. During delivery of the thermal electric field (or of other thermal energy), the blood may act as a heat sink for conductive and/or convective heat transfer for removing excess thermal energy from the non-target tissue, thereby protecting the non-target tissue. This effect may be enhanced when blood flow is not blocked during energy delivery, as in the embodiment of FIG. 4B.

Use of the patient's blood as a heat sink is expected to facilitate delivery of longer or higher energy thermal treatments with reduced risk of damage to the non-target tissue, which may enhance the efficacy of the treatment at the target neural fibers. Although the embodiment of FIG. 4B illustratively comprises a positioning element for centering the electrodes without blocking flow, it should be understood that the positioning element may be eliminated and/or that the electrodes may be attached to the positioning element such that they are not centered in the vessel upon expansion of the centering element. In such embodiments, the patient's blood may still mitigate excess thermal heating or cooling to protect non-target tissues.

In addition or as an alternative to utilizing the patient's blood as a heat sink, a thermal fluid (hot or cold) may be injected into the vessel to remove excess thermal energy and protect the non-target tissues. The thermal fluid may, for example, be injected through the device catheter or through a guide catheter at a location upstream from an energy delivery element or at other locations relative to the tissue for which protection is sought. Furthermore, this method of using an injected thermal fluid to remove excess thermal energy from non-target tissues to protect the non-target tissues from thermal injury during therapeutic treatment of target tissues may be utilized in body lumens other than blood vessels.

One or more sensors, such as the thermocouple 310 of FIG. 4A, may be used to monitor the temperature(s) or other parameter(s) at the electrodes 306, at the wall of the vessel and/or at other desired locations along the apparatus or the patient's anatomy. The thermal neuromodulation may be controlled using the measured parameter(s) as feedback. This feedback may be used, for example, to maintain the parameter(s) below a desired threshold. For example, the parameter(s) may be maintained below a threshold that may cause injury to the non-target tissues. With blood flowing through the vessel, more thermal energy may be carried away, which may allow for longer or higher energy treatments than when blood flow is blocked in the vessel.

As discussed, when utilizing intravascular apparatus to achieve thermal neuromodulation, in addition or as an alternative to central positioning of the electrode(s) within a blood vessel, the electrode(s) optionally may be configured to contact an internal wall of the blood vessel. Wall-contacting electrode(s) may facilitate more efficient transfer of a thermal electric field across the vessel wall to target neural fibers, as compared to centrally-positioned electrode(s). In some embodiments, the wall-contacting electrode(s) may be delivered to the vessel treatment site in a reduced profile configuration, then expanded in vivo to a deployed configuration wherein the electrode(s) contact the vessel wall. In some embodiments, expansion of the electrode(s) is at least partially reversible to facilitate retrieval of the electrode(s) from the patient's vessel.

Figure 5A:
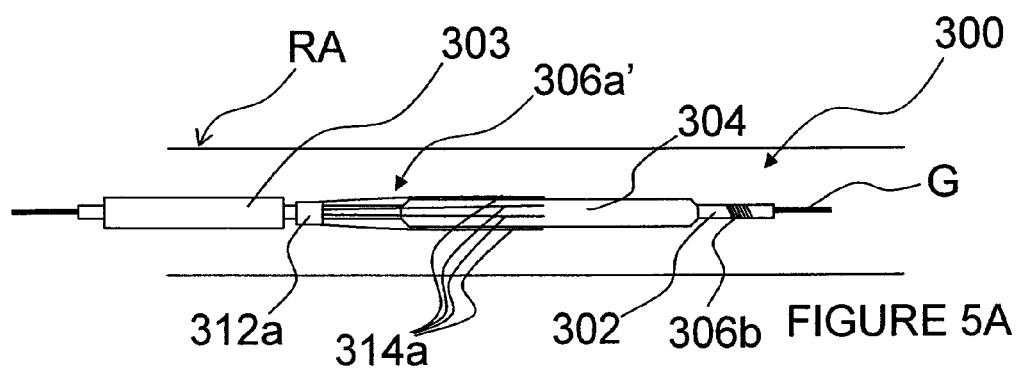
FIGS. 5A and 5B are schematic side views, partially in section, illustrating an alternative embodiment of the intravascular methods and apparatus of FIG. 4 comprising wall-contacting electrodes.
Figure 5B:
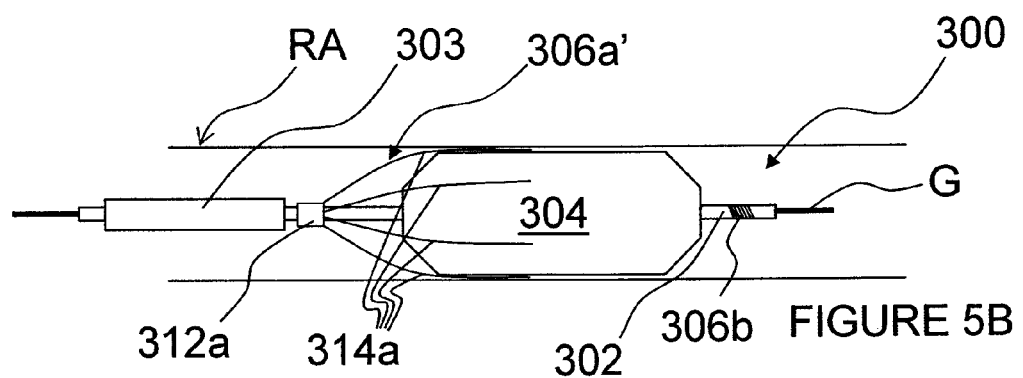

FIGS. 5A and 5B depict an illustrative embodiment of intravascular apparatus having electrodes configured to contact the interior wall of a vessel. The apparatus of FIGS. 5A and 5B is an alternative embodiment of the apparatus 300 of FIGS. 4A and 4B wherein the proximal electrode 306a of FIGS. 4A and 4B has been replaced with wall-contacting electrode 306a'. The wall-contacting electrode comprises proximal attachment 312a that connects the electrode to the shaft of the catheter 302 and is electrically coupled to the pulse generator. Extensions 314a extend from proximal attachment 312a and at least partially extend over a surface of positioning element 304. The extensions 314a optionally may be selectively insulated such that only a selective portion of the extensions, e.g., the distal tips of the extensions, are electrically active. The electrode 306a' optionally may be fabricated from a slotted tube, such as a stainless steel or shape-memory (e.g., NiTi) slotted tube. Furthermore, all or a portion of the electrode may be gold-plated to improve radiopacity and/or conductivity.

As seen in FIG. 5A, catheter 302 may be delivered over a guidewire G to a treatment site within the patient's vessel with the electrode 306a' positioned in a reduced profile configuration. Catheter 302 optionally may be delivered through a guide catheter 303 to facilitate such reduced profile delivery of the wall-contacting electrode. When positioned as desired at a treatment site, the electrode may be expanded into contact with the vessel wall by expanding the optional positioning element 304, as in FIG. 5B. A thermal monopolar or bipolar electric field then may be delivered across the vessel wall and between the electrodes 306a' and 306b to induce thermal neuromodulation, as discussed previously. The optional positioning element 304 may alter impedance within the blood vessel and more efficiently route the electrical energy across the vessel wall to the target neural fibers.

After delivery of the electric field, the electrode 306a' may be returned to a reduced profile to facilitate removal of the apparatus 300 from the patient. For example, the positioning element 304 may be collapsed (e.g., deflated), and the electrode 306a' may be contracted by withdrawing the catheter 302 within the guide catheter 303. Alternatively, the electrode may be fabricated from a shape-memory material biased to the collapsed configuration, such that the electrode self-collapses upon collapse of the positioning element.

Although in FIGS. 5A and 5B the electrode 306a' is expanded into contact with the vessel wall, it should be understood that the electrode alternatively may be fabricated from a self-expanding material biased such that the electrode self-expands into contact with the vessel wall upon positioning of the electrode distal of the guide catheter 303. A self-expanding embodiment of the electrode 306a' may obviate a need for the positioning element 304 and/or may facilitate maintenance of blood flow through the blood vessel during delivery of an electric field via the electrode. After delivery of the electric field, the self-expanding electrode 306a' may be returned to a reduced profile to facilitate removal of the apparatus 300 from the patient by withdrawing the catheter 302 within the guide catheter 303.

Figure 6A:
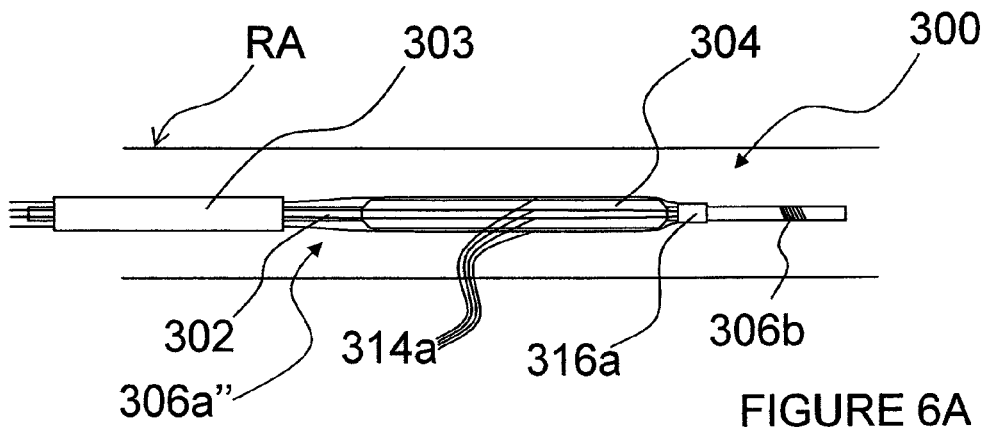
FIGS. 6A and 6B are schematic side views, partially in section, illustrating an additional alternative embodiment of the intravascular methods and apparatus of FIG. 4 comprising alternative wall-contacting electrodes.
Figure 6B:
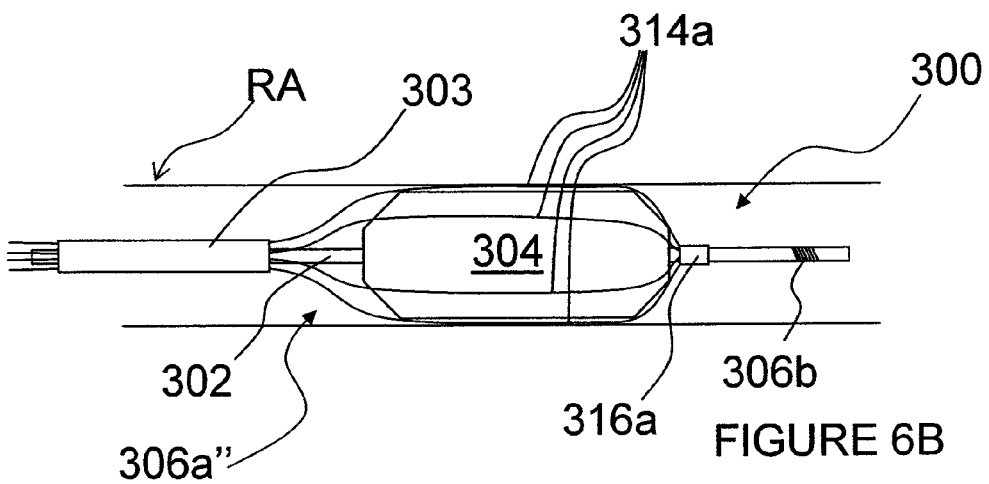

FIGS. 6A and 6B depict another embodiment of the apparatus and methods of FIGS. 4A and 4B comprising a wall-contacting electrode. As an alternative to the proximal attachment 312a of electrode 306a' of FIGS. 5A and 5B, the electrode 306a" of FIG. 6 comprises distal attachment 316a for coupling the electrode to the shaft of catheter 302 on the distal side of the positioning element 304. Distal attachment of the electrode allows the electrode to extend over the entirety of the positioning element 304 and may facilitate contraction of the electrode 306a" after thermal neuromodulation. For example, the electrode 306a" can be contracted by proximally retracting the extensions 312a relative to the catheter 302 during or after contraction of the positioning element 304. FIG. 6A shows the electrode 306a" in the reduced profile configuration, while FIG. 6B shows the electrode in the expanded, wall-contacting configuration.

Figure 7A:
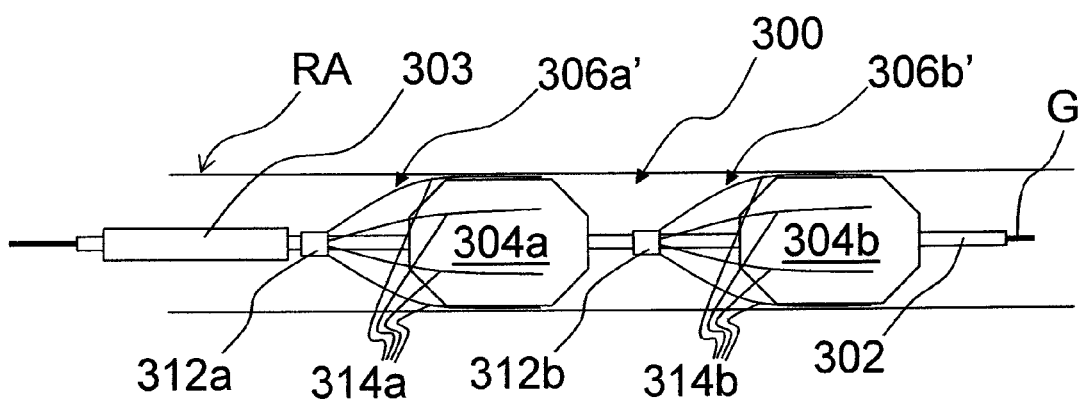
FIGS. 7A and 7B are schematic side views, partially in section, illustrating other alternative embodiments of the intravascular methods and apparatus of FIG. 4 comprising multiple wall-contacting electrodes.
Figure 7B:
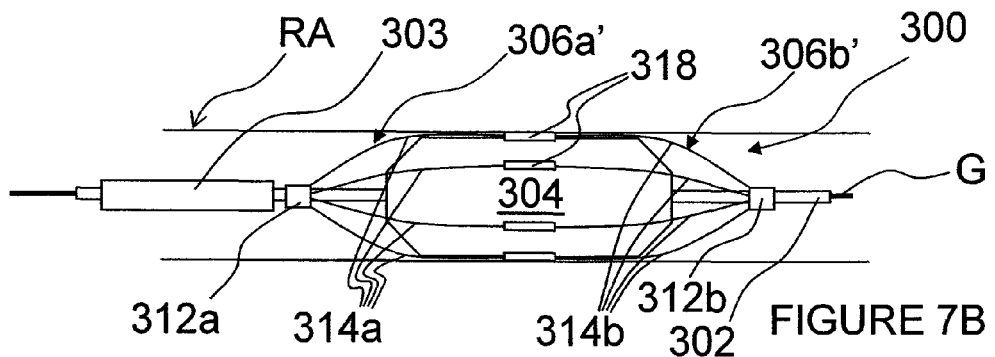

FIGS. 7A and 7B show additional alternative embodiments of the methods and apparatus of FIGS. 4A and 4B. In FIGS. 7A and 7B, the apparatus 300 comprises both the proximal electrode 306a' of FIGS. 5A and 5B, as well as a wall-contacting distal electrode 306b'. The embodiment of FIG. 7A comprises proximal and distal positioning elements 304a and 304b, respectively, for expanding the proximal and distal wall-contacting electrodes 306a' and 306b', respectively, into contact with the vessel wall. The embodiment of FIG. 7B comprises only a single positioning element 304, but the distal wall-contacting electrode 306b' is proximal facing and positioned over the distal portion of the positioning element 304 to facilitate expansion of the distal electrode 306b'. In the embodiment of FIG. 7B, the extensions of the proximal and distal electrodes optionally may be connected along non-conductive connectors 318 to facilitate collapse and retrieval of the electrodes post-treatment.

A bipolar electric field may be delivered between the proximal and distal wall-contacting electrodes, or a monopolar electric field may be delivered between the proximal and/or distal electrode(s) and an external ground. Having both the proximal and distal electrodes in contact with the wall of the vessel may facilitate more efficient energy transfer across the wall during delivery of a thermal electric field, as compared to having one or both of the proximal and distal electrodes centered within the vessel.

In addition to extravascular and intravascular systems for thermally-induced renal neuromodulation, intra-to-extravascular systems may be provided. The intra-to-extravascular systems may, for example, have electrode(s) that are delivered to an intravascular position, and then at least partially passed through/across the vessel wall to an extravascular position prior to delivery of a thermal electric field. Intra-to-extravascular positioning of the electrode(s) may place the electrode(s) in closer proximity to target neural fibers for delivery of a thermal electric field, as compared to fully intravascular positioning of the electrode(s). Applicants have previously described intra-to-extravascular pulsed electric field systems, for example, in co-pending U.S. patent application Ser. No. 11/324,188, filed Dec. 29, 2005, which is incorporated herein by reference in its entirety.

Figure 8:
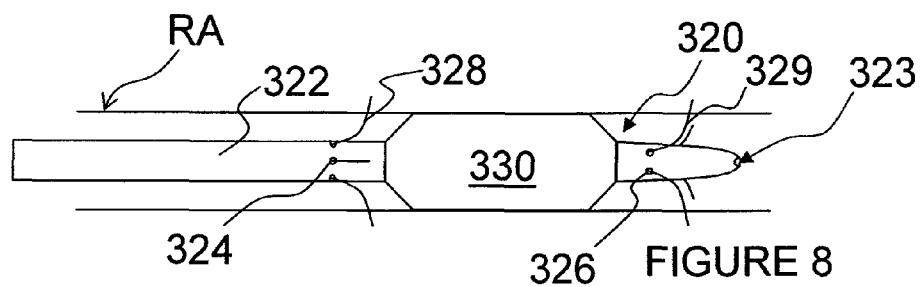
FIG. 8 is a schematic side view, partially in section, illustrating an example of an intra-to-extravascular method and apparatus for thermal renal neuromodulation.

With reference to FIG. 8, one embodiment of an intra-to-extravascular ("ITEV") system for thermally-induced renal neuromodulation is described. ITEV system 320 comprises a catheter 322 having (a) a plurality of proximal electrode lumens terminating at proximal side ports 324, (b) a plurality of distal electrode lumens terminating at distal side ports 326, and (c) a guidewire lumen 323. The catheter 322 preferably comprises an equal number of proximal and distal electrode lumens and side ports. The system 320 also includes proximal needle electrodes 328 that may be advanced through the proximal electrode lumens and the proximal side ports 324, as well as distal needle electrodes 329 that may be advanced through the distal electrode lumens and the distal side ports 326.

Catheter 322 comprises an optional expandable positioning element 330, which may comprise an inflatable balloon or an expandable basket or cage. In use, the positioning element 330 may be expanded prior to deployment of the needle electrodes 328 and 329 in order to position or center the catheter 322 within the patient's vessel (e.g., within renal artery RA). Centering the catheter 322 is expected to facilitate delivery of all needle electrodes to desired depths within/external to the patient's vessel (e.g., to deliver all of the needle electrodes approximately to the same depth). In FIG. 8, the illustrated positioning element 330 is positioned between the proximal side ports 324 and the distal side ports 326, i.e., between the delivery positions of the proximal and distal electrodes. However, it should be understood that the positioning element 330 additionally or alternatively may be positioned at a different location or at multiple locations along the length of the catheter 322 (e.g., at a location proximal of the side ports 324 and/or at a location distal of the side ports 326).

As illustrated in FIG. 8, the catheter 322 may be advanced to a treatment site within the patient's vasculature (e.g., to a treatment site within the patient's renal artery RA) over a guidewire (not shown) via the lumen 323. During intravascular delivery, the electrodes 328 and 329 may be positioned such that their non-insulated and sharpened distal regions are positioned within the proximal and distal lumens, respectively. Once positioned at a treatment site, a medical practitioner may advance the electrodes via their proximal regions that are located external to the patient. Such advancement causes the distal regions of the electrodes 328 and 329 to exit side ports 324 and 326, respectively, and pierce the wall of the patient's vasculature such that the electrodes are positioned extravascularly via an ITEV approach.

The proximal electrodes 328 can be connected to electric field generator 50 as active electrodes, and the distal electrodes 329 can serve as return electrodes. In this manner, the proximal and distal electrodes form bipolar electrode pairs that align the thermal electric field with a longitudinal axis or direction of the patient's vasculature. As will be apparent, the distal electrodes 329 alternatively may comprise the active electrodes and the proximal electrodes 328 may comprise the return electrodes. Furthermore, the proximal and/or the distal electrodes may comprise both active and return electrodes. Furtherstill, the proximal and/or the distal electrodes may be utilized in combination with an external ground for delivery of a monopolar thermal electric field. Any combination of active and distal electrodes may be utilized, as desired.

When the electrodes 328 and 329 are connected to generator 50 and positioned extravascularly, and with the positioning element 330 optionally expanded, delivery of the thermal electric field may proceed to achieve desired renal neuromodulation via heating. The electric field also may induce electroporation. After achievement of the thermally-induced renal neuromodulation, the electrodes may be retracted within the proximal and distal lumens, and the positioning element 330 may be collapsed for retrieval. ITEV system 320 then may be removed from the patient to complete the procedure. Additionally or alternatively, the system may be repositioned to provide therapy at another treatment site, such as to provide bilateral renal neuromodulation.

As discussed previously, cooling elements, such as convective cooling elements, may be utilized to protect non-target tissues like smooth muscle cells from thermal damage during thermally-induced renal neuromodulation via heat generation. Non-target tissues additionally or alternatively may be protected by focusing the thermal energy on the target neural fibers such that an intensity of the thermal energy is insufficient to induce thermal damage in non-target tissues distant from the target neural fibers.

Although FIGS. 3-8 illustratively show bipolar apparatus, it should be understood that monopolar apparatus alternatively may be utilized. For example, an active monopolar electrode may be positioned intravascularly, extravascularly or intra-to-extravascularly in proximity to target neural fibers that contribute to renal function. A return electrode ground pad may be attached to the exterior of the patient. Finally, a thermal electric field may be delivered between the in vivo monopolar electrode and the ex vivo ground pad to effectuate desired thermally-induced renal neuromodulation. Monopolar apparatus additionally may be utilized for bilateral renal neuromodulation.

The embodiments of FIGS. 3-8 illustratively describe methods and apparatus for thermally-induced renal neuromodulation via delivery of thermal electric fields that modulate the target neural fibers. However, it should be understood that alternative methods and apparatus for thermally-induced (via both heating and cooling) renal neuromodulation may be provided. For example, electric fields may be used to cool and modulate the neural fibers, e.g., via thermoelectric or Peltier elements. Thermally-induced renal neuromodulation optionally may be achieved via direct application of thermal energy to the target neural fibers. Such direct thermal energy may be generated and/or transferred in a variety of ways, such as via resistive heating, via delivery of a heated or chilled fluid (see FIGS. 9 and 11), via a Peltier element (see FIG. 10), etc. Thermally-induced renal neuromodulation additionally or alternatively may be achieved via application of high-intensity focused ultrasound to the target neural fibers (see FIG. 12). Additional and alternative methods and apparatus for thermally-induced renal neuromodulation may be used in accordance with the present invention.

Figure 9:
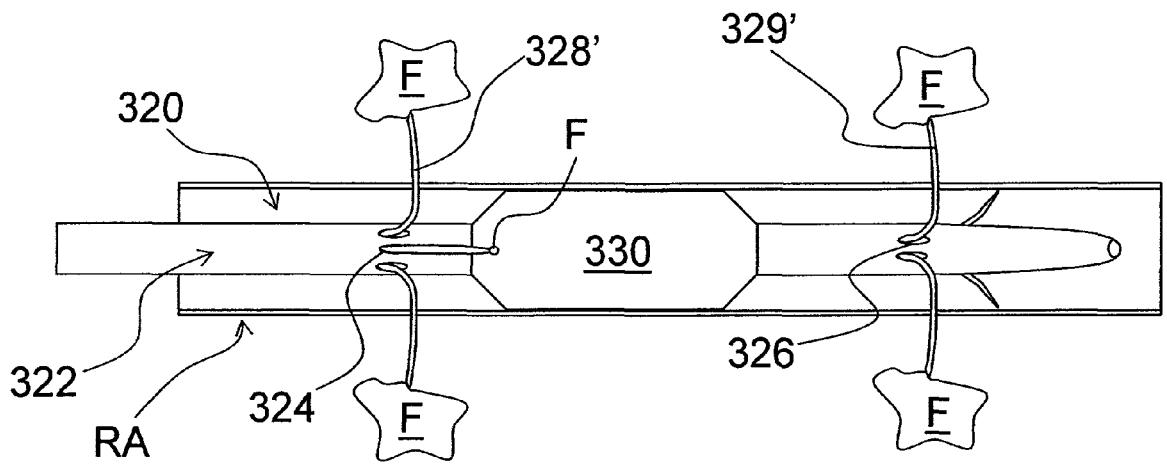
FIG. 9 is a schematic side view, partially in section, of an alternative embodiment of the method and apparatus of FIG. 8 configured for thermal renal neuromodulation via direct application of thermal energy.

With reference now to FIG. 9, an alternative embodiment of the apparatus and methods of FIG. 8 is described that is configured for thermally-induced neuromodulation via direct application of thermal energy. In the embodiment of FIG. 9, the electrodes 328 and 329 of FIG. 8 have been replaced with infusion needles 328' and 329', respectively. A thermal fluid F may be delivered through the needles to the target neural fibers. The thermal fluid may be heated in order to raise the temperature of the target neural fibers above a desired threshold. For example, the temperature of the neural fibers can be raised above a body temperature of about 37° C., or above a temperature of about 45° C. Alternatively, the thermal fluid may be chilled to reduce the temperature of the target neural fibers below a desired threshold. For example, the neural fibers can be cooled to below the body temperature of about 37° C., or further cooled below about 20° C., or still further cooled below a freezing temperature of about 0° C. As will be apparent, in addition to intra-to-extravascular delivery of a thermal fluid, the thermal fluid may be delivered intravascularly (e.g., may inflate and/or be circulated through a balloon member), extravascularly (e.g., may be circulated through a vascular cuff) or a combination thereof.

In addition or as alternative to injection of a thermal fluid to the target neural fibers through infusion needles 328' and 329', an alternative neuromodulatory agent, such as a drug or medicament, may be injected to modulate, necrose or otherwise block or reduce transmission along the target neural fibers. Examples of alternative neuromodulatory agents include, but are not limited to, phenol and neurotoxins, such as botulinum toxin. Additional neuromodulatory agents, per se known, will be apparent to those of skill in the art.

Figure 10:
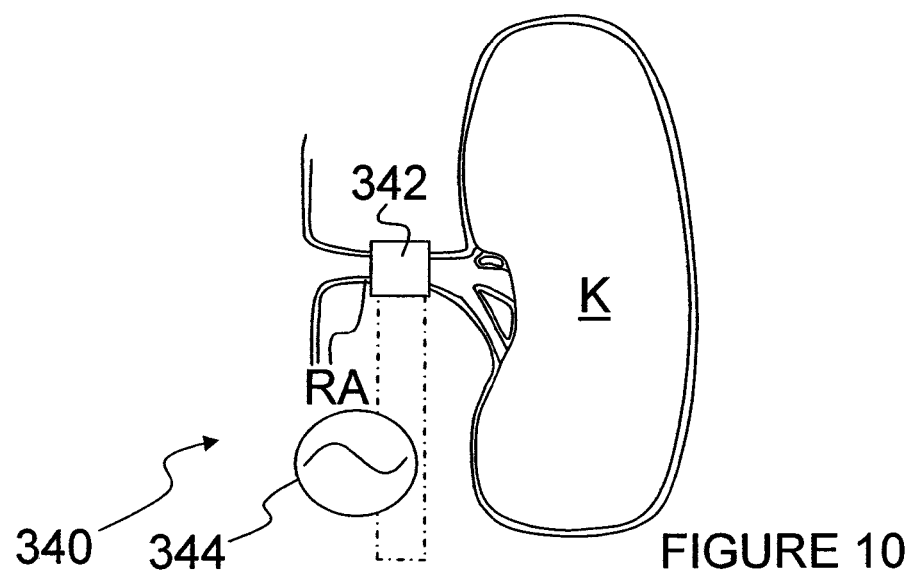
FIG. 10 is a schematic side view, partially in section, illustrating a method and apparatus for thermal renal neuromodulation comprising a thermoelectric element suitable for direct application of thermal energy to target neural fibers.

FIG. 10 shows another method and apparatus for thermal renal neuromodulation via direct application of thermal energy to the target neural fibers. The apparatus 340 comprises renal artery cuff 342 having one or more integrated thermoelectric elements that are electrically coupled to an internal or external power supply 344. The thermoelectric element utilizes the well-known Peltier effect (i.e., the establishment of a thermal gradient induced by an electric voltage) to achieve thermal renal neuromodulation.

An electric current is passed from the power supply to the thermoelectric element, which comprises two different metals (e.g., a p-type and an n-type semiconductor) that are connected to each other at two junctions. The current induces a thermal gradient between the two junctions, such that one junction cools while the other is heated. Reversal of the polarity of the voltage applied across the two junctions reverses the direction of the thermal gradient.

Either the hot side or the cold side of the thermoelectric element faces radially inward in order to heat or cool, respectively, the target neural fibers that travel along the renal artery to achieve thermal renal neuromodulation. Optionally, the radially outward surface of the thermoelectric element may be insulated to reduce a risk of thermal damage to the non-target tissues. The cuff 342 may comprise one or more temperature sensors, such as thermocouples, for monitoring the temperature of the target neural fibers and/or of the non-target tissues.

Figure 11:
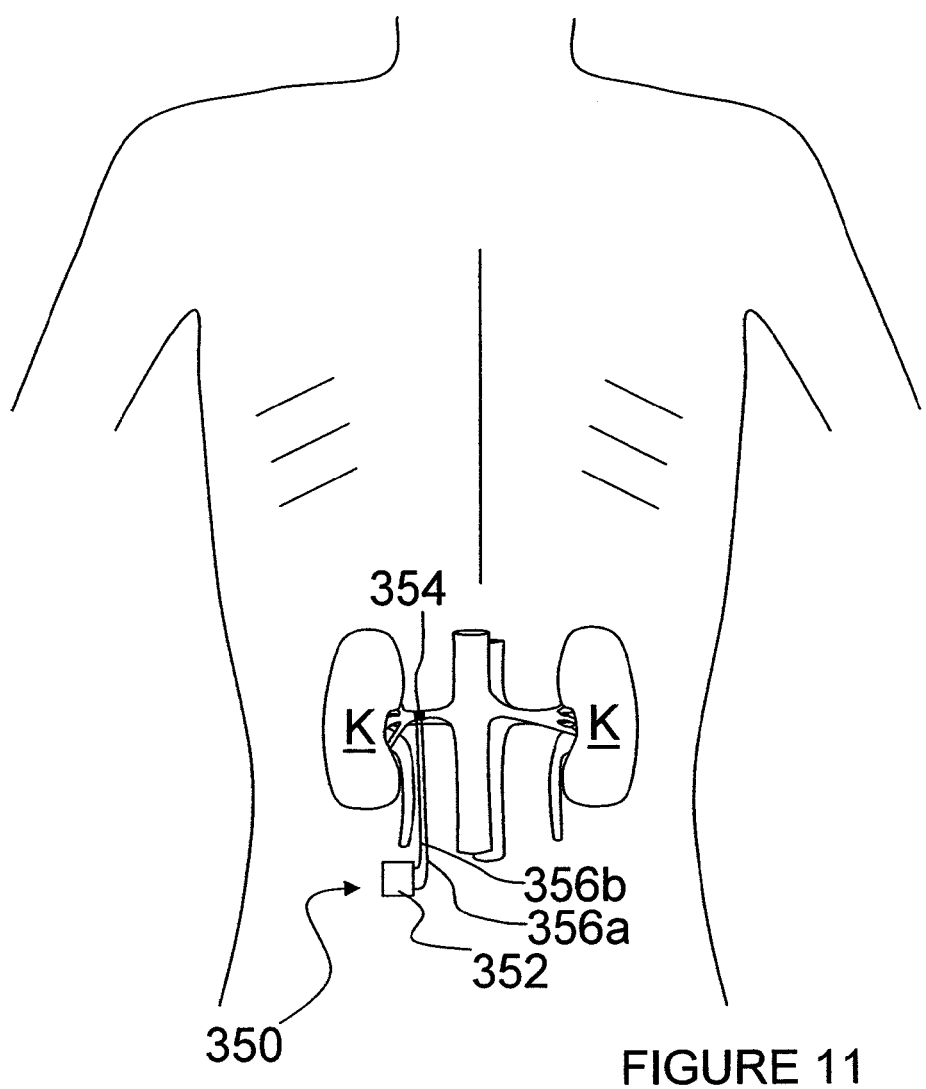
FIG. 11 is a schematic side view, partially in section, illustrating another method and apparatus for thermal renal neuromodulation comprising a thermoelectric element.

FIG. 11 shows another method and apparatus utilizing the Peltier effect. The apparatus 350 comprises an implanted or external pump 352 connected to a renal artery cuff 354 via inlet fluid conduit 356*a* and outlet fluid conduit 356*b*. The inlet fluid conduit transfers fluid from the pump to the cuff, while the outlet fluid conduit transfers fluid from the cuff to the pump to circulate fluid through the cuff. A reservoir of fluid may be located in the cuff, the pump and/or in the fluid conduits.

The pump 352 further comprises one or more thermoelectric or other thermal elements in heat exchange contact with the fluid reservoir for cooling or heating the fluid that is transferred to the cuff to thermally modulate the target neural fibers. The apparatus 350 optionally may have controls for automatic or manual control of fluid heating or cooling, as well as fluid circulation within the cuff. Furthermore, the apparatus may comprise temperature and/or renal sympathetic neural activity monitoring or feedback control. Although the apparatus illustratively is shown unilaterally treating neural fibers innervating a single kidney, it should be understood that bilateral treatment of neural fibers innervating both kidneys alternatively may be provided.

Thermal renal neuromodulation alternatively may be achieved via high-intensity focused ultrasound, either pulsed or continuous. High intensity focused ultrasound also may induce reversible or irreversible electroporation in the target neural fibers. Furthermore, the ultrasound may be delivered over a full 360° (e.g. when delivered intravascularly) or over a radial segment of less than 360° (e.g., when delivered intravascularly, extravascularly, intra-to-extravascularly, or a combination thereof). In FIG. 12, the apparatus 360 comprises a catheter 362 having ultrasound transducers 364 positioned along the shaft of the catheter within an inflatable balloon 366. The ultrasound transducers are coupled to an ultrasound signal generator via conductors 365. The balloon comprises an acoustically reflective portion 368 of a surface of the balloon for reflecting an ultrasound wave, as well as an acoustically transmissive portion 369 of the surface for passage of the wave through the balloon. In this manner, the wave may be focused as shown at a focal point or radius P positioned a desired focal distance from the catheter shaft. In an alternative embodiment, the transducers may be attached directly to the balloon.

The focal distance may be specified or dynamically variable such that, when positioned within a blood vessel, the ultrasonic wave is focused at a desired depth on target neural fibers outside of the vessel. For example, a family of catheter sizes may be provided to allow for a range of specified focal distances. A dynamically variable focal distance may be achieved, for example, via calibrated expansion of the balloon.

Figure 12A:
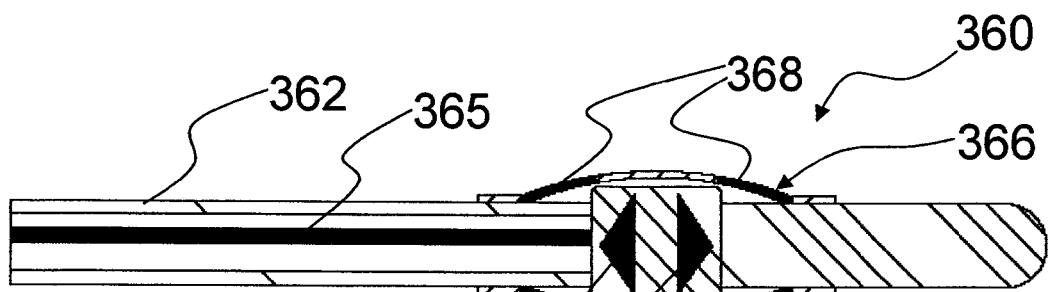
FIGS. 12A and 12B are schematic side views, partially in section, illustrating a method and apparatus for thermal renal neuromodulation via high-intensity focused ultrasound.
Figure 12B:
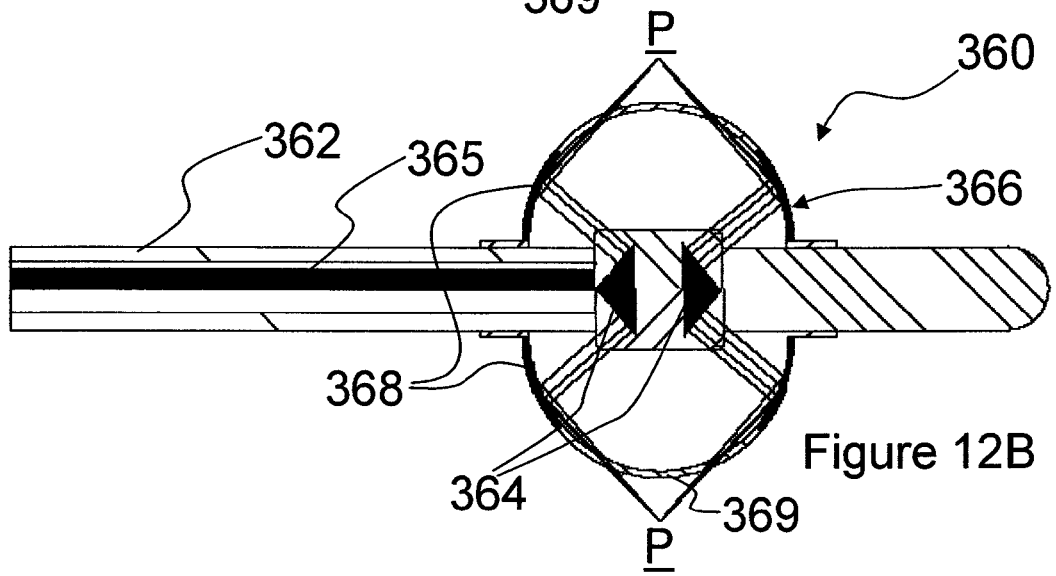
Figure 13:
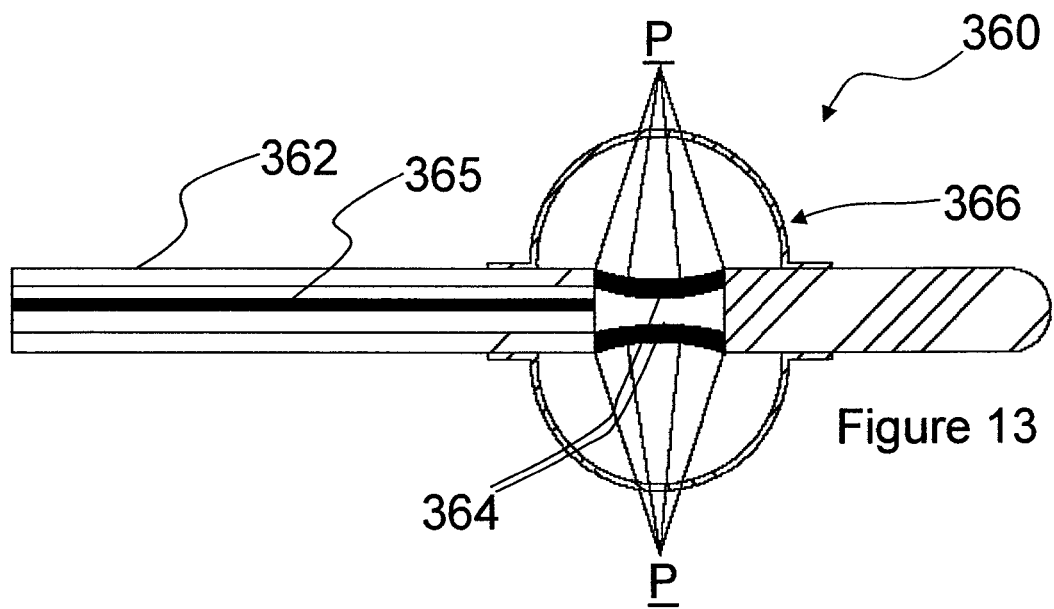
FIG. 13 is a schematic side view, partially in section, illustrating an alternative embodiment of the apparatus and method of FIG. 12.

Focusing the ultrasound wave may produce a reverse thermal gradient that protects the non-target tissues and selectively affect the target neural fibers to achieve thermal renal neuromodulation via heating. As a result, the temperature at the vessel wall may be less than the temperature at the target tissue. FIG. 12A shows the apparatus 360 in a reduced delivery and retrieval configuration, while FIG. 12B shows the apparatus in an expanded deployed configuration. FIG. 13 shows an alternative embodiment of the apparatus 360 wherein the ultrasound transducers 364' are concave, such that the ultrasound signal is self-focusing without need of the reflective portion of the balloon 366 (e.g., the balloon may be acoustically transmissive at all points).

The apparatus described above with respect to FIGS. 3-13 optionally may be used to quantify the efficacy, extent or cell selectivity of thermally-induced renal neuromodulation in order to monitor and/or control the neuromodulation. As discussed previously, the apparatus may further comprise one or more sensors, such as thermocouples or imaging transducers, for measuring and monitoring one or more parameters of the apparatus, of the target neural fibers and/or of the non-target tissues. For example, a temperature rise or drop above or below certain thresholds is expected to thermally ablate, non-ablatively injure, freeze or otherwise damage the target neural fibers, thereby modulating the target neural fibers.

Figure 14A:
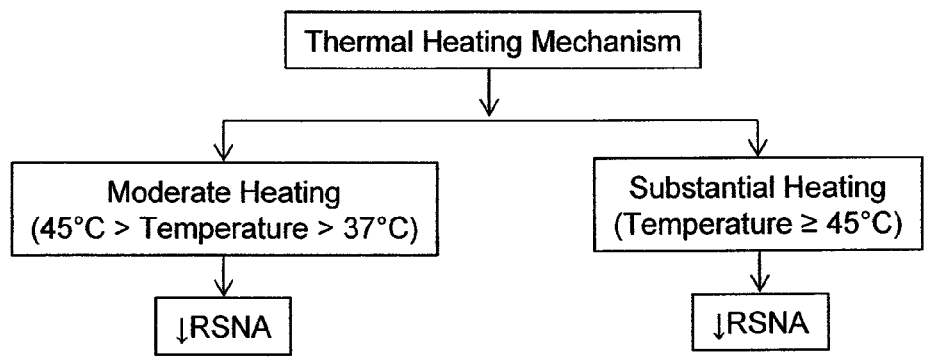
FIGS. 14A and 14B are schematic diagrams for classifying the various types of thermal neuromodulation that may be achieved with the apparatus and methods of the present invention.
Figure 14B:
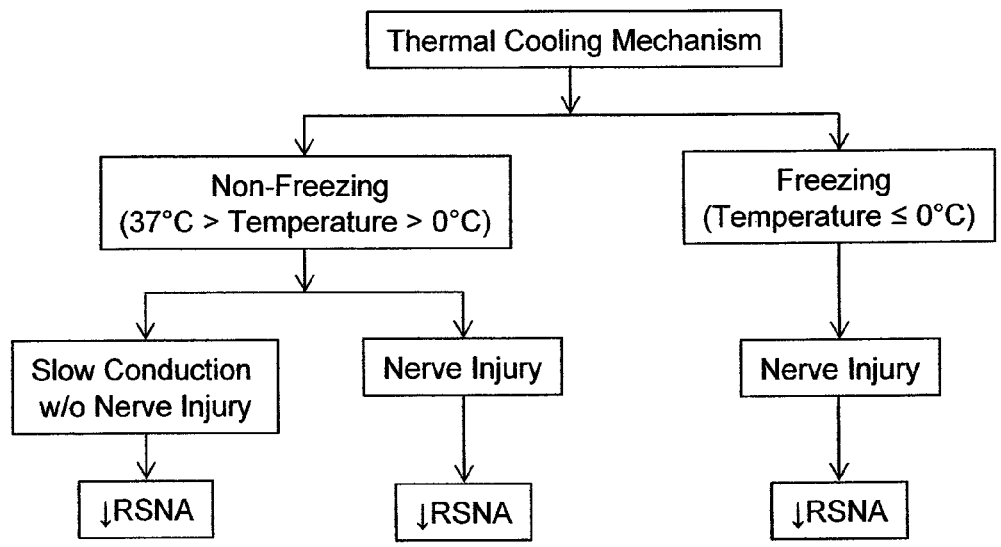

FIGS. 14A and 14B classify the various types of thermal neuromodulation that may be achieved with the apparatus and methods of the present invention. FIGS. 14A and 14B are provided only for the sake of illustration and should in no way be construed as limiting. FIG. 14A classifies thermal neuromodulation due to heat exposure. As shown, exposure to heat in excess of a body temperature of about 37° C., but below a temperature of about 45° C., may induce thermal injury via moderate heating of the target neural fibers or of vascular structures that perfuse the target fibers. For example, this may induce non-ablative thermal injury in the fibers or structures. Exposure to heat above a temperature of about 45° C., or above about 60° C., may induce thermal injury via substantial heating of the fibers or structures. For example, such higher temperatures may thermally ablate the target neural fibers or the vascular structures. Regardless of the type of heat exposure utilized to induce the thermal neuromodulation, a reduction in renal sympathetic nerve activity ("RSNA") is expected.

As seen in FIG. 14B, thermal cooling for neuromodulation includes non-freezing thermal slowing of nerve conduction and/or nerve injury, as well as freezing thermal nerve injury. Non-freezing thermal cooling may include reducing the temperature of the target neural fibers or of the vascular structures that feed the fibers to temperatures below the body temperature of about 37° C., or below about 20° C., but above the freezing temperature of about 0° C. This non-freezing thermal cooling may either slow nerve conduction or may cause direct neural injury. Slowed nerve conduction may imply continuous or intermittent cooling of the target neural fibers to sustain the desired thermal neuromodulation, while direct neural injury may require only a discrete treatment to achieve sustained thermal neuromodulation. Thermal cooling for neuromodulation also may include freezing thermal nerve injury, e.g., reducing the temperature of the target neural fibers or of the vascular structures that feed the fibers to temperatures below the freezing point of about 0° C. Regardless of the type of cold exposure utilized to induce the thermal neuromodulation (freezing or non-freezing), a reduction in renal sympathetic nerve activity ("RSNA") is expected.

It is expected that thermally-induced renal neuromodulation, whether delivered extravascularly, intravascularly, intra-to-extravascularly or a combination thereof, may alleviate clinical symptoms of CHF, hypertension, renal disease, myocardial infarction, atrial fibrillation, contrast nephropathy and/or other cardio-renal diseases for a period of months, potentially up to six months or more. This time period may be sufficient to allow the body to heal; for example, this period may reduce the risk of CHF onset after an acute myocardial infarction, thereby alleviating a need for subsequent re-treatment. Alternatively, as symptoms reoccur, or at regularly scheduled intervals, the patient may receive repeat therapy.

Although preferred illustrative variations of the present invention are described above, it will be apparent to those skilled in the art that various changes and modifications may be made thereto without departing from the invention. It is intended in the appended claims to cover all such changes and modifications that fall within the true spirit and scope of the invention.

The invention claimed is:

1. An ultrasound apparatus for thermally-induced renal neuromodulation, the apparatus comprising:
    a catheter sized and shaped for delivery within a blood vessel to a vicinity of neural fibers that contribute to renal function;
    an ultrasound transducer carried by the catheter, wherein the ultrasound transducer is configured to transmit ultrasound energy waves to target renal neural fibers outside of the blood vessel to thermally induce modulation of target neural fibers while protecting non-target tissue in the blood vessel wall from thermal injury; and
    an expandable member carried by a distal region of the catheter,
    wherein the expandable member is configured to vary between a reduced configuration for delivery and retrieval and an expanded deployed configuration, and
    wherein the ultrasound transducer is positioned on a shaft of the catheter and within the expandable member.

2. The apparatus of claim 1 wherein the expandable member comprises an inflatable balloon.

3. The apparatus of claim 2 wherein the balloon comprises an acoustically transmissive portion configured to allow passage of the ultrasound energy waves to the target neural fibers.

4. The apparatus of claim 3 wherein the balloon further comprises an acoustically reflective portion configured to reflect ultrasound energy waves via the acoustically transmissive portion to the target neural fibers.

5. The apparatus of claim 4 wherein:
    the ultrasound transducer comprises a first ultrasound transducer configured to deliver a first ultrasound energy wave, and wherein the apparatus further comprises a second ultrasound transducer configured to produce a second ultrasound energy wave; and
    the acoustically reflective portion and the acoustically transmissive portion are configured to transmit the first and second ultrasound energy waves to a focal distance point proximate to the target neural fibers.

6. The apparatus of claim 5 wherein the balloon is configured to transmit the first and second ultrasound energy waves to the focal distance point via different transmission paths.

7. The apparatus of claim 5 wherein expansion of the balloon is calibrated to dynamically vary the focal distance point.

8. The apparatus of claim 3 wherein the ultrasound transducer comprises a concave transducer configured to self-focus the ultrasound energy wave to the target neural fibers.

9. The apparatus of claim 1, further comprising an ultrasound signal generator operatively connected to the ultrasound transducer, and wherein the ultrasound signal generator is configured to deliver thermal neuromodulation therapy via the ultrasound transducer to the target neural fibers.

10. The apparatus of claim 9, further comprising a temperature sensor.

11. The apparatus of claim 9 wherein a reverse thermal gradient is produced when the ultrasound transducer transmits focused ultrasound energy waves to the target renal neural fibers outside of the blood vessel, and wherein the reverse thermal gradient results in a temperature at a wall of the blood vessel wall being less than a temperature at the target neural fibers.

12. The apparatus of claim 1, further comprising an imaging transducer.

* * * * *